(12) United States Patent
Krishnan et al.

(10) Patent No.: US 12,216,121 B2
(45) Date of Patent: Feb. 4, 2025

(54) METHODS AND COMPOSITIONS FOR SPACIAL AND TEMPORAL MEASUREMENT OF CATALYTIC ACTIVITY

(71) Applicant: The University of Chicago, Chicago, IL (US)

(72) Inventors: Yamuna Krishnan, Chicago, IL (US); Krishna Dan, Chicago, IL (US); Aneesh T. Veetil, Chicago, IL (US); Kasturi Chakraborty, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 434 days.

(21) Appl. No.: 16/603,722

(22) PCT Filed: Apr. 12, 2018

(86) PCT No.: PCT/US2018/027391
§ 371 (c)(1),
(2) Date: Oct. 8, 2019

(87) PCT Pub. No.: WO2018/191561
PCT Pub. Date: Oct. 18, 2018

(65) Prior Publication Data
US 2021/0096129 A1    Apr. 1, 2021

Related U.S. Application Data

(60) Provisional application No. 62/484,666, filed on Apr. 12, 2017.

(51) Int. Cl.
*G01N 33/573* (2006.01)
*C07H 21/04* (2006.01)
*G01N 21/64* (2006.01)

(52) U.S. Cl.
CPC ........... *G01N 33/573* (2013.01); *C07H 21/04* (2013.01); *G01N 21/6428* (2013.01)

(58) Field of Classification Search
CPC ............. G01N 33/573; G01N 21/6428; G01N 2458/10; G01N 33/5308; C07H 21/04
See application file for complete search history.

(56) References Cited

U.S. PATENT DOCUMENTS

| | | | |
|---|---|---|---|
| 4,582,789 A * | 4/1986 | Sheldon, III | C07D 493/04 435/6.1 |
| 8,153,437 B2 | 4/2012 | Krishnan et al. | |
| 8,216,850 B2 | 7/2012 | Krishnan et al. | |
| 9,250,252 B2 | 2/2016 | Krishnan et al. | |
| 9,404,123 B2 | 8/2016 | Krishnan et al. | |
| 9,772,336 B2 | 9/2017 | Krishnan et al. | |
| 10,175,232 B2 | 1/2019 | Krishnan et al. | |
| 10,443,089 B2 | 10/2019 | Krishnan et al. | |
| 2009/0081679 A1 | 3/2009 | Keefe et al. | |
| 2010/0290992 A1 | 11/2010 | Seela et al. | |
| 2010/0304370 A1 | 12/2010 | Krishnan et al. | |
| 2011/0033706 A1 | 2/2011 | Krishnan | |
| 2011/0223676 A1 | 9/2011 | Krishnan et al. | |
| 2012/0082975 A1 | 4/2012 | Krishnan et al. | |
| 2012/0258452 A1 | 10/2012 | Krishnan et al. | |
| 2014/0056818 A1 | 2/2014 | Krishnan et al. | |
| 2014/0335568 A1 | 11/2014 | Krishnan et al. | |
| 2016/0002713 A1 | 1/2016 | Krishnan et al. | |
| 2016/0069912 A1 | 3/2016 | Krishnan et al. | |
| 2016/0370355 A1 | 12/2016 | Krishnan et al. | |
| 2016/0376441 A1 | 12/2016 | Mallet et al. | |
| 2017/0101669 A1 | 4/2017 | Krishnan et al. | |
| 2018/0245137 A1 | 8/2018 | Krishnan et al. | |

FOREIGN PATENT DOCUMENTS

| | | | |
|---|---|---|---|
| IN | 1471/CHE/2011 | | 6/2013 |
| IN | 3252/CHE/2011 | | 6/2013 |
| WO | 2013054286 A1 | | 4/2013 |
| WO | 2014132191 A2 | | 9/2014 |
| WO | 2015/159122 A1 | | 10/2015 |
| WO | WO-2016187284 A1 * | 11/2016 | ........... C12N 15/113 |
| WO | 2018/191561 A1 | | 10/2018 |

OTHER PUBLICATIONS

Saha (Nature Nanotechnology (2015) vol. 10, pp. 645-652).*
(Continued)
(Continued)Dan (Nature Nanotechnology (2019) vol. 14, pp. 252-259).*
(Continued)https://biologydictionary.net/nucleic-acid/, downloaded Aug. 12, 2022>.*
(Continued)Gulnik (.FEBS Letters 413 (1997) 379-384).*
(Continued)Kamath, R.S., et al., "Genome-Wide RNAi Screening in Caenorhabditis elegans", Methods, 2003, vol. 30, pp. 313-321.
(Continued)Shen, W-C., et al., "Disulfide Spacer Between Methotrexate and Poly(D-lysine)", The Journal of Biological Chemistry, 1985, vol. 260(20), pp. 10905-10908.
(Continued)Yang, J., et al., "Evaluation of Disulfide Reduction During Receptor-Mediated Endocytosis by Using FRET Imaging", PNAS, Sep. 12, 2006, vol. 103(37), pp. 13872-13877.

*Primary Examiner* — Steven Pohnert
(74) *Attorney, Agent, or Firm* — McDonnell Boehnen Hulbert & Berghoff LLP

(57) ABSTRACT

Described herein are nucleic acid molecules and complexes useful for spatiotemporally mapping intra-endosmal thiol disulphide exchange. Aspects of the disclosure relate to a composition comprising a first nucleic acid conjugated to a normalization moiety; and a second nucleic acid conjugated to a catalytic substrate; wherein reaction of the substrate with a catalyst produces a detectable product; and wherein the first and second nucleic acids are complementary or substantially complementary. Further aspects relate to a composition comprising: a first nucleic acid conjugated to a normalization moiety and to a catalytic substrate; and a second nucleic acid; wherein reaction of the substrate with a catalyst produces a detectable product; and wherein the first and second nucleic acids are complementary or substantially complementary.

18 Claims, 23 Drawing Sheets

Specification includes a Sequence Listing.

(56) References Cited

OTHER PUBLICATIONS

Modi, S. et al., "Two DNA Nanomachines Map pH Changes Along Intersecting Endocytic Pathways Inside the Same Cell", Nature Nanotechnology, , vol. 8, May 26, 2013, pp. 459-467.
Amit, I., et al., "Voices of Biotech", 25th anniversary issue, Nature Biotechnology, Mar. 2016, vol. 34(3), pp. 270-275.
Banerjee, A., et al., "A Novel Type of Quantum Dot-Transferrin Conjugate using DNA Hybridization Mimics Intracellular Recycling of Endogenous Transferrin", Nanoscale, 2017, vol. 9(40), pp. 15453-15460.
Banerjee, A., et al., "Fast, Efficient and Stable Conjugation of Multiple DNA Strands on Colloidal Quantum Dots", Bioconjugate Chem., May 20, 2015, vol. 26(8), pp. 1582-1589.
Banerjee, A., et al., "Controlled Release of Encapsulated Cargo from a DNA Icosahedron using a Chemical Trigger", Angew. Chem. Int. Ed., May 28, 2013, vol. 52(27), pp. 6854-6857.
Bhatia, D., et al., "A Method to Encapsulate Molecular Cargo within DNA Icosahedra", Methods Mol. Biol., 2013, vol. 991, Chapter 8, pp. 65-80.
Bhatia, D., et al., "Gene Delivery: Designer DNA Give RNAi More Spine", Nature Nanotechnology, Jun. 3, 2012, vol. 7(6), pp. 344-346.
Bhatia, D., et al., "Synthetic, Biofunctional Nucleic Acid Based Molecular Devices", Curr. Opin. Biotechnol., Jun. 11, 2011, vol. 22(4), pp. 475-484.
Bhattacharya, S., et al., "2-Halooxyethylene Ethers of Cholesterol as Novel Single Component, Room Temperature Cholesteric LC Materials", Mol. Cryst. Liq. Cryst., 2002, vol. 381, pp. 33-41.
Bhattacharya, S., et al., "Vesicle Formation from Oligo(Oxyethylene)-Bearing Cholesteryl Amphiphiles: Site-Selective Effects of Oxyethylene Units on the Membrane Order and Thickness", Langmuir, Mar. 9, 2001, vol. 17, pp. 2067-2075.
Bhattacharya, S., et al., "First Report of Phase Selective Gelation of Oil from Oil/Water Mixtures. Possible Implications Toward Containing Oil Spills", Chem. Commun., Jan. 8, 2001, pp. 185-186.
Chakraborty, S., et al., "The Predictive Power of Synthetic Nucleic Acid Technologies in RNA Biology", Accounts of Chemical Research, Apr. 8, 2014, vol. 47(6), pp. 1710-1719.
Chakraborty, S., et al., "Kinetic Hybrid I-Motifs: Intercepting DNA with RNA to Form a DNA(2)-RNA(2) Hybrid I-Motif", Biochimie, Mar. 2, 2008, vol. 90(7), pp. 1088-1095.
Chakraborty, S., et al., "The RNA2-PNA2 Hybrid I-Motif—A Novel RNA-Based Building Block", Chem. Commun., Oct. 17, 2007, Issue 1, pp. 70-72.
Devany, J., et al., "Sub-Cellular Nanorheology Reveals Lysosomal Viscosity as a Reporter of Lysosomal Storage Diseases", Nano Letters, Jan. 9, 2018, vol. 18, pp. 1351-1359.
Ganesh, K.N., et al., "Nucleic Acids—Chemistry and Applications", J. Org. Chem., Dec. 20, 2013, vol. 78(24), pp. 12283-12287.
Ghodke, H.B., et al., "The I-Tetraplex Building Block: Rational Design and Controlled Fabrication of Robust 1D DNA Scaffolds via Non-Watson Crick Self Assembly", Angew. Chem. Int. Ed., Mar. 2, 2007, vol. 46, pp. 2646-2649.
Ghosh, A., et al., "At a Long Awaited Turning Point", Nature Nanotechnology, Jul. 2014, vol. 9(7), pp. 491-494.
Krishnan-Ghosh, Y., et al., "Advantage of the Ether Linkage between the Positive Charge and the Cholesteryl Skeleton in Cholesterol-Based Amphiphiles as Vectors for Gene Delivery", Bioconjugate Chem., Mar.-Apr. 2002, vol. 13(2), pp. 378-384.
Horsey, I., et al., "Enhanced Cooperative Binding of Oligonucleotides to Form DNA Duplexes Mediated by Metal Ion Chelation", Chem. Commun., Aug. 5, 2002, vol. 17, pp. 1950-1951.
Jani, M.S., et al., "A DNA-Based Fluorescent Probe Maps NOS3 Activity with Sub-Cellular Spatial Resolution", Nature Chem. Biol., 2020, https://doi.org/10.1038/s41589-020-0491-3, pp. 1-13.
Jani, M.S., et al., "Precision Immunomodulation with Synthetic Nucleic Acid Technologies", Nature Reviews Materials, Jun. 2019, vol. 4, pp. 451-458.

Joshi, H., et al., "Probing the Structure and in Silico Stability of Cargo Loaded DNA Icosahedron using MD Simulations", Nanoscale, 2017, vol. 9(13), pp. 4467-4477.
Krishnan, Y., et al., "Introduction: Nucleic Acid Nanotechnology", Chem. Rev., May 22, 2019, vol. 119(10), pp. 6271-6272.
Krishnan-Ghosh, Y., et al., "PNA Forms an I-Motif", Chem. Commun., Sep. 23, 2005, vol. 42, pp. 5278-5280.
Krishnan-Ghosh, Y., et al., "Dynamic Covalent Chemistry on Self-Templating PNA Oligomers: Formation of a Bimolecular PNA Quadruplex", Chem. Commun., May 11, 2005, vol. 24, pp. 3068-3070.
Krishnan-Ghosh, Y., et al., "A PNA4 Quadruplex", J. Am. Chem. Soc., Apr. 23, 2004, vol. 126(19), pp. 5944-5945.
Krishnan-Ghosh, Y., et al., "Formation of an Interlocked Quadruplex Dimer by d(GGGT)", J. Am. Chem. Soc., 2004, vol. 126(35), pp. 11009-11016.
Krishnan-Ghosh, Y., et al., "Thermal Lipid Order-Disorder Transitions in Mixtures of Cationic Cholesteryl Lipid Analogues and Dipalmitoyl Phosphatidylcholine Membranes", J. Phys. Chem. B, Oct. 3, 2001, vol. 105(42), pp. 10257-10265.
Krishnan-Ghosh, Y., et al., "Structure of Cholest-5-en-3 beta-oxy-5-bromopentane by Single-Crystal X-ray Diffraction at 130 K", J. Mol. Structure, 2001, vol. 560(1-3), pp. 345-355.
Lannes, L., et al., "Tuning the pH-Response of I-Motif DNA Oligonucleotides", ChemBioChem, Jun. 30, 2015, vol. 16(11), pp. 1647-1656.
Modi, S., et al., "A Method to Map Spatiotemporal pH Changes Inside Living Cells using a pH Triggered DNA Nanoswitch", Methods Mol. Biol., 2011, vol. 749, Chapter 5, pp. 61-77.
Modi, S., et al., "Structural DNA Nanotechnology: From Bases to Bricks, from Structure to Function", J. Phys. Chem. Lett., Jun. 14, 2010, vol. 1(13), pp. 1994-2005.
Modi, S., et al., "A DNA Nanomachine that Maps Spatial and Temporal pH Changes in Living Cells", Nature Nanotechnology, Apr. 6, 2009, vol. 4(5), pp. 325-330.
Pal, A., et al., "Molecular Mechanism of Physical Gelation of Hydrocardons by Fatty Acid Amides of Natural Amino Acids", Tetrahedron, May 22, 2007, vol. 63(31), pp. 7334-7348.
Patel, A., et al., "ATP is a Biological Hydrotrope", Science, May 19, 2017, vol. 356(6339), pp. 753-756.
Pitchiaya, S., et al., "First Blueprint, Now Bricks: DNA as Construction Material on the Nanoscale", Chem. Soc. Rev., Sep. 12, 2006, vol. 35(11), pp. 1111-1121.
Prakash, V., et al., "Quantitative Maps of Endosomal DNA Processing by Single Molecule Counting", Angew. Chem. Int. Ed., 2019, vol. 58(10), pp. 3073-3076.
Saha, S., et al., "Tunable, Colorimetric DNA Based pH Sensors Mediated by A-Motif Formation", Chem. Commun., 2012, vol. 48(19), pp. 2513-2515.
Saha, S., et al., "pH Toggled DNA Architectures: Reversible Assembly of 3WJs into Extended 1D Architectures through A-Motif Formation", Small, May 19, 2010, vol. 6(12), pp. 1288-1292.
Saminathan, A., et al., "Chemically Resolving Lysosome Populations in Live Cells," Trends in Biochem. Sci., Apr. 2020, vol. 45(4), pp. 365-366.
Sayresmith, N., et al., "Photostable Voltage Sensitive Dyes Based on Simple, Solvatofluorochromic, Asymmetric Thiazolothiazoles", J. Am. Chem. Soc., Nov. 27, 2019, vol. 141(47), pp. 18780-18790.
Sharma, S., et al., "A DNA Aptamer for Cyclic Adenosine Monophosphate that Shows Adaptive Recognition", ChemBioChem, Jan. 15, 2020, vol. 21(1-2), pp. 157-162.
Sharma, S., et al., "A Fluorescent Nucleic Acid Nanodevice Quantitatively Images Elevated Cyclic AMP in Membrane-Bound Compartments", Small, Jul. 14, 2014, vol. 10(21), pp. 4276-4280.
Surana, S., et al., "A Method to Map Spatiotemporal pH Changes in a Multicellular Living Organism using a DNA Nanosensor", Methods Mol. Biol., 2013, vol. 991, Chapter 2, pp. 9-23.
Veetil, A., et al., "Cell-Targetable DNA Nanocapsules for Spatiotemporal Release of Caged Bioactive Small Molecules", Nature Nanotechnology, Dec. 2017, vol. 12(12), pp. 1183-1189.
Wills, A.J., et al., "Synthesis of a Polymer-Supported Oxazolidine Aldehyde for Asymmetric Chemistry", J. Org. Chem., Aug. 15, 2002, vol. 67(19), pp. 6646-6652.

(56) References Cited

OTHER PUBLICATIONS

Zajac, M., et al., "What Biologists Want from their Chloride Reporters: A Conversation between Chemists and Biologists", J. Cell Sci., Jan. 23, 2020, vol. 133(2), pp. 1-13.
Altschul, S.F., et al., "Basic Local Alignment Search Tool", J. Mol. Biol., 1990, vol. 215, pp. 403-410.
Appelqvist, H., et al., "The Lysosome: From Waste Bag to Potential Therapeutic Target", J. Mol. Cell. Biol., 2013, vol. 5, pp. 214-226.
Berg, T.O., et, al., "Use of Glycyl-L-phenylalanine 2-naphthylamide, a Lysosome-Disrupting Cathepsin C Substrate, to Distinguish Between Lysosomes and Prelysosomal Endocytic Vacuoles", Biochem. J., 1994, vol. 300(Pt. 1), pp. 229-236.
Bhatia, D., et al., "Icosahedral DNA Nanocapsules by Modular Assembly", Angew. Chem. Int. Ed. Engl. 2009, vol. 48, pp. 4134-4137.
Bhatia, D., et al., "A Synthetic Icosahedral DNA-Based Host-Cargo Complex for Functional In Vivo Imaging", Nat. Commun., 2011, vol. 2(339), pp. 1-8.
Bhatia, D., et al., "Quantum Dot-Loaded Monofunctionalized DNA Icosahedra for Single-Particle Tracking of Endocytic Pathways", Nat. Nanotechnol., 2016, vol. 11(12), pp. 1112-1119.
Bhuniya, S., et al., "An Activatable Theranostic for Targeted Cancer Therapy and Imaging", Angew. Chem. Int. Ed. Engl., 2014, vol. 53, pp. 4469-4474.
Blum, G., et, al., "Noninvasive Optical Imaging of Cysteine Protease Activity Using Fluorescently Quenched Activity-Based Probes", Nat. Chem. Biol., Oct. 2007, vol. 3(10), pp. 668-677.
Burgdorf, S., et al., "Spatial and Mechanistic Separation of Cross-Presentation and Endogenous Antigen Presentation". Nat. Immunol., May 2008, vol. 9(5), pp. 558-566.
Burgoyne, J.R., et al., "Cysteine Redox Sensor in PKGIa Enables Oxidant-Induced Activation", Science, Sep. 7, 2007, vol. 317(5843), pp. 1393-1397.
Chakraborty, K., et al., "High Lumenal Chloride in the Lysosome is Critical for Lysosome Function", elife, 2017, vol. 6, e28862, pp. 1-21.
Chakraborty, K., et al., "Nucleic Acid-Based Nanodevices in Biological Imaging", Annu. Rev. Biochem., 2016, vol. 85, pp. 349-373.
Chan, P., et al., "Autopalmitoylation of TEAD Proteins Regulates Transcriptional Output of the Hippo Pathway", Nat. Chem. Biol., Apr. 2016, vol. 12(4), pp. 282-289.
Collins, D.S., et al., "Reduction of Disulfide Bonds Within Lysosomes is a Key Step in Antigen Processing", J. Immunol., 1991, vol. 147, pp. 4054-4059.
Crivat, G., et al., "Imaging Proteins Inside Cells with Fluorescent Tags", Trends Biotechnol., Jan. 2012, vol. 30 (1), pp. 8-16.
Dihazi, H., et al., "Secretion of ERP57 is Important for Extracellular Matrix Accumulation and Progression of Renal Fibrosis, and is an Early Sign of Disease Onset", J. Cell Sci., 2018, vol. 126(16), pp. 3649-3663.
Dubikovskaya, E.A., et al., "Overcoming Multidrug Resistance of Small-Molecule Therapeutics through Conjugation with Releasable Octaarginine Transporters", Proc. Natl. Acad. Sci., Aug. 26, 2008, vol. 105(34), pp. 12128-12133.
Eschenlauer, S.C.P., et al., "The Caenorhabditis elegans ERp60 Homolog Protein Disulfide Isomerase-3 has Disulfide Isomerase and Transglutaminase-like Cross-Linking Activity and is Involved in the Maintenance of Body Morphology", J. Biol. Chem., 2003, vol. 278(6), pp. 4227-4237.
Famulok, M., et al., "Functional Aptamers and Aptazymes in Biotechnology, Diagnostics, and Therapy", Chem Rev., 2007, vol. 107(9), pp. 3715-3743.
Feener, E., et al., "Cleavage of Disulfide Bonds in Endocytosed Macromolecules", J. Biol.Chem., 1990, vol. 265(31), pp. 18780-18785.
Forman-Kay, J.D., et al., "Relationship Between Electrostatics and Redox Function in Human Thioredoxin: Characterization of pH Titration Shifts Using Two-Dimensional Homo- and Heteronuclear NMR", Biochemistry, 1992, vol. 31(13), pp. 3442-3452.

Gething, M.J., et al., "Protein Folding in the Cell", Nature, Jan. 2, 1992, vol. 355, pp. 33-45.
Guermonprez, P., et al., "ER-Phagosome Fusion Defines an MHC Class I Cross-Presentation Compartment in Dendritic Cells", Nature, Sep. 25, 2003, vol. 425, pp. 397-402.
Hawkins, H.C., et al., "Comparison of the Activities of Protein Disulphide-Isomerase and Thioredoxin in Catalysing Disulphide Isomerization in a Protein Substrate", Biochem. J., 1991, vol. 275(Pt. 2), pp. 349-353.
Hogg, P.J., "Disulfide Bonds as Switches for Protein Function", Trends Biochem. Sci., Apr. 2003, vol. 28(4), pp. 210-214.
Jansens, A., et al., "Coordinated Nonvectorial Folding in a Newly Synthesized Multidomain Protein", Science, Dec. 20, 2002, vol. 298, pp. 2401-2403.
Karala, A.-R., et al., "Modulation of an Active-Site Cysteine pKa Allows PDI to Act as a Catalyst of both Disulfide Bond Formation and Isomerization", J. Mol. Biol., 2010, vol. 396, pp. 883-892.
Kathayat, R.S., et al., "A Fluorescent Probe for Cysteine Depalmitoylation Reveals Dynamic APT Signaling", Nat. Chem. Biol., Feb. 2017, vol. 13(2), pp. 150-152.
Lasecka, L., et al., "The Nairovirus Nairobi Sheep Disease Virus/ Ganjam Virus Induces the Translocation of Protein Disulphide Isomerase-Like Oxidoreductases from the Endoplasmic Reticulum to the Cell Surface and the Extracellular Space", PLoS ONE, Apr. 2014, vol. 9(4), e94656, pp. 1-15.
Lee, H., et al., "Molecularly Self-Assembled Nucleic Acid Nanoparticles for Targeted In Vivo siRNA Delivery", Nat. Nanotechnol., 2012, vol. 7(6), pp. 389-393.
Lee, M.H., et al., "Hepatocyte-Targeting Single Galactose-Appended Naphthalimide: A Tool for Intracellular Thiol Imaging in Vivo", J. Am. Chem. Soc., 2012, vol. 134, pp. 1316-1322.
Li, J., et al., "Substrate Optimization for Monitoring Cathepsin C Activity in Live Cells", Bioorg. Med. Chem., 2009, vol. 17, pp. 1064-1070.
Linder, M.E., et al., "Palmitoylation: Policing Protein Stability and Traffic", Nat. Rev. Mol. Cell. Biol., Jan. 2007, vol. 8(1), pp. 74-84.
Liu, C., et al., "Eradication of Large Colon Tumor Xenografts by Targeted Delivery of Maytansinoids", Proc. Natl. Acad. Sci., USA, Aug. 1996, vol. 93, pp. 8618-8623.
Liu, J., et al., "Functional Nucleic Acid Sensors", Chem. Rev., 2009, vol. 109, pp. 1948-1998.
Lloyd, J.B., "Disulphide Reduction in Lysosomes. The Role of Cysteine", Biochem. J., 1986, vol. 237, pp. 271-272.
Los, G.V., et al., "HaloTag: A Novel Protein Labeling Technology for Cell Imaging and Protein Analysis", ACS Chem. Biol., 2008, vol. 3(6), pp. 373-382.
Maiti, S., et al., "Gemcitabine-Coumarin-Biotin Conjugates: A Target Specific Theranostic Anticancer Prodrug", J. Am. Chem. Soc., 2013, vol. 135, pp. 4567-4572.
Mills, J.E., et al., "A Novel Disulfide Bond in the SH2 Domain of the C-Terminal Src Kinase Controls Catalytic Activity", J. Mol. Biol., Feb. 2, 2007, vol. 365(5), pp. 1460-1468.
Modi, S., et al., "A DNA Nanomachine that Maps Spatial and Temporal pH Changes Inside Living Cells", Nat. Nanotechnol., May 2009, vol. 4(5), pp. 325-330 (Abstract only).
Mok, H., et al., "Multimeric Small Interfering Ribonucleic Acid for Highly Efficient Sequence-Specific Gene Silencing", Nat. Mater., Jan. 24, 2010, vol. 9, pp. 272-278.
Molla, M.R., et al., "Exploring Versatile Sulfhydryl Chemistry in the Chain End of a Synthetic Polylactide", Macromolecules, Oct. 2012, vol. 45, pp. 8561-8570.
Mugherli, L., et al., "Fluorogenic Ester Substrates to Assess Proteolytic Activity", Bioorg. Med. Chem. Lett., 2006, vol. 16, pp. 4488-4491.
Nicolau, C., et al., "Liposome-Mediated Dna Transfer in Eukaryotic Cells. Dependence of the Transfer Efficiency Upon the Type of Liposomes Used and the Host Cell Cycle Stage", Biochem. Biophys. Acta, 1982, vol. 721, pp. 185-190.
Pacello, F., et al., "An ERp57-Mediated Disulphide Exchange Promotes the Interaction Between Burkholderia cenocepacia and Epithelial Respiratory Cells", Sci. Rep., 2016, vol. 6, 21140, pp. 1-11.

(56) References Cited

OTHER PUBLICATIONS

Pires, M.M., et al., "Fluorescence Imaging of Cellular Glutathione Using a Latent Rhodamine", Org. Lett., 2008, vol. 10(5), pp. 837-840.

Presolski, S.I., et al., "Copper-Catalyzed Azide-Alkyne Click Chemistry for Bioconjugation", Curr. Protoc. Chem. Biol., 2011, vol. 3, pp. 153-162.

Prifti, E., et al., A Fluorogenic Probe for SNAP-Tagged Plasma Membrane Proteins Based on the Solvatochromic Molecule Nile Red, ACS Chem. Biol., 2014, vol. 9, pp. 606-612.

Rual, J.-F., et al., "Toward Improving Caenorhabditis elegans Phenome Mapping with an ORFeome-Based RNAi Library", Genome Res., 2004, vol. 14, pp. 2162-2168.

Brenner, S., "The Genetics of Caenorhabditis Elegans", Genetics, May 1974, vol. 77, pp. 71-94.

Collot, M., et al., "CaRuby-Nano: A Novel High Affinity Calcium Probe for Dual Color Imaging", eLife, 2015, vol. 4, e05808, pp. 1-18.

Grynkiewicz, et al., "A New Generation of Ca2+ Indicators with Greatly Improved Fluorescence Properties", J. Biol. Chem., 1985, vol. 260(6), pp. 3440-3450.

Halder, Saheli, et al., "Design of Ultrasensitive DNA-Based Fluorescent pH Sensitive Nanodevices", Nanoscale, May 20, 2015, vol. 7(22), pp. 10008-10012.

Halder, Saheli, et al., "Design of Ultrasensitive DNA-Based Fluorescent pH Sensitive Nanodevices", Electronic Supplementary Information (ESI) available: Materials and Methods, ESI Fig. 1-6, May 11, 2015, pp. 1-5.

Holzhüter, Katharina, "Spectroscopic Study of Natural and Unnatural Derivatives of the pH-Responsive Cytosine-Rich Human Telomeric DNA for Nanodevice Insight", Bachelor Thesis—Submitted to Department 14 (Chemistry, Biochemistry, Pharmacy) of the Johann-Wolfgang-von-Goethe University, Jun. 1, 2013, pp. 1-88.

Nicolau, Claude, et al., "Liposomes as Carriers for In Vivo Gene Transfer and Expression", Methods in Enzymology, Gene, 1987, vol. 149, pp. 157-176.

Brooks, T.A., et al., "Making Sense of G-quadruplex and i-Motif Functions in Oncogene Promoters", FEBS Journal, Sep. 2010, vol. 277(17), pp. 3459-3469, doi:10.1111/j.1742-4658.2010.07759.x.

Bucek, P., et al., "Spectrometric Study of the Folding Process of i-Motif-Forming DNA Sequences Upstream of the c-kit Transcription Initiation Site", Analytica Chimica Acta, 2010, vol. 683, pp. 69-77, doi:10.1016/j.aca.2010.10.008.

Chen, Y., et al., "A DNA Nanomachine Based on a Duplex-Triplex Transition", Angew. Chem. Int. Ed., 2004, vol. 43, pp. 5335-5338, doi:10.1002/anie.200460789.

Choi, J., et al., "pH-Induced Intramolecular Folding Dynamics of i-Motif DNA", J. Amer. Chem. Soc., 2011, vol. 133, pp. 16146-16153, doi:10.1021/ja2061984.

Dailey, M.M., et al., "Resolution and Characterization of the Structural Polymorphism of a Single Quadruplex-Forming Sequence", Nucleic Acids Research, 2010, vol. 38(14), pp. 4877-4888, doi:10.1093/nar/gkq166.

Datta, B., et al., "Quadruplex Formation by a Guanine-Rich PNA Oligomer", J. Am. Chem. Soc., 2005, vol. 127, pp. 4199-4207.

Edwards, E.L., et al., "A•T and C•C+ Base Pairs Can Form Simultaneously in a Novel Multistranded DNA Complex", Biochemistry, 1990, vol. 29, pp. 828-836.

Gehring, K., et al., "A Tetrameric DNA Structure with Protonated Cytosine Cytosine Base Pairs", Nature, 1993, vol. 363, pp. 561-565.

Idili, A., et al., "Programmable pH-Triggered DNA Nanoswitches", J. Am. Chem. Soc., 2014, vol. 136, pp. 5836-5839, doi:10.1021/ja500619w.

Jin, R., et al., "Tetraplex Formation of a Guanine-Containing Nonameric DNA Fragment", Science, Oct. 26, 1990, vol. 250(4980), pp. 543-546.

Kanehara, H., et al., "Spectroscopic Evidence for the Formation of Four-Stranded Solution Structure of Oligodeoxycytidine Phosphorothioate", Biochemistry, 1997, vol. 36(7), pp. 1790-1797.

Kaushik, M. et al., "Calorimetric Unfolding of the Bimolecular and i-Motif Complexes of the Human Telomere Complementary Strand, d(C3TA2)4", Biophysical Chemistry, 2007, vol. 126, pp. 154-164, doi:10.1016/j.bpc.2006.05.031.

Krishnan, Y, et al., "Designer Nucleic Acids to Probe and Program the Cell", Trends in Cell Biol., Dec. 2012, vol. 22(12), pp. 624-633, doi:10.1016/j.tcb.2012.10.001.

Krishnan, Y., et al., "Nucleic Acid Based Molecular Devices", Angew. Chem. Int. Ed., 2011, vol. 50, pp. 3124-3156.

Leroy, J.L., et al., "Intramolecular Folding of a Fragment of the Cytosine-Rich Strand of Telomeric DNA into an i-Motif", Nucleic Acids Res., 1994, vol. 22(9), pp. 1600-1606.

Levitt, et al., "Fluorescence Lifetime and Polarization-Resolved Imaging in Cell Biology", Current Opinion in Biotechnology, Feb. 2009, vol. 20(1), pp. 28-36, doi:10.1016/j.copbio.2009.01.004, Epub Mar. 4, 2009. (Abstract only).

Lieblein, A.L., et al., "Optimizing the Kinetics and Thermodynamics of DNA i-Motif Folding", Chembiochem., 2013, vol. 14, pp. 1226-1230, doi:10.1002/cbic.201300284.

Liu, D., et al., "A Proton-Fuelled DNA Nanomachine", Angew. Chem. Int. Ed., 2003, vol. 42, pp. 5734-5736.

Liu, D., et al., "A Reversible pH-Driven DNA Nanoswitch Array", J. Am. Chem. Soc., 2006, vol. 128, pp. 2067-2071.

Liu, Z., et al., "Reporting Transient Molecular Events by DNA Strand Displacement", Chem. Commun., 2014, vol. 50, pp. 8239-8241, doi:10.1039/c4cc03291h.

Makhija, E., et al., "Probing Chromatin Structure and Dynamics Using Fluorescence Anisotropy Imaging", CRC Handbook, Imaging Biological Mechanics, 2014. (Abstract not available).

Malliavin, T.E., et al., "Stability of the I-motif Structure is Related to the Interactions between Phosphodiester Backbones", Biophysical Journal, Jun. 2003, vol. 84, pp. 3838-3847.

Meng, H., et al., "Photoelectric Conversion Switch Based on Quantum Dots with i-Motif DNA Scaffolds", Chem. Commun., 2009, pp. 2293-2295, doi:10.1039/b903325d.

Mergny, J.L., et al., "Intramolecular Folding of Pyrimidine Oligodeoxynucleotides into an i-DNA Motif", J. Am. Chem. Soc., 1995, vol. 117(35), pp. 8887-8898.

Modi, S., et al., "Recombinant Antibody Mediated Delivery of Organelle-Specific DNA pH Sensors Along Endocytic Pathways", Nanoscale, 2014, vol. 6, pp. 1144-1152, doi:10.1039/c3nr03769j.

Moody, E.M., et al., "Folding of a Stable DNA Motif Involves a Highly Cooperative Network of Interactions", J. Am. Chem. Soc., 2003, vol. 125, pp. 16285-16293.

Nesterova, I.V., et al., "Rational Design of Highly Responsive pH Sensors Based on DNA i-Motif", J. Am. Chem. Soc., 2014, vol. 136, pp. 8843-8846, doi:10.1021/ja501859w.

Pasternak, A., et al., "Modulation of i-Motif Thermodynamic Stability by the Introduction of UNA (Unlocked Nucleic Acid) Monomers", Bioorg. Med. Chem. Lett., 2011, vol. 21, pp. 752-755, doi:10.1016/j.bmcl.2010.11.106.

Pasternak, A., et al., "Unlocked Nucleic Acid—An RNA Modification with Broad Potential", Org. Biomol. Chem., 2011, vol. 9, pp. 3591-3597, doi:10.1039/c0ob01085e.

Perlikova, P., et al., "Unlocked Nucleic Acids with a Pyrene-Modified Uracil: Synthesis, Hybridization Studies, Fluorescent Properties and i-Motif Stability", Chembiochem., 2014, vol. 15, pp. 146-156, doi:10.1002/cbic.201300567.

Phan, A.T., et al., "Human Telomeric DNA: G-quadruplex, i-Motif and Watson-Crick Double Helix", Nucleic Acids Research, 2002, vol. 30(21), pp. 4618-4625.

Scaria, P.V., et al., "Quadruplex Structure of d(G3T4G3) Stabilized by K+ or Na+ is an Asymmetric Hairpin Dimer", Proc. Natl. Acad. Sci., USA, 1992, vol. 89, pp. 10336-10340.

Sharma, N.K., et al., "PNA C—C+ i-Motif: Superior Stability of PNA TC8 Tetraplexes Compared to DNA TC8 Tetraplexes at Low pH", Chem. Commun., 2005, pp. 4330-4332, doi:10.1039/b506870c.

Simonsson, T, et al., "A Nuclease Hypersensitive Element in the Human c-myc Promoter Adopts Several Distinct i-Tetraplex Structures", Biochem. and Biophys. Res. Commun., 2000, vol. 278(1), pp. 158-166, doi:10.1006/bbrc.2000.3783.

(56) References Cited

OTHER PUBLICATIONS

Zhou, J., et al., "Formation of i-Motif Structure at Neutral and Slightly Alkaline pH", Mol. BioSyst., 2010, vol. 6, pp. 580-586, doi:10.1039/b919600e.

Chakraborty, S., et al., "A Structural Map of OncomiR-1 at Single-Nucleotide Resolution", Nucleic Acids Res., published online Jul. 17, 2017, vol. 45(16), pp. 9694-9705.

Chakraborty, S., et al., "Pri-miR-17-92a Transcript Folds into a Tertiary Structure and Autoregulates its Processing", RNA, May 2012, vol. 18(5), pp. 1014-1028.

Chakraborty, S., et al., "The Poly dA Helix: A New Structural Motif for High-Performance DNA-Based Molecular Switches", Nucleic Acids Res., published online Mar. 11, 2009, vol. 37(9), pp. 2810-2817.

Dan, K., et al., "DNA Nanodevices Map Enzymatic Activity in Organelles", Nature Nanotechnology, Mar. 14, 2019, vol. 14(3), pp. 252-259.

Gavory, G, et al., "Structural Analysis of the Catalytic Core of Human Telomerase RNA by FRET and Molecular Modeling", Biochemistry, Nov. 7, 2006, vol. 45(44), pp. 13304-13311.

Ghosh, Y.K., et al., "Nature of Linkage between the Cationic Headgroup and Cholesteryl Skeleton Controls Gene Transfection Efficiency", FEBS Lett., May 19, 2000, vol. 473(3), pp. 341-344.

Bhattacharya, S., et al., "Membrane Formation from Oxyethylene Bearing Cationic Cholesterol Derivatives", Ind. J. Chem. B, Oct. 2001, vol. 40B, pp. 891-894.

Krishnan-Ghosh, Y., et al., "Dynamic Covalent Chemistry on Self-Templating Peptides: Formation of a Disulfide-Linked Beta-Hairpin Mimic", Angew. Chem. Int. Ed., May 16, 2003, vol. 42(19), pp. 2171-2173.

Leung, K.H., et al., "Dynamic RNA Nanotechnology Enters the CRISPR Toolbox", ACS Cent. Sci., Jun. 18, 2019, vol. 5(7), pp. 1111-1113.

Leung, K.H., et al., "A DNA Nanomachine Chemically Resolves Lysosomes in Live Cells", Nature Nanotechnology, Feb. 1, 2019, vol. 14(2), pp. 176-183.

Modi, S., et al., "The PNA-DNA Hybrid I-Motif: Implications for Sugar-Sugar Contacts in I-Motif Tetramerization", Nucleic Acids Res., published online Aug. 26, 2006, vol. 34(16), pp. 4354-4363.

Narayanaswamy, N. et al., "A pH-Correctable, DNA-Based Fluorescent Reporter for Organellar Calcium", Nature Methods, Jan. 2019, vol. 16(1), pp. 95-102.

Paul, A., et al., "Combining G-Quadruplex Targeting Motifs on a Single PNA Scaffold: A Hybrid (3+1) PNA-DNA Bimolecular Quadruplex", Chem. Eur. J., 2008, vol. 14(28), pp. 8682-8689.

Prakash, V., et al., "Rational Design of a Quantitative, pH-Insensitive, Nucleic Acid Based Fluorescent Chloride Reporter", Chemical Science, published online Dec. 1, 2015, vol. 7(3), pp. 1946-1953.

Salgado, E., et al., "Visualization of Ca2+ Loss from Rotavirus During Cell Entry", J. Virol., published online Sep. 26, 2018, vol. 92(24), e01327-18, pp. 1-19.

Surana, S., et al., "Designing DNA Nanodevices for Compatibility with the Immune System of Higher Organisms", Nature Nanotechnology, Sep. 2015, vol. 10(9), pp. 741-747.

Surana, S., et al., "A Method to Study In Vivo Stability of DNA Nanostructures", Methods, Nov. 2013, vol. 64 (1), pp. 94-100.

Veetil, A., et al., "Chemical Control Over Membrane-Initiated Steroid Signaling with a DNA Nanocapsule", Proc. Natl. Acad. Sci. U.S.A., Sep. 18, 2018, vol. 115(38), pp. 9432-9437.

\* cited by examiner

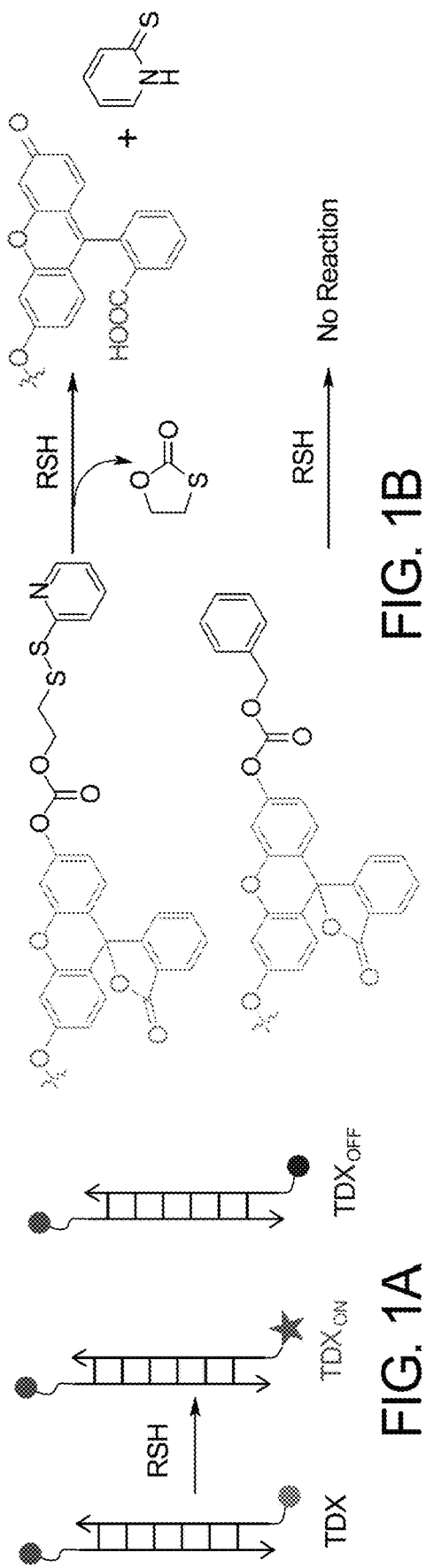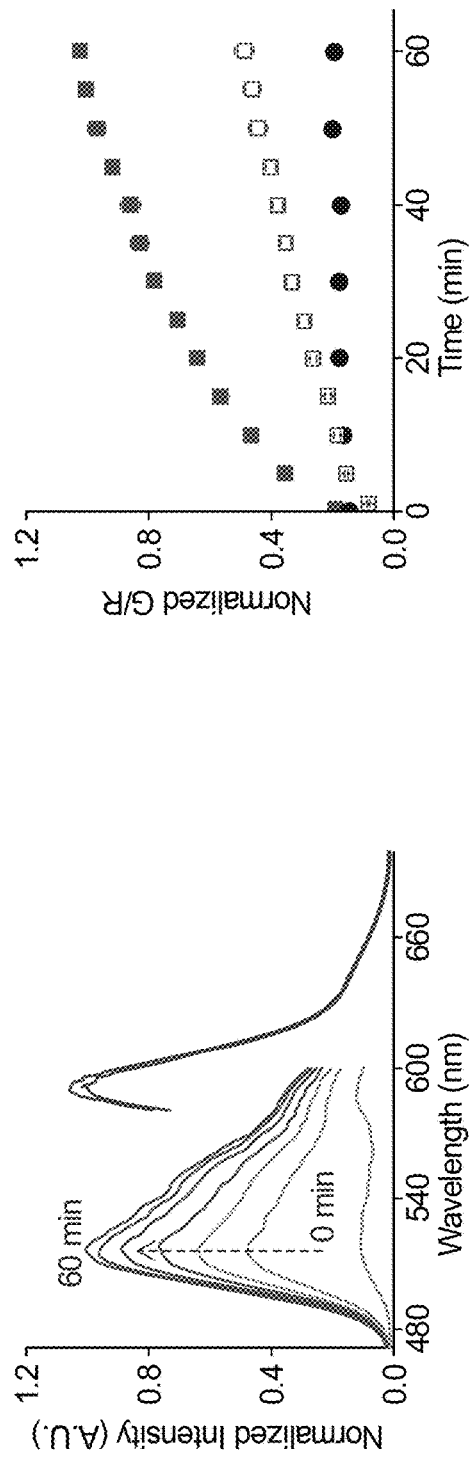
FIG. 1A
FIG. 1B
FIG. 1C
FIG. 1D

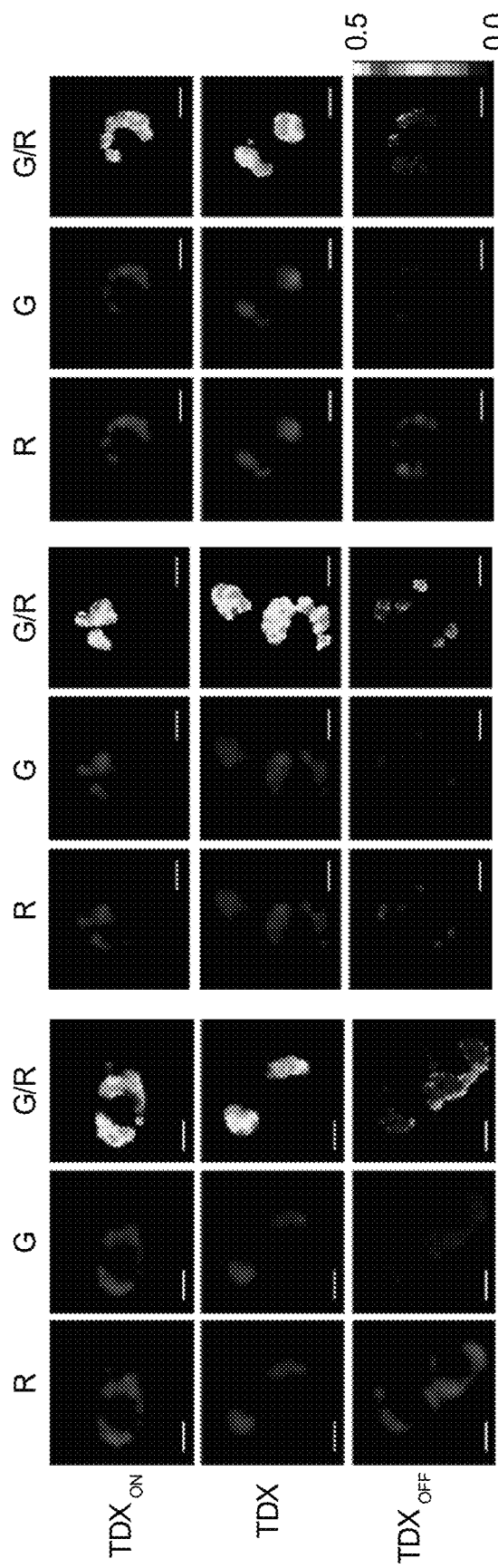
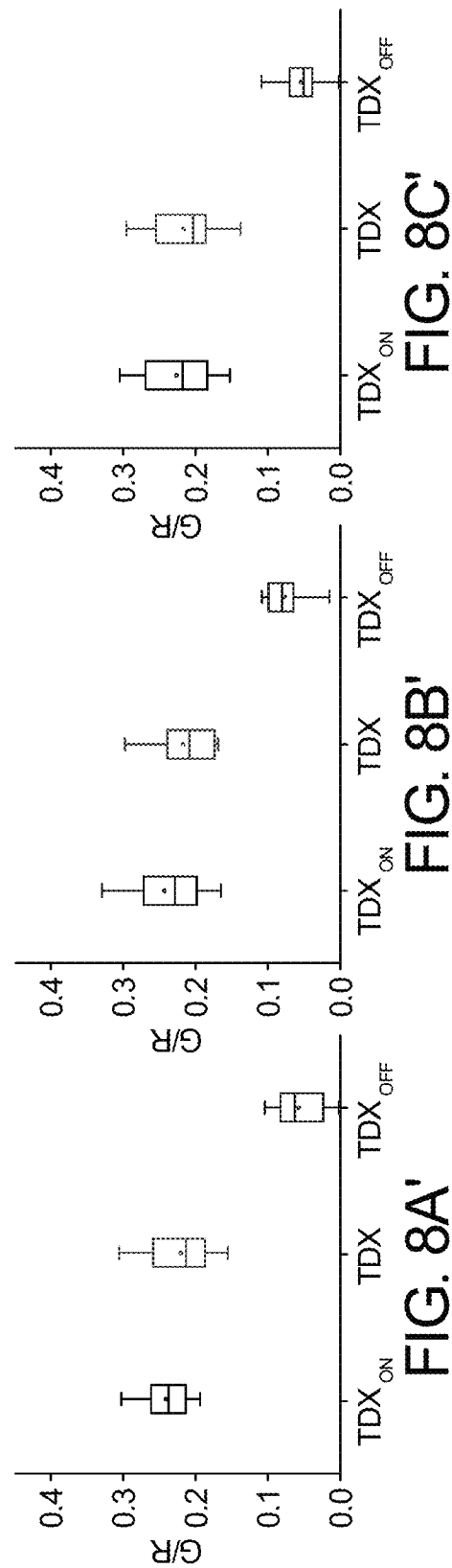
FIG. 8A  FIG. 8B  FIG. 8C
FIG. 8A'  FIG. 8B'  FIG. 8C'

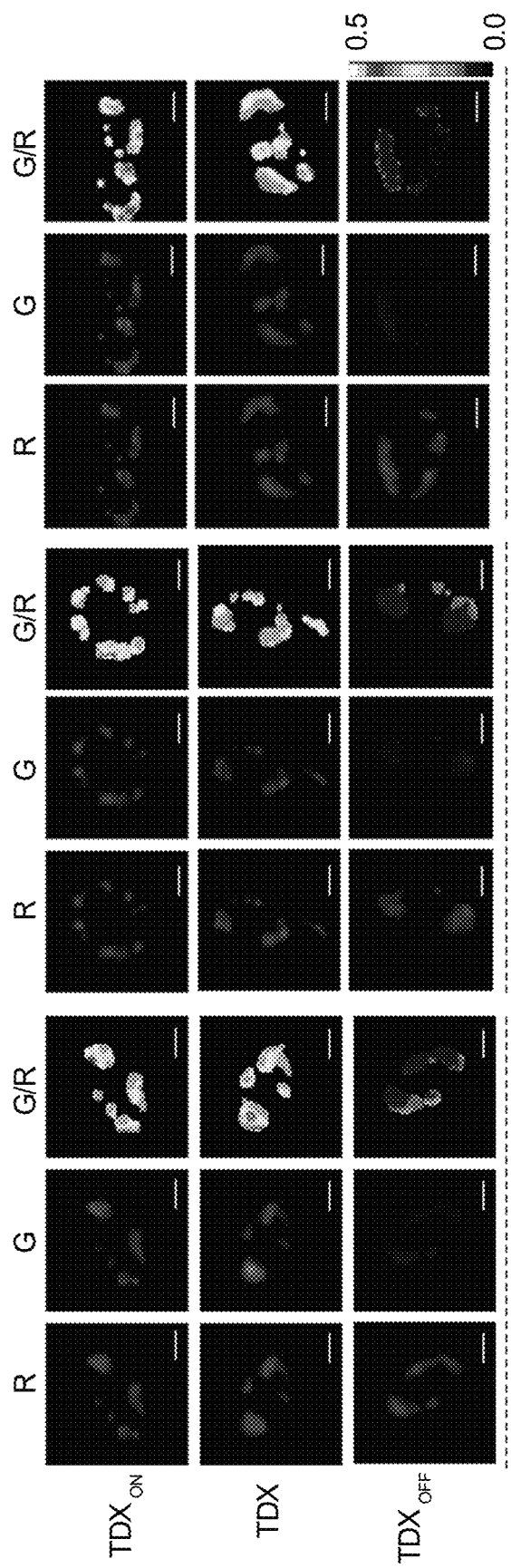
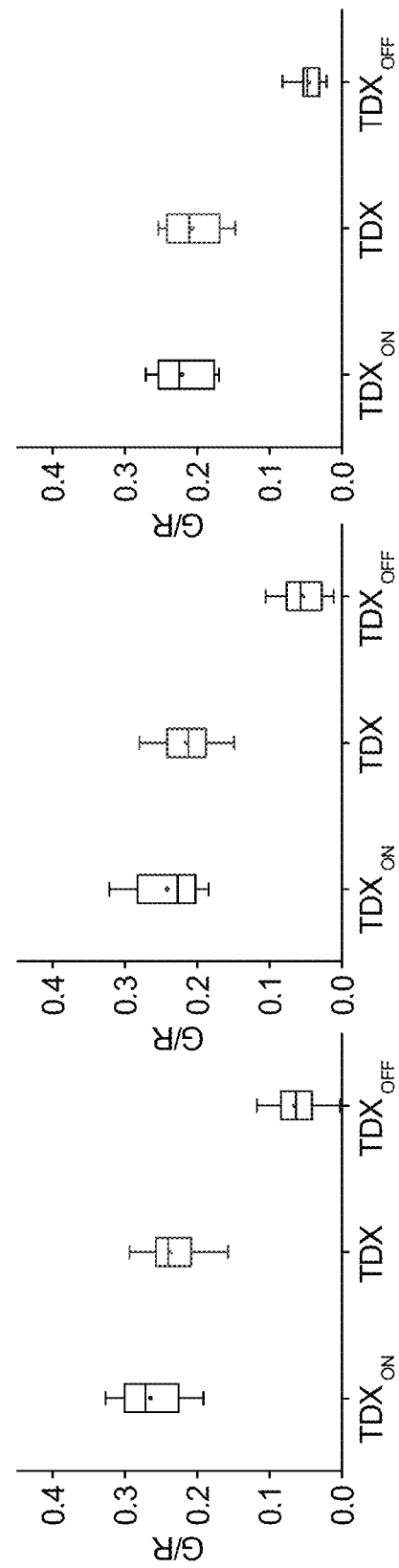
FIG. 8D  FIG. 8E  FIG. 8F
FIG. 8D'  FIG. 8E'  FIG. 8F'

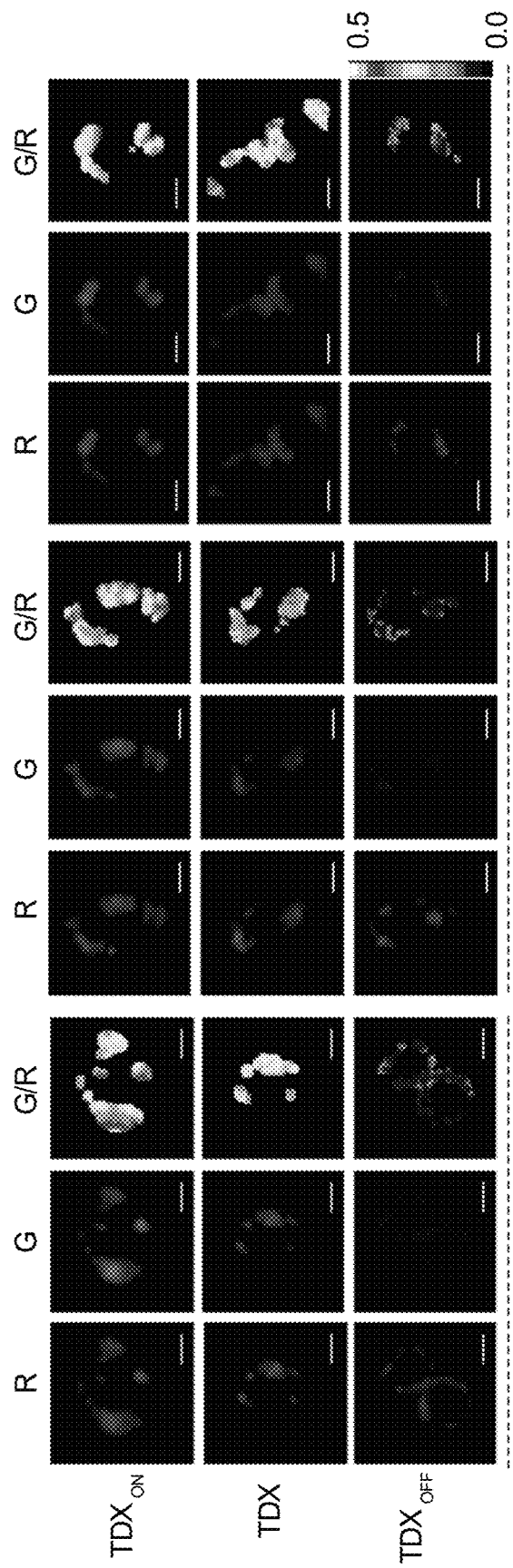
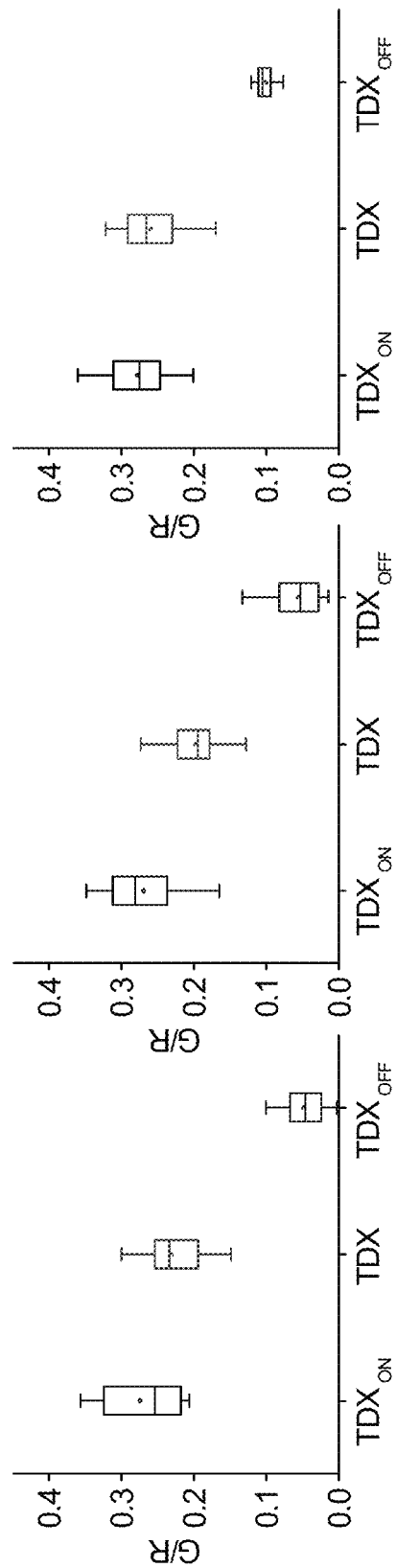

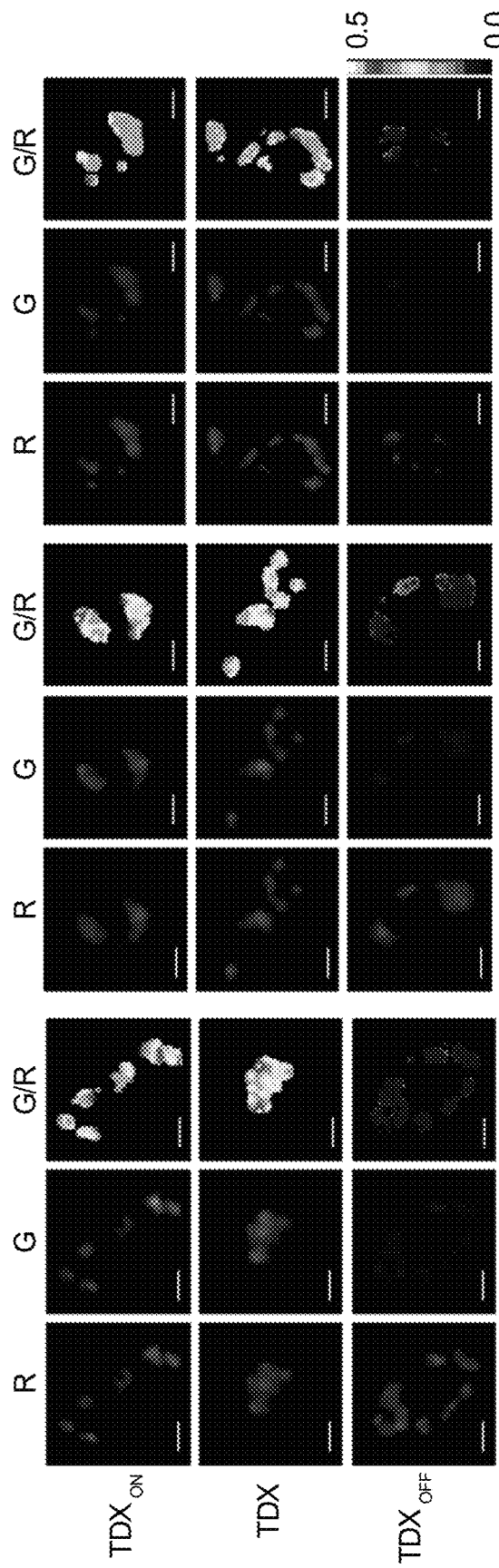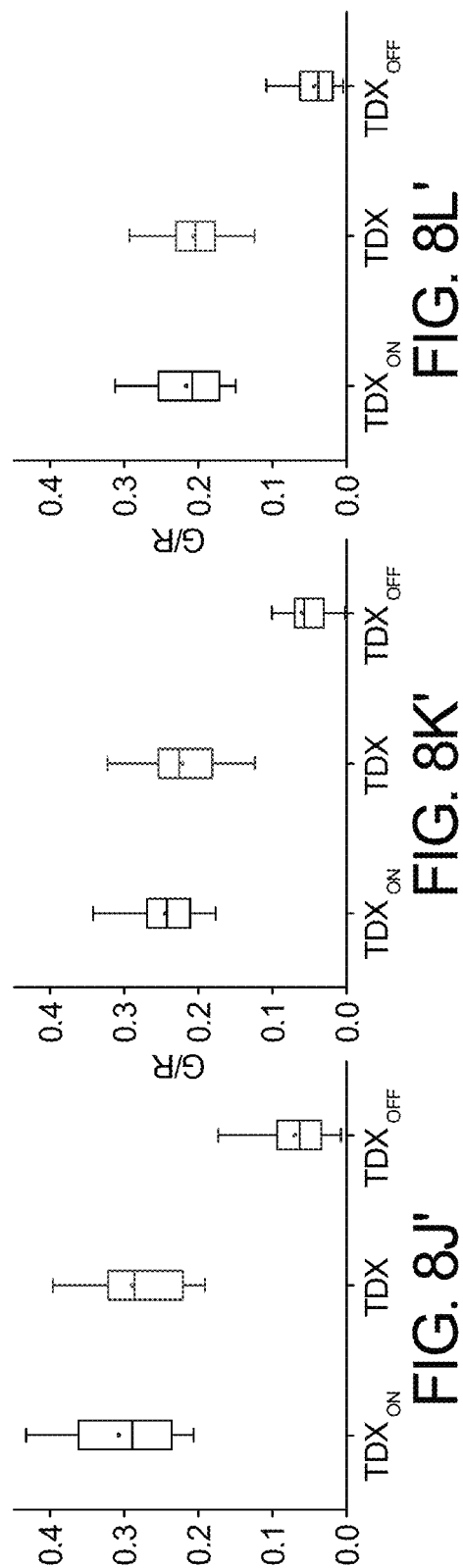
FIG. 8J  FIG. 8K  FIG. 8L
FIG. 8J' FIG. 8K' FIG. 8L'

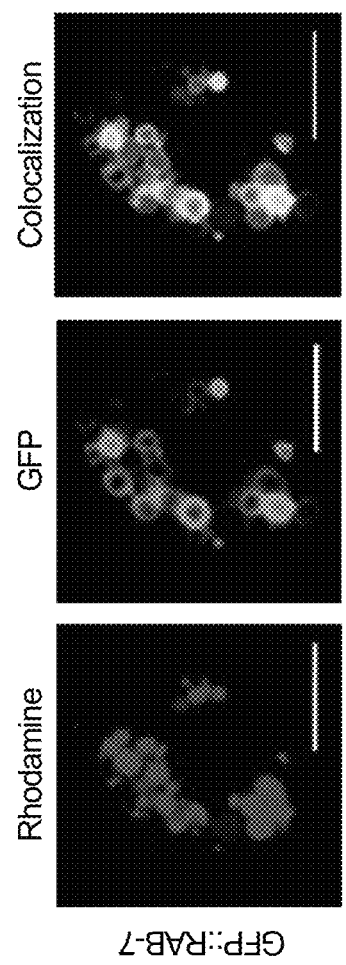
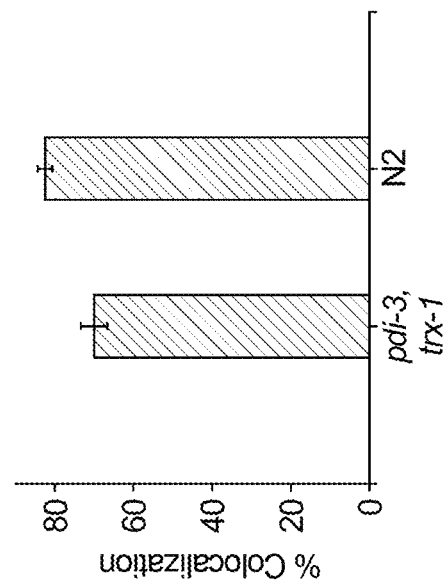
FIG. 9A
FIG. 9B

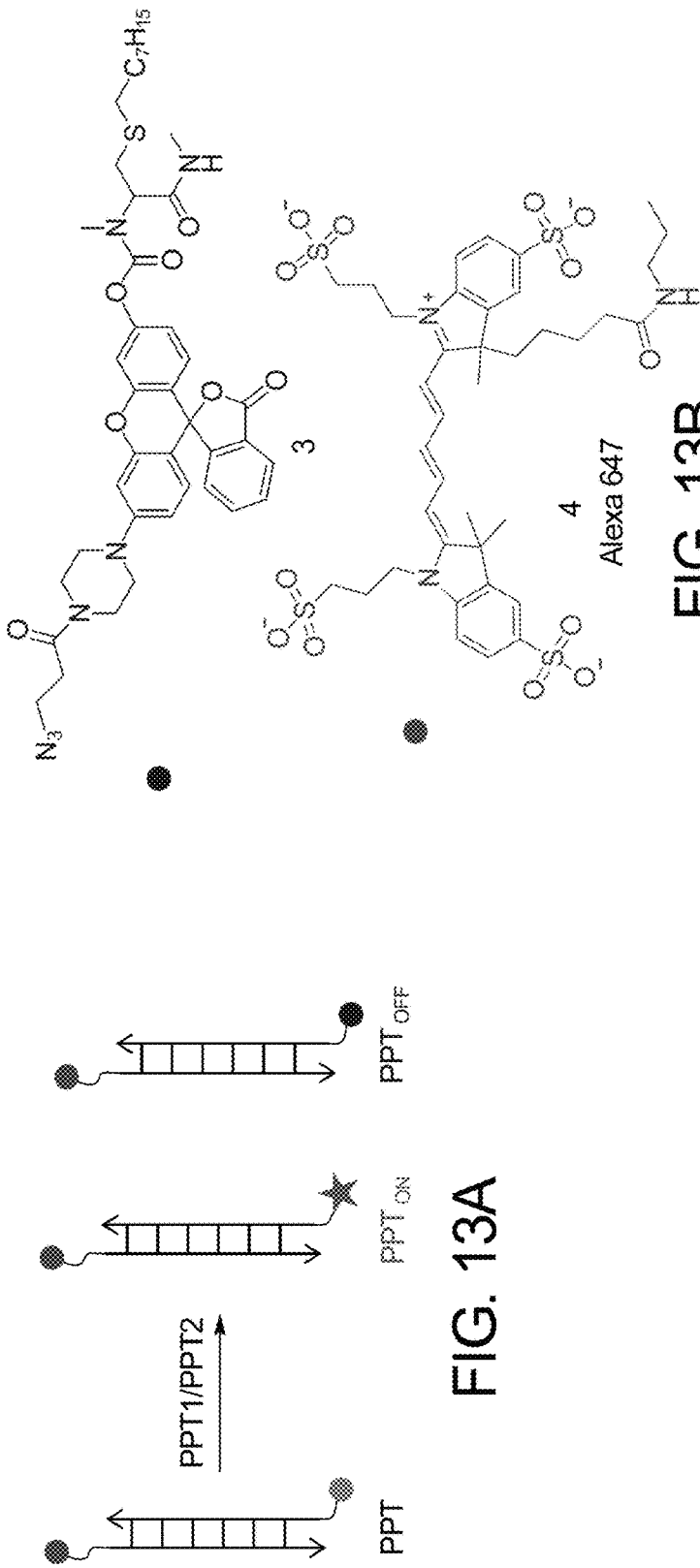
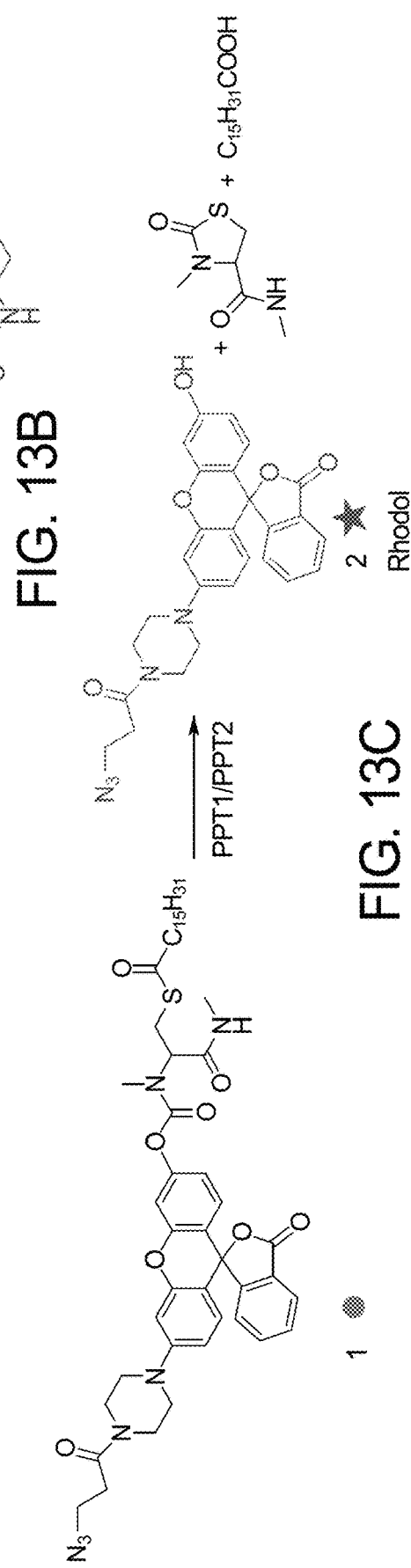
FIG. 13A
FIG. 13B
FIG. 13C

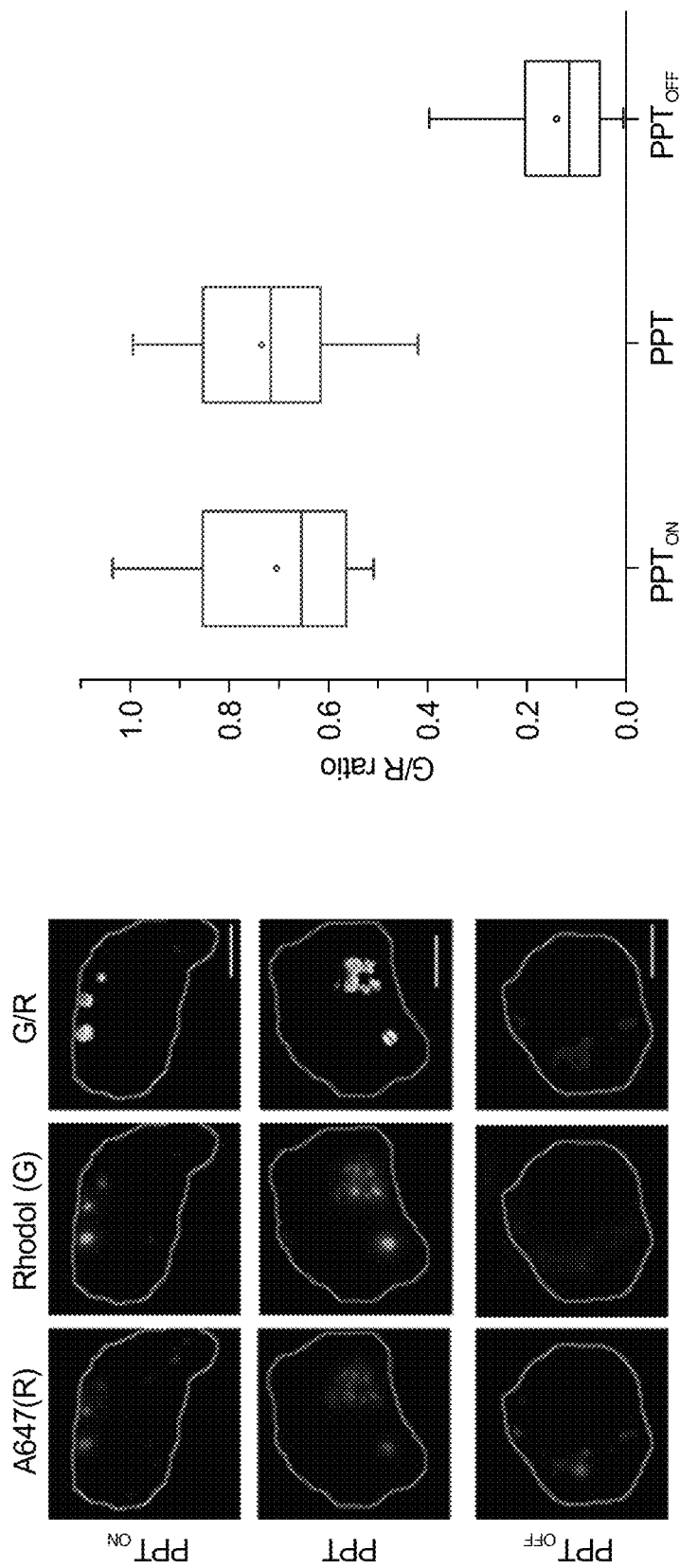

SEQUENCE LISTING

```
<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 1
atatatatgc cgactgctgc actgaccgca ggat                              34

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 2
atcctgcggt cagtgcagca gtcggcatat atat                              34

<210> SEQ ID NO 3
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Azide

<400> SEQUENCE: 3
atatatatgc cgactgctgc actgaccgca ggat                              34

<210> SEQ ID NO 4
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Rhodamine
```

```
<400> SEQUENCE: 4
atcctgcggt cagtgcagca gtcggcatat atat                               34

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
aattcggagt taagggattc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ttggtccatt ggatactttc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gaagccgcga aaagagagta                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
aagcaggctt caacttctcg                                               20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
cttcaaaaat gacacaatta cg                                            22

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gagaacgtcc tcgataaaat c                                             21

<210> SEQ ID NO 11
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
cttgctgata tgagtgactt tg                                    22

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
atacgtgctc caacactttt t                                     21
```

METHODS AND COMPOSITIONS FOR SPACIAL AND TEMPORAL MEASUREMENT OF CATALYTIC ACTIVITY

CROSS REFERENCE APPLICATIONS

This application is a 371 U.S. national phase of international application No. PCT/US2018/027391, claiming priority to U.S. Provisional Application 62/484,666 filed on Apr. 12, 2017, both of which are incorporated by reference in its entirety.

GOVERNMENT LICENSE RIGHTS

This invention was made with government support under DMR-1420709 awarded by the National Science Foundation. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on May 13, 2022 having the file name "19-347-WO-US_Sequence-Listing_ST25.txt" and is 3 kb in size.

FIELD OF THE INVENTION

Embodiments are directed generally to biology, medicine, and biotechnology.

BACKGROUND

The inability to image enzymatic function in real time in living systems presents a major challenge in the study of cell signalling. It is even more challenging to directly visualize enzymatic activity corresponding to a minor protein population that is responsible for a specific cellular function. In this regard, thiol-disulphide exchange presents a particular challenge because although disulphide reduction occurs within organelles, it is non-trivial to deconvolute from background cytosolic reduction.

Thiol disulphide exchange is crucial for cell physiology and cell survival. In the cytosol and in the endoplasmic reticulum, the correct folding of proteins stabilized by disulphide bonds critically depends on efficient thiol-disulphide exchange. Disulphide reduction of specific proteins changes protein conformation that in turn triggers important signalling cascades. For example, disulfide reduction of pentameric C reactive protein to its monomeric form activates endothelial cells, and disulfide reduction of C terminal SRC kinase results in kinase activation leading to cell proliferation and cancer. In organelles such as endosomes, thiol disulphide exchange is critical for degrading endocytosed cargo such as proteins and pathogenic material, mediating pathogen infection as well as antigen cross-presentation.

Recently, intra-endosomal disulphide reduction has assumed great importance because it is one of the most widely leveraged cellular chemistries for both drug and gene delivery. Disulphide reduction within endosomes is particularly challenging, since low endosomal pH impedes thiol-disulphide exchange. Consequently, the mechanism of intra-endosomal disulphide exchange is debated.

Accordingly, there is a need in the art to identify a universally applicable, quantitative reporter system for organellar thiol-disulphide exchange that could be used in a plug-and-play format across diverse endocytic pathways.

SUMMARY OF THE INVENTION

Described herein are nucleic acid molecules and complexes useful for spatiotemporally mapping intra-endosmal thiol disulphide exchange. Aspects of the disclosure relate to a composition comprising a first nucleic acid conjugated to a normalization moiety; and a second nucleic acid conjugated to a catalytic substrate; wherein reaction of the substrate with a catalyst produces a detectable product; and wherein the first and second nucleic acids are complementary or substantially complementary. Further aspects relate to a composition comprising: a first nucleic acid conjugated to a normalization moiety and to a catalytic substrate; and a second nucleic acid; wherein reaction of the substrate with a catalyst produces a detectable product; and wherein the first and second nucleic acids are complementary or substantially complementary.

The term "substrate" refers to a chemical species that can be converted to a product. In some embodiments, the substrate is an enzymatic substrate, which refers to a chemical species that is converted to a product by an enzyme and typically by binding to the active site of an enzyme. It is specifically contemplated that one or more substrates may be excluded in an embodiment. It is also specifically contemplated that one or more enzymes may be excluded in an embodiment.

In some embodiments, the first and second nucleic acids are in a duplex. It is well understood by those in the art that two complementary nucleic acids may exist in solution as a duplex or single-stranded. This depends, at least in part on the salt, pH, and temperature of the composition. In some embodiments, the normalization moiety and catalytic substrate are in a 1:1 ratio. In some embodiments, the detectable product is fluorescent. The detectable product may remain conjugated to the nucleic acid or may be released from the nucleic acid upon catalytic conversion. Suitable methods for conjugating detectable protected molecules to nucleic acids and to a relevant substrate are known in the art and described herein. The term "protected" as used herein refers to a modification to a detectable moiety that reduces or eliminates its detectable properties (e.g., fluorescence). The protection may be released by catalytic conversion of the substrate, thus increasing or exposing the detectable element, such as fluorescence.

In some embodiments, the catalytic substrate comprises a disulfide bond. In some embodiments, the catalytic substrate comprises is a thioester moiety. In some embodiments the catalytic substrate comprises the dipeptide Gly-Phe. In some embodiments, the catalytic substrate comprises Cbz-Phe-Lys. In some embodiments, the catalytic substrate comprises a protected fluorophore. In some embodiments, the catalytic substrate is derived from 6'-O propargyl fluorescein. In some embodiments, the catalytic substrate comprises:

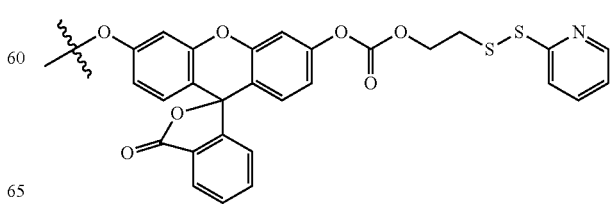

In some embodiments, the reaction comprises a thiol disulfide exchange. Thiol-disulfide exchange is a chemical reaction in which a thiolate group-S-attacks a sulfur atom of a disulfide bond —S—S—. The original disulfide bond is broken, and its other sulfur atom is released as a new thiolate, carrying away the negative charge. Meanwhile, a new disulfide bond forms between the attacking thiolate and the original sulfur atom.

In some embodiments, the normalization moiety and detectable product each comprise a fluorophore comprising an emission wavelength. In a related embodiment, the fluorophore of the normalization moiety and the fluorophore of the detectable product have different emission wavelengths. It is contemplated that a certain fluorophore and/or a certain emission wavelength may be excluded in an embodiment.

In some embodiments, the nucleic acid acts as a targeting nucleic acid. In some embodiments, the duplex nucleic acid acts as a targeting nucleic acid whereas the single-stranded nucleic acid exhibits a reduced amount of specificity for the target or exhibits substantially no specificity for the target. In some embodiments, the nucleic acid duplex directs a cell to localize the duplex to a specific organelle. In other embodiments, the nucleic acid is a targeting nucleic acid that is specific for a cell type, tissue type, or biochemical compartment described herein. In some embodiments, the nucleic acid duplex comprises an aptamer that directs a cell to localize the duplex to a specific organelle. In some embodiments, the nucleic acid duplex directs a cell to localize the duplex to the endosome. It is contemplated that compositions and methods involve cells but it is also contemplated that a cell may be mimicked in vitro such that an entire cell is not used in an embodiment.

Further aspects relate to a kit comprising a composition of the disclosure. The kit may also comprise additional reagents that can be used to serve as control for background detection (i.e. fluorescence) or as a positive control. For example, the kit may also comprise a composition comprising a first nucleic acid conjugated to a normalization moiety; and a third nucleic acid conjugated to a background correction moiety, wherein reaction of the background correction moiety with the catalyst does not produce a detectable product and wherein the third nucleic acid is complementary to the first nucleic acid. In some embodiments, the catalytic substrate comprises a disulfide bond and the background correction moiety lacks a disulfide bond. In some embodiments, the first and third nucleic acids are in a duplex. In some embodiments, the normalization moiety and background correction moiety are in a 1:1 ratio. In some embodiments, the background protection moiety comprises a protected fluorophore.

In some embodiments, the kit further comprises a composition comprising: a first nucleic acid conjugated to a normalization moiety; and a fourth nucleic acid conjugated to a detectable positive control moiety; wherein the fourth nucleic acid is complementary to the first nucleic acid. In some embodiments, the first and fourth nucleic acid are in a duplex. In some embodiments, the normalization moiety and the detectable positive control moiety are in a 1:1 ratio in the duplex. In some embodiments, the normalization moiety and the detectable positive control moiety each comprise a fluorophore comprising an emission wavelength. In some embodiments, the emission wavelength of the fluorophore of the normalization moiety and the fluorophore of the detectable positive control moiety are different emission wavelengths. In some embodiments, the kit further comprises instructions for use. In some embodiments, the detectable positive control moiety and the detectable product moiety each comprise a fluorophore; and wherein the fluorophore for the detectable positive control moiety and the detectable product moiety emit fluorescence at the same wavelength and/or are the same fluorophore. In some embodiments, the second, third, and/or fourth nucleic acid comprise the same nucleic acid sequence. In other embodiments, the first, second, third, and/or fourth nucleic acid may comprise the same sequence or a complimentary sequence to the first, second, third, and/or fourth nucleic acid. In some embodiments, the first, second, third, and/or fourth nucleic acid may comprise sequences that are not the same or that are not complementary to the first, second, third, and/or fourth nucleic acid sequence.

The nucleic acids of the disclosure may be at least, at most, or equal to 5, 6, 7, 8, 9, 10, 11, 12, 13, 14, 15, 20, 25, 30, 35, 40, 45, 50, 60, 70, 80, 90, 100, 125, 150, or 200 nucleic acids in length (or any derivable range therein). The nucleic acid may include DNA, RNA, or modified nucleic acids known in the art such as locked nucleic acids (LNA), 2-aminopurine-modified bases, 2,6-diaminopurine, 5-bromo dU, deoxyuridine, inverted dT, inverted dideoxy-T, dideoxy C, 5-methyl dC, deoxyinosine, 5-hydroxybutynl-2'-deoxyuridine, 8-aza-7-deazaguanosine, 5-nitroindole, 2'-O-methyl RNA bases, and hydroxmethyl dC. A nucleic acid molecule may comprise a combination of such modifications, such as LNA at the N- or C-terminal end of a nucleic acid molecule. One of skill in the art will understand that the nucleic acids and associated duplexes described herein need not be made from DNA, but could be made from another natural or unnatural analogue that is bound by the relevant target (e.g., cell receptor).

Further aspects of the disclosure relate to a method for detecting catalytic activity in a biological compartment comprising administering to a first population of at least one cell a composition of the disclosure comprising a catalytic substrate to allow for the substrate and catalyst to react to form the detectable product; detecting the product; and detecting the normalization moiety. In some embodiments, the detectable product and the normalization moiety each comprise a fluorophore comprising an emission intensity at a first (P) and second (N) wavelength, respectively; and wherein the method further comprises determining a normalized value for the detectable product, wherein the normalized value of the product (X) is the ratio of P/N.

In some embodiments, the method further comprises performing a background correction, wherein the background correction is performed by administering to a second population of at least one cell a composition comprising: a first nucleic acid conjugated to a normalization moiety; and a third nucleic acid conjugated to a background correction moiety, wherein reaction of the background correction moiety with the catalyst does not produce a detectable product and wherein the third nucleic acid is complementary to the first nucleic acid; detecting the emission intensity at the first (P') and second (N') wavelength from the second population of at least one cell; calculating the normalized value of the background correction (Y); wherein Y is the ratio of P'/N' from the second population of at least one cell; and subtracting Y from X to obtain a value for the background-corrected product intensity (Z). Therefore, the background correction can be determined according to the following formula: Z=X−Y where X=P/N and Y=P'/N' or Z=(P/N)−(P'/N').

In some embodiments, the catalytic substrate comprises a disulfide bond and the background correction moiety lacks a disulfide bond. In some embodiments, the first and third nucleic acid are in a duplex. In some embodiments, the normalization moiety and background correction moiety are in a 1:1 ratio. In certain embodiments, a catalytic substrate that does not have a disulfide bond is used.

In some embodiments or the method, compositions, and kits of the disclosure, the ratio of the normalization moiety to any of: the catalytic substrate, the background correction moiety, or the positive control moiety is at least, at most, or exactly 0.2:1, 0.5:1, 0.75:1, 1:1, 1:1.5, 1:2, 1:3, 1:4 or 1:5 (or any derivable range therein). In some embodiments, the background protection moiety comprises a protected fluorophore.

In some embodiments, the method further comprises calculating the background corrected total emission intensity (Z') comprising: administering to a third population of at least one cell a composition comprising: a first nucleic acid conjugated to a normalization moiety; and a fourth nucleic acid conjugated to a detectable positive control moiety; wherein the fourth nucleic acid is complementary to the first nucleic acid; detecting the emission intensity at the first (P''') and second (N''') wavelength from the third population of at least one cell; calculating the normalized value of the total emission intensity (X'); wherein X' is the ratio of P'''/N''' from the third population of at least one cell; and subtracting the normalized value of the background correction (Y) from the normalized value of the total emission intensity (X') to obtain the value for the background-corrected total emission intensity (Z'). Therefore, the background corrected total emission intensity can be calculated from the following: Z'=X'−Y wherein X'=P'''/N''' and Y=Y=P'/N' or Z'=(P'''/N''')−(P'/N').

In some embodiments, the first and fourth nucleic acid are in a duplex. In some embodiments, the normalization moiety and the detectable positive control moiety are in a 1:1 ratio in the duplex. In some embodiments, the normalization moiety and the detectable positive control moiety each comprise a fluorophore comprising an emission wavelength. In some embodiments, the emission wavelength of the fluorophore of the normalization moiety and the fluorophore of the detectable positive control are different emission wavelengths. In some embodiments, the method further comprises determining the fraction of emission intensity (A) of the detectable product; wherein the fraction of emission intensity of the detectable product is the ratio of Z/Z'. Therefore, the fraction of emission intensity can be calculated as A=Z/Z'. In some embodiments, the percent response is calculated (A'), wherein A'=A*100.

In some embodiments, the biological compartment is a cellular organelle. In a related embodiment, the cellular organelle comprises an endosome. In some embodiments, the biological compartment comprises a tissue, organelle, fluid or other biological compartment described herein. In some embodiments, the cellular organelle is an organelle that is not an endosome.

In some embodiments, the catalytic activity comprises thiol disulfide exchange. In some embodiments, the method comprises calculating the fraction of emission intensity (A) at two or more different time points. In some embodiments, the method comprises determining A, A', Z, Z', X, Y, P, P', P''', N,N', N''' at one or more time-points. In some embodiments, 1, 2, 3, 4, 5, 6, 7, 8, 9, 10, 12, 14, 16, 18, 20, or more (or any derivable range therein) time-points may be taken for a given parameter. The time-points may be at least about, at most about, or about 0.4, 1, 2, 5, 10, 20, 60 minutes or 1.5, 2, 2.5, 3, 4, 5, 6, 18, 12, 18, 24 hours, or 1.5, 2, 3, 4, 5, 6, 7, 8, 9, 10, 20, 30, 40 days apart (or any derivable range therein).

In some embodiments, the first, second and/or third populations of at least one cell are derived from a vertebrate. In some embodiments, the vertebrate is a human. In some embodiments, the second, third, and/or fourth nucleic acid have the same sequence. In certain embodiments, a nucleic acid sequence is a human sequence, meaning a human genome comprises that sequence.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-D shows the design and response of ratiometric reporters of disulphide exchange described in the Example 1.

FIG. 9A illustrates colocalization of GFP::RAB-7 with $TDX^R$ at 20 min post injection of pdi-3, trx-1 double RNAi worm. It confirms that the endosomal trafficking does not disturb due to knock down of these two gene by RNAi.

FIG. 9B illustrates percentage (%) colocalization of $TDX^R$ with pdi-3, trx-1 double RNAi worm and wild type (N2) worm at 20 min post injection. Scale bar=5 μm.

FIG. 13A-E shows the design and response of of the PPT probe for thio-esterase activity in endo-lysosomal compartment described in the Example 2.

DETAILED DESCRIPTION OF THE INVENTION

1. Compositions and Complexes

1.1 Targeting Nucleic Acids

Figure 2A:
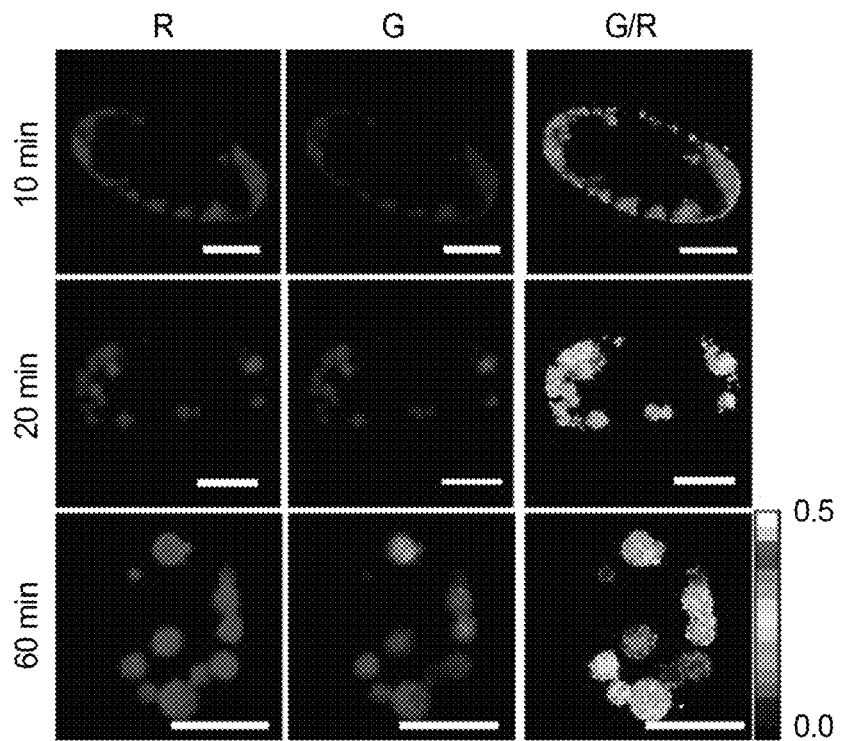
FIG. 2A-E describes the characterization and use of the TDX reporter system to measure thiol disulphide exchange described in the Example 1.

Compositions of the disclosure relate to nucleic acid conjugated to catalytic substrates and detectable labels. In certain embodiments, the nucleic acids are targeting nucleic acids and target the complex to a biological compartment. A "targeting nucleic acid" as used herein is a nucleic acid that has an affinity for a certain target or, by virtue of its chemical makeup, is targeted to a particular location in the cell. The targeting nucleic acid can act as a handle to target the nucleic acid complexes of the disclosure to different subcellular locations. The targeting nucleic acid may be a nucleic acid that specifically binds to a receptor protein, and the receptor protein may be one that is intracellularly targeted or conjugated to a protein that is specifically intracellularly targeted. The targeting nucleic acid or receptor protein may be a plasma membrane protein that is endocytosable, any proteins that possess a natural receptor, a protein that traffics between intracellular locations via the plasma membrane, toxins, viruses and viral coat proteins, cell penetrating peptides, signal sequences, intracellular targeting sequences, small organic molecules, endocytic ligands and trafficking proteins. In some embodiments, the targeting nucleic acid is an aptamer, a duplex domain targeted to an artificial protein receptor, a nucleic acid sequence that binds an anionic-ligand binding receptor, or an endocytic ligand. The targeting motif may also be a G4 core sequence or ribozyme.

As used, herein, a "biological compartment" includes: organs, tissues, extracellular matrices, organelles, cytosol, and biological fluids. Examples of organs include, but are not limited to, heart, lung, brain, eye, stomach, spleen, bone, pancreas, kidney, liver, intestine, skin, urinary bladder, ovary, uterus and testicle. Examples of tissues include, but are not limited to, epithelial tissue, connective tissue (which includes blood, bone and cartilage), muscle tissue and nervous tissue. Examples of extracellular matrices include, but are not limited to, the interstitial matrix and the basement membrane. Examples of organelles include, but are not limited to, the mitochondria, the Golgi apparatus, endoplasmic reticulum, endosomes, exosomes, chloroplasts, vacuoles, an endocytic vesicle, lysosomes, peroxisomes, vacuoles, microsomes, plasma membrane and nucleus. Examples of biological fluids include, but are not limited to, allantoic, amniotic, bronchioalveolar, cerebrospinal, intracranial, interluminal, extracellular, extravascular, interstitial, intraocular, lymph, pleural and synovial.

Targeting nucleic acids and methods of making targeting nucleic acids are known in the art. In some embodiments, the targeting nucleic acid is an endosome-specific nucleic acid. In some embodiments, the endosome-specific nucleic acid (i.e. the first, second, third, or fourth nucleic acid) comprises the following sequence: 5-AT ATA TAT GCC GAC TGC TGC ACT GAC CGC AGG AT-3' (SEQ ID NO:1). In some embodiments, the first, second, third, or fourth nucleic acid comprises the following endosome-specific nucleic acid: 5'-AT CCT GCG GTC AGT GCA GCA GTC GGC ATA TAT AT-3' (SEQ ID NO:2).

In some embodiments, the nucleic acids target the complex to the Golgi or endoplasmic reticulum. For example, the nucleic acid may comprise a signal sequence of Furin known in the art and described in WO2013054286A1, which is herein incorporated by reference. In some embodiments, the nucleic acids target the complex to a recycling endosome. For example, the nucleic acid may comprise a transferrin aptamer known in the art and described in WO2015159122, which is herein incorporated by reference.

In some embodiments, the nucleic acid is an aptamer that is specific for a biological compartment. The term "aptamers" as used here indicates oligonucleic acid molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Methods of making and identifying aptamers with specificity for a particular biological compartment are known in the art. For example, U.S. 20090081679 describes methods for making targeting nucleic acids with specificities for a particular biological compartment.

The first, second, third, and/or fourth nucleic acid may be complimentary to each other or substantially complementary to each other. Nucleic acid duplexes may have at least, at most, or exactly 1, 2, 3, 4, 5, 6, 7, 8, 9, or 10 mismatches (or any derivable range therein). The nucleic acids may also be at least, at most, or exactly 70, 75, 80, 85, 86, 87, 88, 89, 90, 91, 92, 93, 94, 95, 96, 97, 98, 99, or 100% (or any range derivable therein) identical to a nucleic acid described herein.

1.2 Detectable Moieties

The oligonucleotides and nucleic acid molecules in the compositions and methods described herein may include one or more detectable moiety. For example, the normalization moiety, detectable product, and positive control moiety all comprise a detectable moiety. The detectable moiety may be one known in the art or described herein. A "normalization moiety" as used herein is a a detectable moiety whose fluorescence properties are insensitive to the enzyme of interest's catalytic activity. In some embodiments, the normalization moiety is insensitive to lumenal ionic variations within endocytic organelles. In some embodiments, the normalization moieties for disulfide isomerase, thioesterase, and cathepsin activity comprise rhodamine, Alexa-647, and A647N, respectively. Nucleic acid molecules can be labeled by incorporating moieties detectable by one or more means including, but not limited to, spectroscopic, photochemical, biochemical, immunochemical, electrochemical or chemical assays. As used herein, "detectable moieties" are chemical or biochemical moieties useful for labeling a nucleic acid and include, for example, fluorescent agents, chemiluminescent agents, chromogenic agents, quenching agents, radionucleotides, enzymes, substrates, cofactors, inhibitors, nanoparticles, magnetic particles, and other moieties known in the art. The method of linking or conjugating the moiety to the nucleotide or oligonucleotide depends on the type of label(s) used and the position of the label on the nucleotide or oligonucleotide. Detectable moieties may be covalently or noncovalently joined to an oligonucleotide or nucleotide. It is specifically contemplated that one or more detectable moieties is excluded in an embodiment.

In some embodiments, the nucleic acid molecules may comprise a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy 7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18 (5)); DIDS; Dihydorhodamine 123 (DHR); DiI (DiIC18 (3)); Dinitrophenol; DiO (DiOC18 (3)); DiR; DiR (DiIC18 (7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold);

Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl) quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof. It is specifically contemplated that one or more dyes is excluded in an embodiment.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The detectable moieties can be conjugated to the nucleic acid molecules directly or indirectly by a variety of techniques. Depending upon the precise type of moiety used, the moiety can be located at the 5' or 3' end of the oligonucleotide, located internally in the oligonucleotide's nucleotide sequence, or attached to spacer arms extending from the oligonucleotide and having various sizes and compositions to facilitate signal interactions. Using commercially available phosphoramidite reagents, one can produce nucleic acid molecules containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Certain embodiments of the disclosure relate to protecting the detectable moiety. The term "protecting" as used herein refers to a modification of the detectable moiety that reduces or eliminates the detection of the moiety until the modification is removed or until the moiety is further modified to induce the detectable nature of the moiety. For example, fluorophores can be protected by conjugation to a carbonate linker. Examples are further described in S. Bhuniya et al., Angew Chem Int Ed Engl. 53, 4469-4474 (2014) and S. Maiti et al., J Am Chem Soc. 135, 4567-4572 (2013), which are herein incorporated by reference.

As described in the examples of the application, the detectable moiety may be protected and catalytic conversion of a reaction substrate attached to the moiety may result in deprotection of the moiety and detection of the molecule.

Furthermore, the background correction moiety may comprise a protected detectable moiety that cannot be or is inefficiently deprotected by a catalyst. In some embodiments, the background correction moiety and the detectable product comprise the same detectable moiety. In some embodiments, the background correction moiety and the positive control moiety comprise the same detectable moiety. In some embodiments, the detectable product and the positive control moiety comprise the same detectable moiety. In some embodiments, the positive control moiety, detectable product, and the background correction moiety comprise the same detectable moiety. In some embodiments, the background correction moiety and the detectable product comprise a different detectable moiety. In some embodiments, the background correction moiety and the positive control moiety comprise a different detectable moiety. In some embodiments, the detectable product and the positive control moiety comprise a different detectable moiety. In some embodiments, the positive control moiety, detectable product, and the background correction moiety comprise different detectable moieties.

Fluorescence in the sample can be measured in a variety of ways, such as using a fluorometer or fluorescence microscopy. In general, excitation radiation, from an excitation source having a first wavelength, passes through excitation optics. The excitation optics cause the excitation radiation to excite the sample. In response, fluorophores associated with the nucleic acids in the sample emit radiation which has a wavelength that is different from the excitation wavelength. Collection optics then collect the emission from the sample. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the detecting includes measuring the magnitude of the signal generated, wherein the magnitude indicates the amount of catalytic activity of the cell or region thereof. As used herein, the term "detectable" refers to a property of the moiety that allows one to determine the level of activity of a biological sample by detecting the moiety, e.g., fluorescence.

1.3 Introduction of Nucleic Acids into Cells

In some embodiments, the sample in which catalytic activity is detected can be a biological sample, e.g., a biological tissue or a cell or an organism. The method is suitable for measuring catalytic activity in a specific region of the cell, e.g., the cytosol, or an organellar space such as, but not limited to, the inner mitochondrial matrix, the lumen of the Golgi, the endoplasmic reticulum, the chloroplast lumen, the lumen of a lysosome, the nucleus, or the lumen of an endosome.

The nucleic acid molecules described herein can be readily introduced into a host cell, e.g., a mammalian (optionally human), bacterial, parasite, yeast or insect cell by any method in the art. For example, nucleic acids can be transferred into a host cell by physical, chemical or biological means. It is readily understood that the introduction of the nucleic acid molecules yields a cell in which the intracellular catalytic activity may be measured. Thus, the method can be used to measure intracellular catalytic activity in cells cultured in vitro. The compositions can also be readily introduced into a whole organism to measure the catalytic activity in a cell or tissue in vivo. For example, the nucleic acid compositions and complexes of the disclosure can be transferred into an organism by physical, chemical or biological means, e.g., direct injection.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York, 2001), and in Ausubel et al. (Current Protocols in Molecular Biology, John Wiley & Sons, New York, 1997).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the polynucleotide into host cells (in vitro, ex vivo or in vivo). In some embodiments, the nucleic acid complex may be associated with a lipid. The nucleic acid complex associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid/nucleic acid compositions are not limited to any particular structure in solution. For example, they may be present in a bilayer structure, as micelles, or with a "collapsed" structure. They may also simply be interspersed in a solution, possibly forming aggregates which are not uniform in either size or shape.

Liposome-mediated oligonucleotide delivery and expression of foreign DNA in vitro has been very successful. Wong et al. (*Gene* 10, 87-94, (1980)) demonstrated the feasibility of liposome-mediated delivery and expression of foreign DNA in cultured chick embryo, HeLa and hepatoma cells. Nicolau et al. (*Biochem. Biophys. Acta,* 721, 185-190, (1987)) accomplished successful liposome-mediated gene transfer in rats after intravenous injection.

2. Assay Methods

The compositions and nucleic acid molecules of the disclosure are useful for spacially and temporally detecting catalytic activity in a cell or organism. It is contemplated that any catalytic substrate can be used in the methods described herein. Described below are exemplary catalytic substrates useful in the methods of the disclosure:

2.1 Peptidases

The compositions and methods can be created using a reactive group, such as an amine, of the fluorophore. The following uses Rhodamine 110 as the fluorophore, but it is contemplated that any fluorophore may be used. The squiggle denotes attachment to the nucleic acid.

An exemplary positive control moiety includes the ON sensor below:

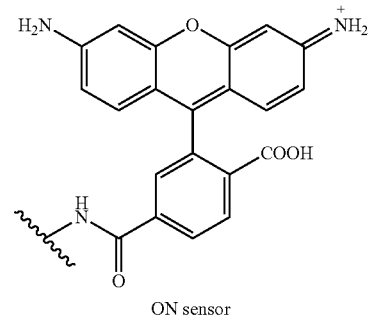 [SMILES: *NC(=O)c1ccc(C(=O)O)c(-c2c3ccc(=N)cc-3oc3cc(N)ccc23)c1]

ON sensor

An exemplary background correction moiety includes the OFF sensor below:

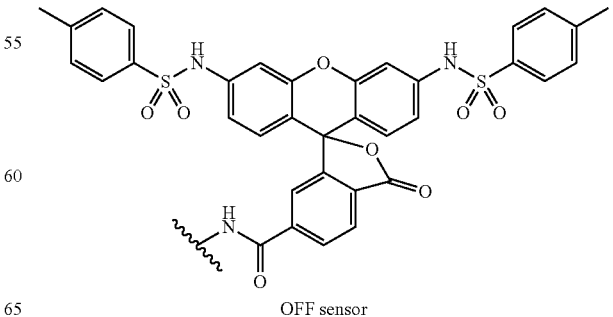

OFF sensor

An exemplary catalytic substrate to determine gly-phe peptidase activity includes:

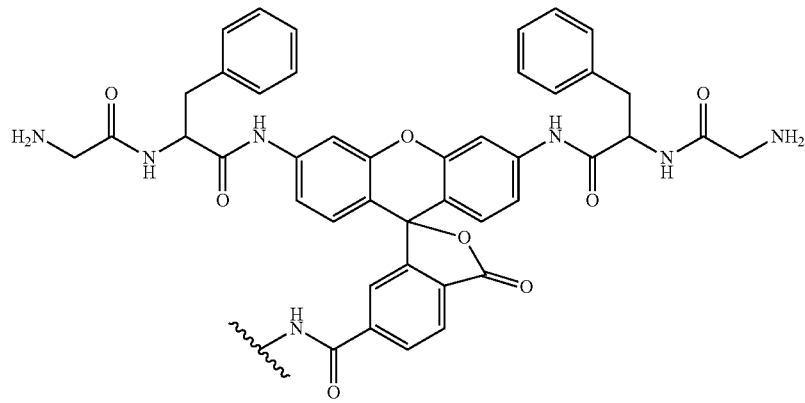 [SMILES: *NC(=O)c1ccc2c(c1)C1(OC2=O)c2ccc(NC(=O)C(Cc3ccccc3)NC(=O)CN)cc2Oc2cc(NC(=O)C(Cc3ccccc3)NC(=O)CN)ccc21]

In some embodiments, the method using the catalytic substrate above is for detecting gly-phe catalytic activity. In some embodiments, the method using the catalytic substrate above is for detecting enzymatic conversion of the substrate by the enzyme cathepsin C. In some embodiments, the method may be for detecting or diagnosing Papillon-Lefevre syndrome or for discovering modulators of this activity or disease phenotype.

The following catalytic moiety can be used to detect arg-arg peptidase activity. In some embodiments, the method using the catalytic substrate below is for detecting enzymatic conversion of the substrate by the enzyme cathepsin B:

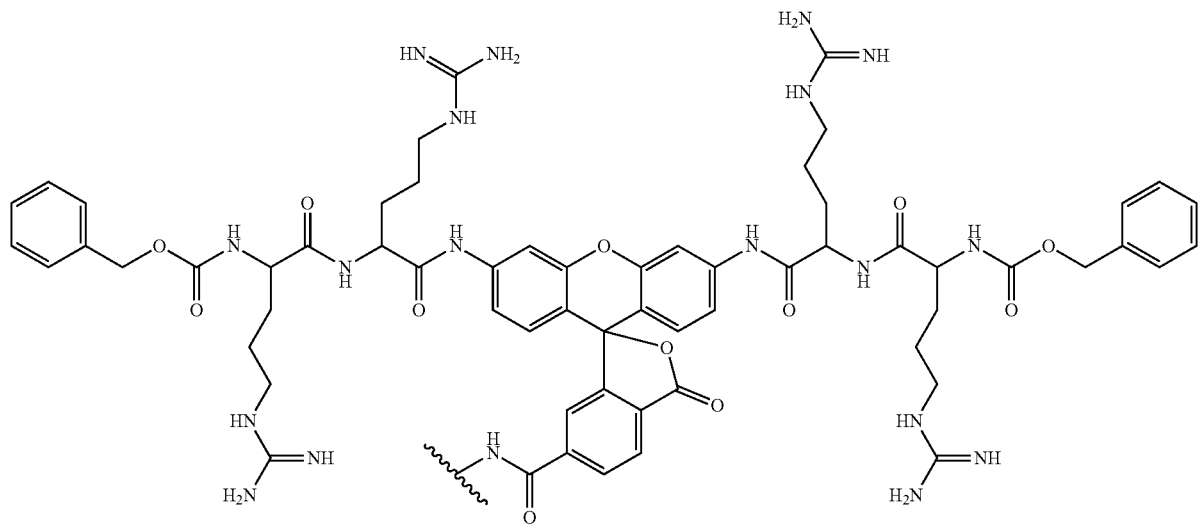 [SMILES: *NC(=O)c1ccc2c(c1)C1(OC2=O)c2ccc(NC(=O)C(CCCNC(=N)N)NC(=O)C(CCCNC(=N)N)NC(=O)OCc3ccccc3)cc2Oc2cc(NC(=O)C(CCCNC(=N)N)NC(=O)C(CCCNC(=N)N)NC(=O)OCc3ccccc3)ccc21]

The following catalytic moiety can be used to detect leu-arg peptidase activity. In some embodiments, the method using the catalytic substrate below is for detecting enzymatic conversion of the substrate by the enzyme cathepsin K. In some embodiments, the method may be for detecting or diagnosing pycnodysostosis or for discovering modulators of this activity or disease phenotype.

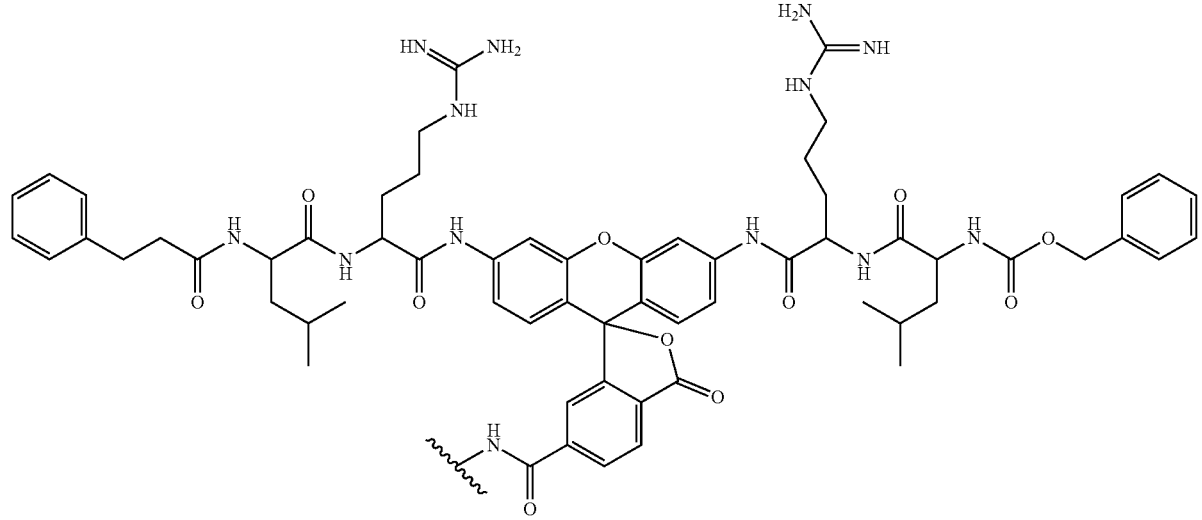 [SMILES: *NC(=O)c1ccc2c(c1)C1(OC2=O)c2ccc(NC(=O)C(CCCNC(=N)N)NC(=O)C(CC(C)C)NC(=O)CCc3ccccc3)cc2Oc2cc(NC(=O)C(CCCNC(=N)N)NC(=O)C(CC(C)C)NC(=O)OCc3ccccc3)ccc21]

The following catalytic moiety can be used to detect phe-arg peptidase activity. In some embodiments, the method using the catalytic substrate below is for detecting enzymatic conversion of the substrate by the enzyme cathepsin L:

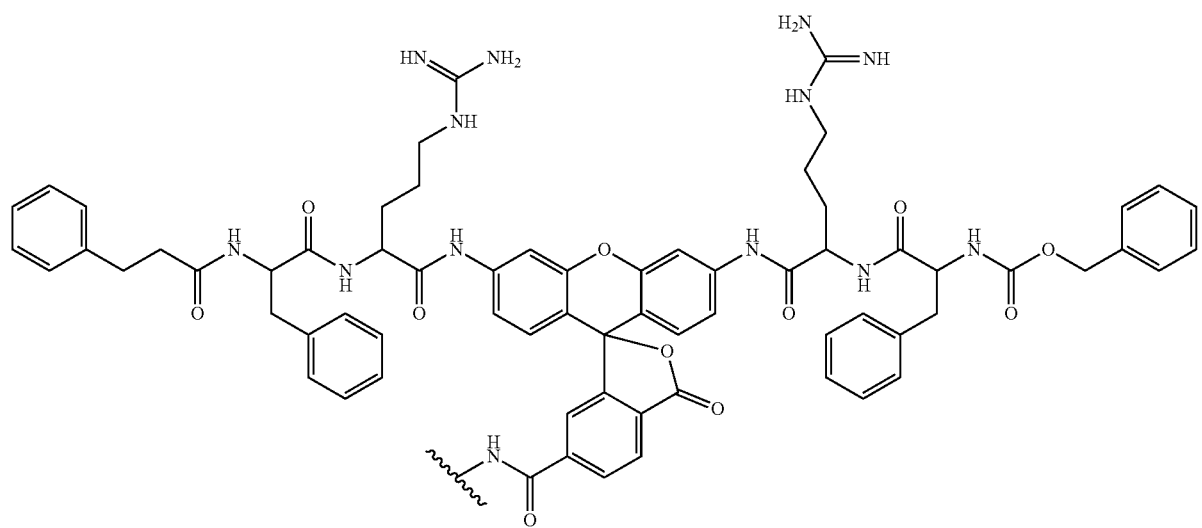 [SMILES: *NC(=O)c1ccc2c(c1)C1(OC2=O)c2ccc(NC(=O)C(CCCNC(=N)N)NC(=O)C(Cc3ccccc3)NC(=O)CCc3ccccc3)cc2Oc2cc(NC(=O)C(CCCNC(=N)N)NC(=O)C(Cc3ccccc3)NC(=O)OCc3ccccc3)ccc21]

The following catalytic moiety can be used to detect ala-ala-phe peptidase activity. In some embodiments, the method using the catalytic substrate below is for detecting enzymatic conversion of the substrate by the enzyme TPP1. In some embodiments, the method may be for detecting or diagnosing neuronal ceroid lipofuscinosis (NCL) or for discovering modulators of this activity or disease phenotype.

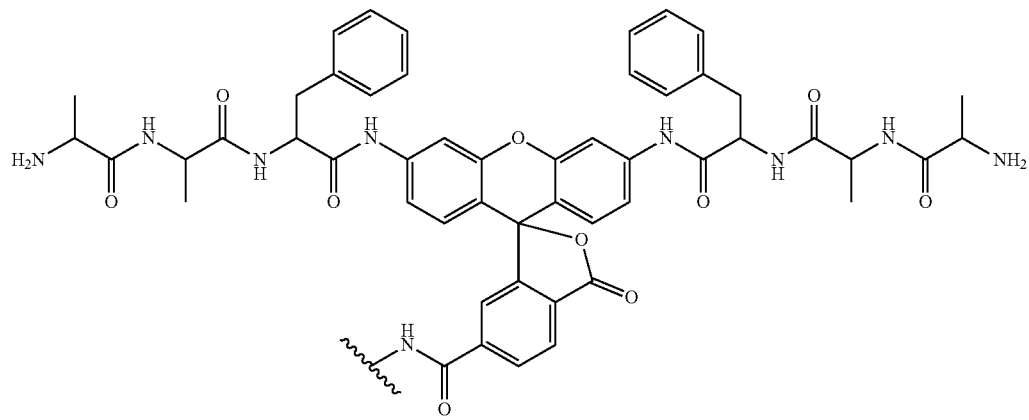 [SMILES: *NC(=O)c1ccc2c(c1)C1(OC2=O)c2ccc(NC(=O)C(Cc3ccccc3)NC(=O)C(C)NC(=O)C(C)N)cc2Oc2cc(NC(=O)C(Cc3ccccc3)NC(=O)C(C)NC(=O)C(C)N)ccc21]

2.2 Glucosidases

The moieties below are exemplary moieties for detection of glucosidase activity. The following moieties have been created using the oxygen of the fluorophore, fluorescein, to attach the catalytic substrate, but the methods may be easily adapted to other fluorophores and detectable molecules through the use of a reactive group on the detectable molecule. The squiggle in the structures below represents attachment to the nucleic acid.

An exemplary positive control moiety includes the following:

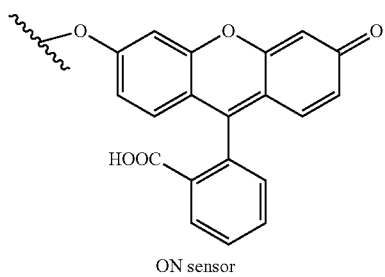 [SMILES: *Oc1ccc2c(-c3ccccc3C(=O)O)c3ccc(=O)cc-3oc2c1]

ON sensor

An exemplary background correction moiety includes the following:

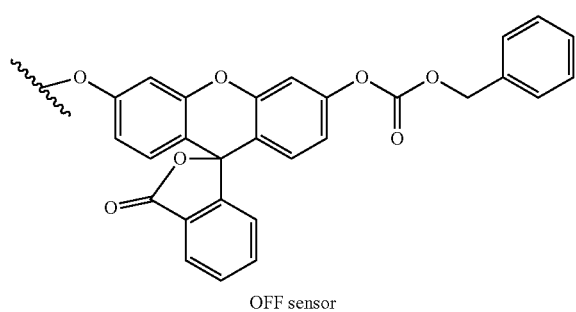 [SMILES: *Oc1ccc2c(c1)Oc1cc(OC(=O)OCc3ccccc3)ccc1C21OC(=O)c2ccccc21]

OFF sensor

The following catalytic moiety can be used to detect beta-glucosidase activity. In some embodiments, the method using the catalytic substrate below is for detecting enzymatic conversion of the substrate by a beta-glucosidase enzyme. In some embodiments, the method may be for detecting or diagnosing Gaucher disease or for discovering modulators of this activity or disease phenotype.

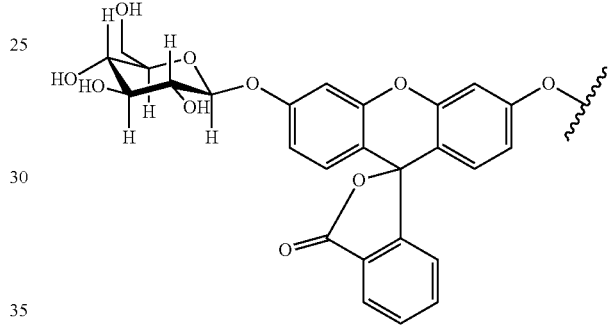

The following catalytic moiety can be used to detect beta-galactosidase activity. In some embodiments, the method using the catalytic substrate below is for detecting enzymatic conversion of the substrate by a beta-galactosidase enzyme. In some embodiments, the method may be for detecting or diagnosing GM1 gangliosidoses or for discovering modulators of this activity or disease phenotype.

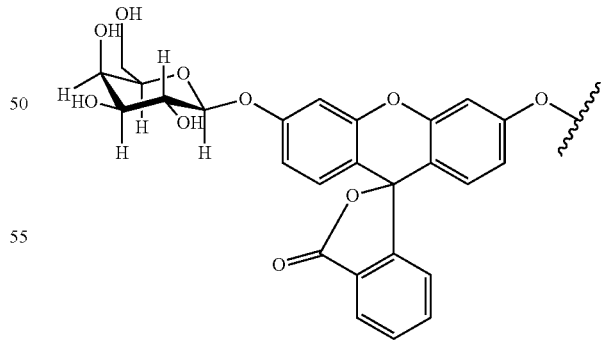

The following catalytic moiety can be used to detect beta hexosaminidase activity. In some embodiments, the method using the catalytic substrate below is for detecting enzymatic conversion of the substrate by a beta-hexosaminidase enzyme. In some embodiments, the method may be for detecting or diagnosing Tay-Sachs disease or for discovering modulators of this activity or disease phenotype.

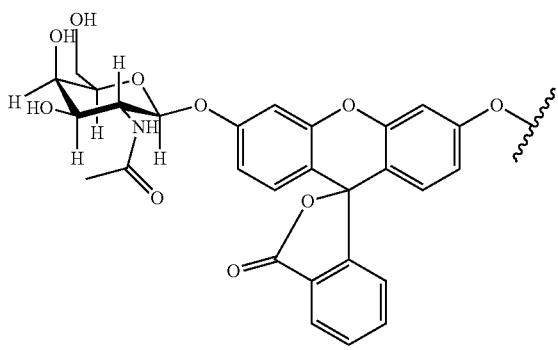

The following catalytic moiety can be used to detect beta alpha-glucosidase activity. In some embodiments, the method using the catalytic substrate below is for detecting enzymatic conversion of the substrate by a alpha-glucosidase enzyme. In some embodiments, the method may be for detecting or diagnosing Pompe's disease or for discovering modulators of this activity or disease phenotype.

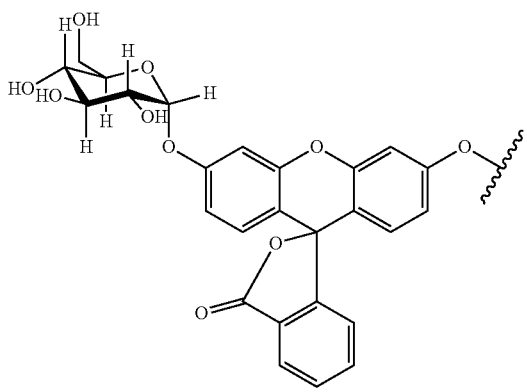

2.3 Other Assay Method Aspects

In a similar manner, positive control, catalytic substrates, and background control moieties may be constructed to perform the methods and make the compositions of the disclosure directed to other enzyme activities, including but not limited to, activities such as phosphatase, kinase, amylase, lipase, protease, phosphorylation, myristoylation, glycosylation, oxygenase, and hydroxylase.

Exemplary substrates and enzymes include those in the following table:

| Ezyme | Substrate |
| --- | --- |
| α-Glucosidase | α-D-Glucose |
| β-Glucosidase | β-D-Glucose |
| α-Galactosidase | a-D-Galactose |
| β-Galactosidase | β-D-Galactose |
| α-Mannosidase | α-D-Mannose |
| β-Mannosidase | β-D-Mannose |
| N-Acetyl-β-glucosaminidase | β-D-N-Acetyl-Glucosamine |
| β-Glucuronidase | β-D-Glucuronic Acid |
| β-D-Fucosidase | β-D-Fucose |
| α-L-Fucosidase | α-L-Fucose |
| β-L-Fucosidase | β-L-Fucose |
| L-Iduronidase | α-L-Iduronic Acid |
| Cellulase | β-D-Cellobiose |
| α-Arabinopyranosidase | α-L-Arabinopyranose |
| β-Xylosidase | β-D-Xylose |
| α-N-Acetyl-neuraminidase | α-D-N-Acetyl-neuraminic acid (Sialic acid) |
| guanidinobenzoatase | aryl esters of p-guanidino-benzoic acid |
| alkaline phosphatase | aryl or alkyl phosphate monoesters |
| acid phosphatase | aryl or alkyl phosphate monoesters |
| aryl sulfatase | aryl sulfate monoesters |
| 4-nitrophenyl phosphatase | aryl phosphates |
| Pyruvate oxidase | pyruvates |
| L-amino acid oxidase | L-amino acids |
| Aldehyde oxidase | aldehydes |
| Xanthine oxidase | xanthines |
| Glucose oxidase | glucose |
| Glycollate oxidase | glycollate |
| Sarcosine oxidase | sarcosine |
| Galactose oxidase | Galactose |
| pepsin | Proteins, esters |
| Protease S | Aspartic or glutamic moieties in proteins |
| Protease K | Proteins, amides |
| trypsin | Lysine or arginine moieties in proteins |
| DNase I | Single chain and double stranded DNA |
| DNase II | Single chain and double stranded DNA, p-nitrophenyl phosphodiesters |
| Rnase | RNA |
| RNase T1 | RNA between 3'guanylic and adjacent nucleotides |
| Nuclease S1 | Single stranded DNA and RNA |
| Beta-agarase | 1,3-linked beta-D-galactopyranose and 1,4-linked 3,6-anhydro-alpha-L-galactopyranose |
| Beta amylase | Alpha-1,4-linked D-glucose |
| cellulase | Beta-1,4-linked D-glucose units |
| dextranase | 1,6-alpha-glucosidic linkages |
| lysozyme | Beta-1,4 bond between N-acetyl muramic acid and N-acetylglucosamine |
| Cholesterol esterase | Sterol esters |
| lipase | Primary acyl bond in triglycerides |
| Phospholipase A2 | Sn-2-acyl bond in phospholipids |
| Phospholipase C | Bond between glycerol and phosphate |
| chymotrypsin | Amides and esters of leucine, methionine, asparagine, glutamine, etc . . . |
| clostripain | Arginine carbonyl |
| collagenase | collagen |
| elastase | Elastin, N-acyl-L-alanine 3-p-nitroanilide |

It is within the knowledge of those skilled in the art to construct a detectable molecule comprising a substrate of interest to monitor the activity of an enzyme of interest. Furthermore, the disclosure provides exemplary methods of protecting fluorophores, conjugation of a reactive element, and conjugation to a nucleic acid.

In some embodiments, intracellular enzymatic activity may be monitored for the purposes of examining cellular phenomena and/or screening the effects of various compounds, wherein the level of the signal from a nucleic acid complex described herein (e.g., increased or decreased signal) in a test sample at a first time point is determined and compared with the level found in a test sample obtained at a later time point. The change in signal may reflect a relative change in enzymatic activity between the two samples.

As one of skill in the art will understand, there will be a certain degree of uncertainty involved in making this determination. Therefore, the standard deviations of the control group levels can be used to make a probabilistic determination and the method of this disclosure are applicable over a wide range of probability-based determinations. Thus, for example, and not by way of limitation, in one embodiment, if the measured level of signal falls within 2.5 standard deviations of the mean of any of the control groups, then that sample may be assigned to that group. In another embodiment if the measured level of signal falls within 2.0 standard deviations of the mean of any of the control groups then that sample may be assigned to that group. In still another embodiment, if the measured level of signal falls within 1.5 standard deviations of the mean of any of the control groups then that sample may be assigned to that group. In yet another embodiment, if the measured level of signal is 1.0 or less standard deviations of the mean of any of the control groups levels then that sample may be assigned to that group. Thus, this process allows determination, with various degrees of probability, in which group a specific sample should be placed.

Statistical methods can also be used to set thresholds for determining when the signal intensity in a test sample can be considered to be different than or similar to the reference level. In addition, statistics can be used to determine the validity of the difference or similarity observed between a test sample's signal intensity and the reference level. Useful statistical analysis methods are described in L. D. Fisher & G. vanBelle, Biostatistics: A Methodology for the Health Sciences (Wiley-Interscience, NY, 1993). For instance, confidence ("p") values can be calculated using an unpaired 2-tailed t test, with a difference between groups deemed significant if the p value is less than or equal to 0.05.

3. Diseases Detection and Monitoring

The methods, compositions, nucleic acids, and kits of the disclosure can be used for the detection of diseases, the monitoring of diseases, and as a drug screening platform. In some embodiments, the disease is characterized as a lysosomal dysfunction disease. In some embodiments, the pathology of the disease includes lysosomal dysfunction.

Lysosomal dysfunction diseases include, for example, autosomal recessive osteopetrosis, Farber disease, Krabbe disease (infantile onset and late onset), Fabry disease (Alpha-galactosidase A), Schindler disease (Alpha-galactosidase B), Sandhoff disease (infantile, juvenile, or adult onset), Tay-Sachs, juvenile hexosaminidase A deficiency, chronic hexosaminidase A deficiency, glucocerebroside, Gaucher disease (Type I, II, and III), lysosomal acid lipase deficiency (early onset and late onset), Niemann-Pick disease (Type A and B), sulfatidosis, metachromatic leukodystrophy (MLD), saposin B deficiency, multiple sulfatase deficiency, mucopolysaccharidoses: MPS I Hurler Syndrome, MPS I S Scheie Syndrome, MPS I H-S Hurler-Scheie Syndrome, Type II (Hunter syndrome), Type III (Sanfilippo syndrome), MPS III A (Type A), MPS III B (Type B), MPS III C (Type C), MPS III D (Type D), Type IV (Morquio), MPS IVA (Type A), MPS IVB (Type B), Type VI (Maroteaux-Lamy syndrome), Type VII Sly Syndrome, Type IX (Hyaluronidase Deficiency); Mucolipidosis: Type I (Sialidosis), Type II (I-cell disease), Type III (Pseudo-Hurler Polydystrophy/Phosphotransferase Deficiency), Type IV (Mucolipidin 1 deficiency); Niemann-Pick disease (Type C and D), Neuronal Ceroid Lipofuscinoses: Type 1 Santavuori-Haltia disease/Infantile NCL (CLN1 PPT1), Type 2 Jansky-Bielschowsky disease/Late infantile NCL (CLN2/LINCL TPP1), Type 3 Batten-Spielmeyer-Vogt disease/Juvenile NCL (CLN3), Type 4 Kufs disease/Adult NCL (CLN4), Type 5 Finnish Variant/Late Infantile (CLN5), Type 6 Late Infantile Variant (CLN6), Type 7 CLN7, Type 8 Northern Epilepsy (CLN8), Type 8 Turkish Late Infantile (CLN8), Type 9 German/Serbian Late Infantile (Unknown), Type 10 Congenital Cathepsin D Deficiency (CTSD); Wolman disease, alpha-mannosidosis, beta-mannosidosis, aspartylglucosaminuria, fucosidosis, lysosomal transport diseases, cystinosis, pycnodysostosis, salla disease/sialic acid storage disease, infantile free sialic acid storage disease (ISSD), glycogen storage diseases, Type II Pompe Disease, Type IIIb Danon disease, and cholesteryl ester storage disease. In some embodiments, the disease is autosomal recessive osteopetrosis. In some embodiments, the disease is Niemann-Pick C disease.

In certain aspects, methods of the disclosure can be used to diagnose or analyze a a sample from a patient. The term "subject" or "patient" is meant any single subject for which the method can be applied and includes, for example, humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls, human sample. In some embodiments, a method of the disclosure is performed on a sample from a subject with a disease described herein. The methods of obtaining a sample from a subject include methods of biopsy such as fine needle aspiration, core needle biopsy, vacuum assisted biopsy, incisional biopsy, excisional biopsy, punch biopsy, shave biopsy or skin biopsy. In certain embodiments the sample is from a diseased or non-diseased tissue. The sample may be obtained from any of the tissues provided herein that include but are not limited to tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or mucosal membrane, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples may be obtained for performance of the methods of the disclosure. In other cases, multiple samples, such as one or more samples from one tissue type and one or more samples from another tissue may be obtained for performance of the methods of the disclosure. In some cases, multiple samples may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

4. Kits

The materials and components described for use in the methods may be suited for the preparation of a kit. Thus, the disclosure provides a detection kit useful for determining the catalytic activity and/or the presence, absence, or concentration of an analyte in a sample, cell or region thereof. Specifically, the technology encompasses kits for measuring the catalytic activity of one or more cells or intracellular compartment in a cell in a sample. For example, the kit can comprise a nucleic acid complex as described herein.

In some embodiments, the methods described herein may be performed by utilizing pre-packaged kits comprising the necessary reagents to perform any of the methods of the technology. For example, such a kit would include a detection reagent for measuring the catalytic activity of a biological sample or compartment. In one embodiment of such a kit, the detection reagents are the nucleic acid complexes of the disclosure. Oligonucleotides are easily synthesized and are stable in various formulations for long periods of time, particularly when lyophilized or otherwise dried to a powder form. In this form, they are easily reconstituted for use by those of skill in the art. Other reagents and consumables required for using the kit could be easily identified and procured by those of skill in the art who wish to use the kit. The kits can also include buffers useful in the methods of the technology. The kits may contain instructions for the use of the reagents and interpreting the results.

In some embodiments, the technology provides a kit comprising at least one sample packaged in one or more vials for use as a control. Each component of the kit can be enclosed within an individual container and all of the various containers can be within a single package, along with instructions for performing the assay and for interpreting the results of the assays performed using the kit.

In some embodiments, the kit comprises a device for the measurement of catalytic activity in a sample. In some embodiments, the device is for measuring catalytic activity in a biological compartment in cell culture or in whole, transparent organisms (e.g., *C. elegans*).

5. Examples

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

5.1 Example 1: DNA Nanodevices Spatiotemporally Map Enzymatic Function In Vivo

The paucity of technologies to directly visualize enzyme activity in vivo is a major obstacle to investigate dysregulated signalling. Described in this example is a DNA-based imaging technology to spatiotemporally map protein disulphide isomerase activity. It confines the detection chemistry to a designated organelle, and quantitatively images disulphide reduction therein. A range of enzymatic cleavage reactions are amenable to analysis by this reporter system. Traditional reporters either target a specific protein or use small molecules, and these afford information only on cellular locations corresponding to either maximal protein abundance or activity. This is the first molecular imaging technology that can interrogate minor, yet important, subcellular populations of enzyme activity.

5.1.1 Design and Response of Ratiometric Reporters of Disulphide Exchange

The DNA-based, ratiometric reporter consists of three modules with three distinct functions (FIG. 1A). The first is a sensing module, consisting of a reaction centre for thioldisulphide exchange that results in the formation of an active fluorophore (star, FIG. 1A, $\lambda_{em}$=520 nm), described later. The second comprises a normalizing module, consisting of a rhodamine dye (FIG. 1A, $\lambda_{em}$=590 nm) whose fluorescence properties are insensitive to disulphide exchange, and to lumenal ionic variations within endocytic organelles. The third module comprises a targeting functionality consisting of a 34 nucleotide DNA duplex that serves two purposes, wherein the diamond indicates $TDX_{OFF}$. The first is to display the sensing and normalizing modules in a precise, 1:1 stoichiometry. The second is to target the entire assembly for specific uptake by coelomocytes in *C. elegans*, by co-opting scavenger receptors for trafficking along the endolysosomal pathway.

The working principle of the sensing module of the disulphide exchange reporter is shown in FIG. 1B. This module comprises a dye such as one derived from 6'-O propargyl fluorescein whose fluorescence is diminished because the molecule is conjugated via a carbonate linker. At the other end, the carbonate linker is connected to a thiopyridyl group via a disulphide bond. Disulphide reduction by thiol exchange results in the formation of a thiol-containing intermediate that undergoes spontaneous intramolecular cyclization to eliminate 1,3-oxathiolan-2-one, releasing the fluorescein moiety leading to a dramatic increase in fluorescence intensity at 520 nm. The synthesis of this module is described herein (Scheme 1 and Scheme 2).

To make a quantitative reporter system for disulphide reduction under conditions of high autofluorescence that are encountered in living systems, two more nanodevices were made. One of these, $TDX_{ON}$, comprises the DNA duplex attached to fluorescein at the 6'-O position (FIG. 1B), where fluorescein is not protected. $TDX_{ON}$ can also be obtained by completely reducing TDX, such that the fluorescein moiety on TDX is 100% deprotected. TDX could also turn on due to hydrolysis of the carbonate at the 3'-O position. To account for this, $TDX_{OFF}$ was also made, which is designed to capture background hydrolysis, where 6'-O propyl fluorescein is protected with a benzyloxycarbonate moiety. Thus $TDX_{OFF}$ reports non-specific hydrolysis and reveals the specificity of disulphide exchange reported by TDX. The synthesis and characterization of TDX, $TDX_{ON}$ and $TDX_{OFF}$ are described in Scheme 1 and 2 and the description below.

In the presence of 5 mM glutathione (GSH) in 0.1 M phosphate buffer, pH=7.2, TDX fluorescence at 520 nm (G, 6'-O propyl fluorescein) increases with time, while the fluorescence of the normalizing module, at 590 nm (R, rhodamine), remains constant. FIG. 1D shows the ratio of emission intensities of 6'-O propyl fluorescein and rhodamine (G/R) as a function of time that reveals that the reaction is 80% complete in 30 min (FIG. 1D). Importantly, under the same experimental conditions, $TDX_{OFF}$, showed no such fluorescence increase (FIG. 5B) with the G/R ratio remaining unchanged over at least 2 h, indicating that the fluorescence increase observed in TDX is only due to disulphide exchange (FIG. 1D).

5.1.2 TDX Detects Thiol Disulfide Exchange in Late Endosomes In Vivo

The inventors then sought to deploy the TDX reporter system to measure thiol disulphide exchange, if any, that occurs along the endolysosomal pathway in *Caenorhabditis elegans*. DNA nanodevices selectively label six scavenger cells called coelomocytes that are present in pseudocoelom of the *C. elegans*. This is because DNA nanodevices undergo endocytosis mediated by scavenger receptors present on coelomocytes. Briefly, on this endocytic pathway post-injection into the pseudocoelom, DNA nanodevices localise in early endosomes at t=10 min, in late endosomes at t=17 min, and in lysosomes at t=60 min.

Figure 2B:
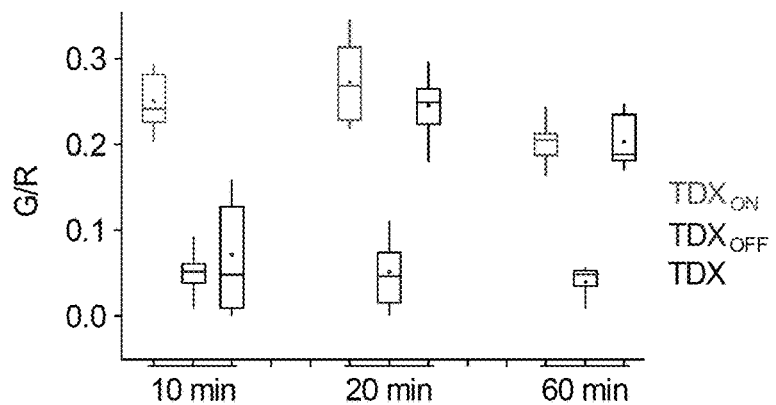
Figure 6:
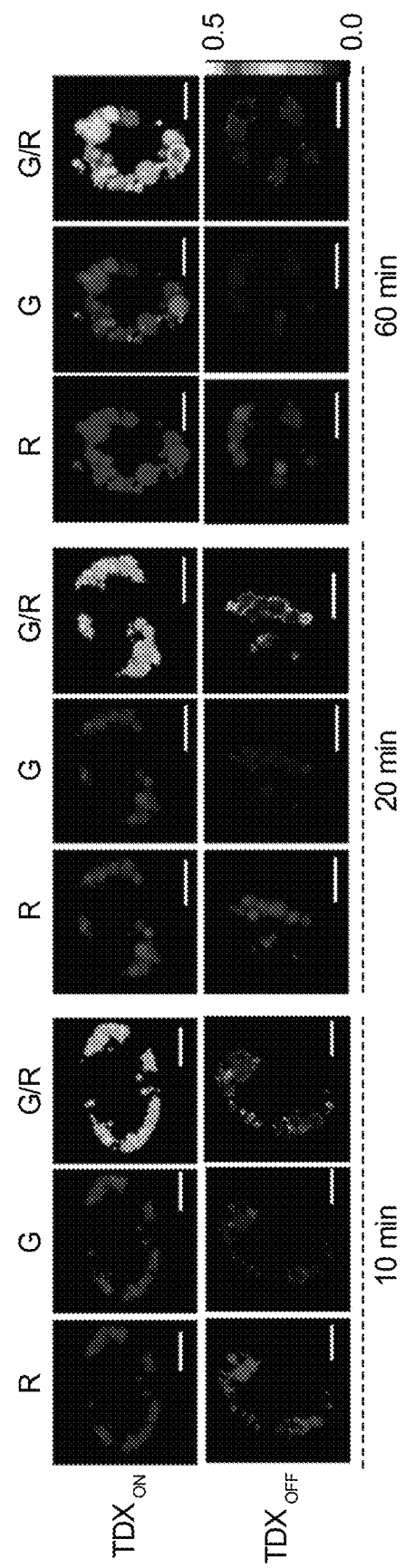
FIG. 6 Illustrates pseudocolour images of $TDX_{ON}$, (upper panel) and $TDX_{OFF}$ (lower panel) at 10 min, 20 min and 60 min post injection of wild type worm (N2). Sale bar-5 µm.

Upon injection of 2 µM TDX into the pseudocoelom of wild type (N2) nematodes, fluorescence images of live nematodes were acquired in fluorescein (G) and rhodamine (R) channels as a function of time. At each time point, ratiometric maps of G/R intensities were generated as described and are presented in pseudocolour in FIG. 2A. It was observed that the G/R ratio was maximal at 20 minutes post injection and remained almost constant thereafter (FIG. 2A). When a similar experiment was conducted with $TDX_{OFF}$ in N2 nematodes, the G/R ratio showed negligible change and remained constant up to the maximum duration of the experiment, i.e., 60 mins (FIGS. 2B and 6). This clearly indicates that the increase in G/R ratio observed in the case of TDX is due to thiol-disulphide exchange and not from esterolytic cleavage.

Figure 2C:
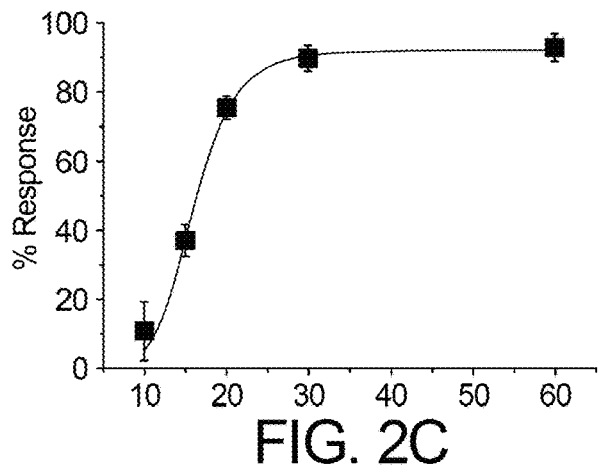

Along the endolysosomal pathway, the lumenal pH decrease affects the fluorescence of fluorescein due to the pH sensitivity of the latter. Described herein is the development of a tripartite reporter system for endosomal thiol-disulphide exchange comprising $TDX_{ON}$, $TDX_{OFF}$ and TDX, that jointly corrects for a number of effects on the fluorescence of the sensor module. For each time point, in N2 nematodes, three separate sets of experiments are performed, injecting either $TDX_{ON}$, $TDX_{OFF}$ or TDX, and for each, fluorescence images in the G and R channels are acquired, G/R ratios are calculated, and heat maps are generated as described (FIG. 2B). At any given time t, the G/R ratios and heat maps of $TDX_{ON}$ correspond to the maximum observable value of thiol-disulphide exchange, and the heat maps of $TDX_{OFF}$ correspond to the minimum observable value of thiol-disulphide exchange, independent of compartment identity. Thus, at each time-point, one could calculate the percentage response of TDX (FIG. 2C) as a function of time in live nematodes using the equation $(^{G/R}TDX - ^{G/R}TDX_{OFF})/(^{G/R}TDX_{ON} - ^{G/R}TDX_{OFF})$. This yielded a sigmoidal curve for thiol-disulphide exchange as a function of time where, 20 min post injection the reaction was complete. (FIG. 2C).

Figure 2D:
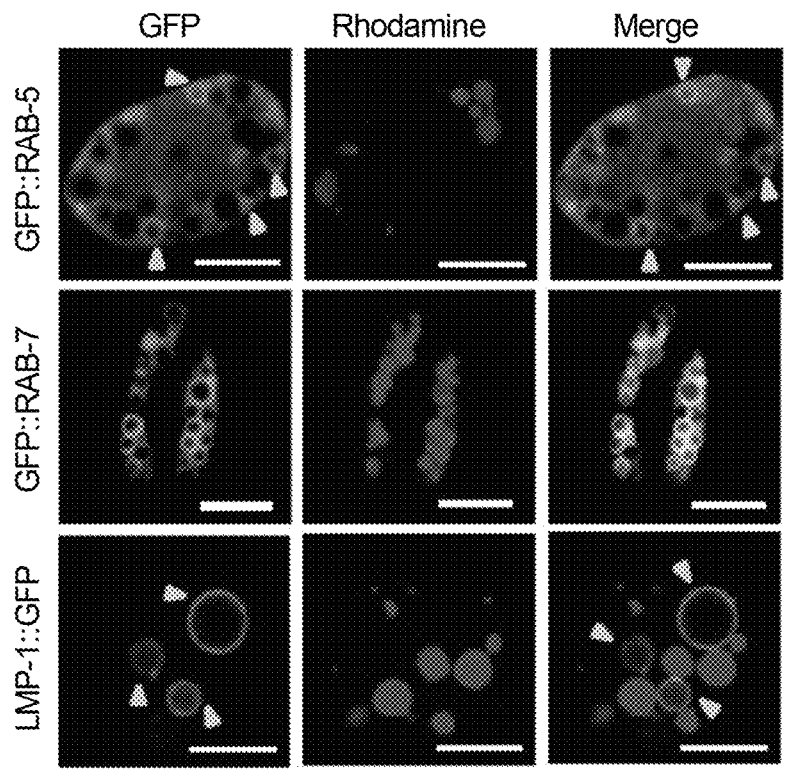
Figure 2E:
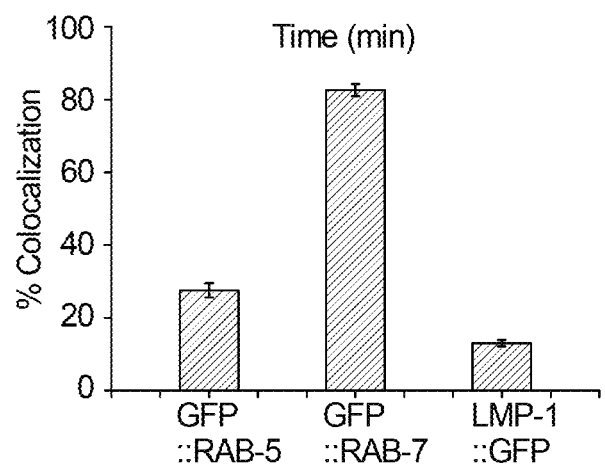

Importantly, for as long as 10 minutes, TDX hardly reacts, starts responding at t=15 min and by t=20 minutes, the disulphide exchange reaction is ~80% complete. In order to determine the identity of the endolysosomal compartment at t=20 min, colocalization studies were performed with various endosomal markers. TDX carrying only a rhodamine label ($TDX^R$) was injected in transgenic nematodes expressing GFP::RAB-5 as an early endosomal marker, GFP::RAB-7 as an late endosomal/lysosomal marker and LMP-1::GFP as a lysosomal marker and assayed for colocalization of GFP with $TDX^R$ at 20 min post injection (FIG. 2D). $TDX^R$ showed only 30% and 10% colocalization in GFP::RAB-5 and LMP-1::GFP positive vesicles respectively, but for GFP::RAB-7 the inventors observed 85% colocalization (FIG. 2E). This indicates that, at 20 min post-injection, $TDX^R$ is present predominantly in the late endosome. Taken together with the kinetic evolution of the G/R ratio (FIG. 2B), the tripartite TDX reporter system clearly reveals that thiol-disulphide exchange occurs in late endosomes in the coelomocytes of *C. elegans*.

5.1.3 Endosomal Disulphide Reduction is Protein-Mediated

Figure 3A:
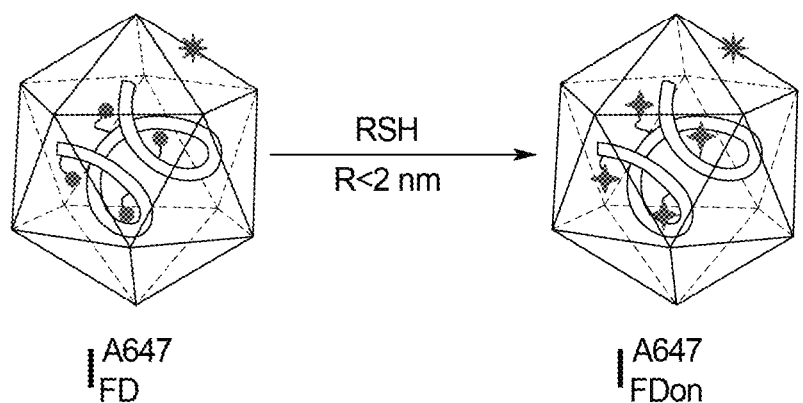
FIG. 3A-D shows that endosomal disulphide reduction is protein-mediated.
Figure 7B:
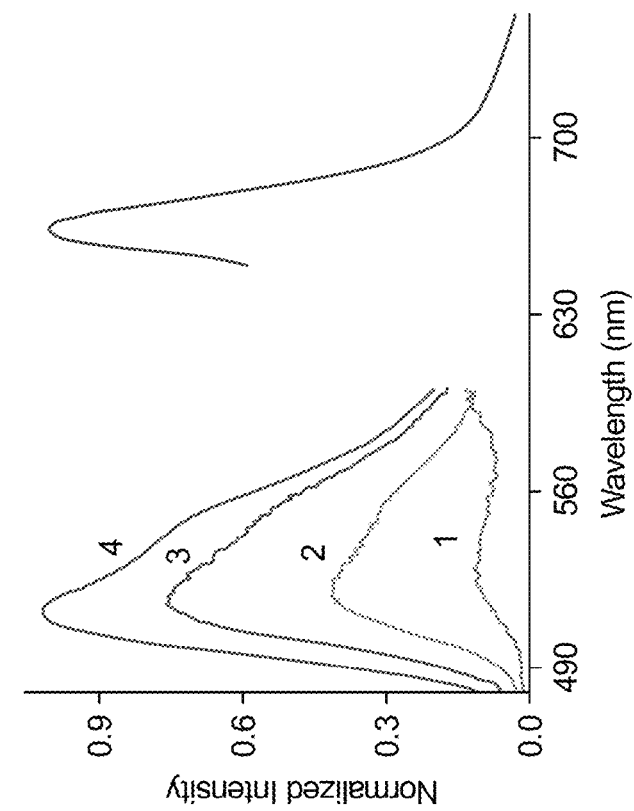
FIG. 7B illustrates a fluorescence signal evolution of $I^{A647FD}$ (3 μM) at $\lambda_{em}$=520 nm and $\lambda_{em}$=660 nm in presence of only buffer, (1) Dex-SH (trace 2, 40 KDa, 1 mM), Glutathione (trace 3, 1 mM) and $H_2S$ (trace 4, 1 mM) in 0.1M phosphate buffer at pH=7.2 at 1 hr time point of incubation. In presence of smaller size thiol such as glutathione and H2S, $I^{A647FD}$ shows increase emission at 520 nm wavelength compare to that of bigger size thiols like Dextran-SH (40 KDa).
Figure 7A:
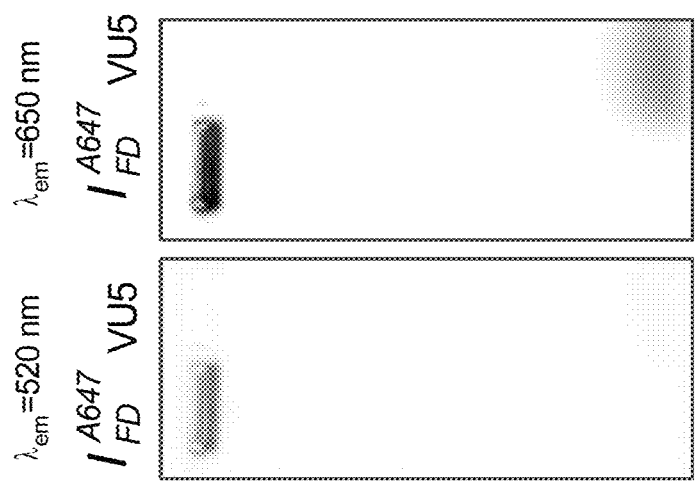
FIG. 7A illustrates 0.8% Agarose gel electrophoresis of $I^{A647FD}$ (1st lane) and precursor of icosahedron $VU_5$ (2nd lane). The gel was run for 1 h at 100 mV in presence of 1×TAE (Tris base-acetic acid-EDTA) buffer. The gel was imaged in two channel at $\lambda_{em}$=520 nm and $\lambda_{em}$=660 nm.

In theory, the observed intra-endosomal disulfide exchange could be mediated either by small molecules like cysteine, glutathione, $H_2S$, etc., or by enzymes. To check which of these two scenarios is operational in the endosomes of *C. elegans*, a well-characterized, porous icosahedral DNA nanocapsule developed by the inventors was used. The nanocapsule has a uniform pore size of 2.8 nm. A chemically modified dextran (FD) bearing 2-3 disulphide sensing modules on average was created, the synthesis and characterization of which is presented in detail in the information following. Then the FD was encapsulated inside a DNA icosahedron bearing an Atto647N label on one of the component strands to give $I^{4647}_{FD}$ (FIG. 3A). The Atto647 dye acts as a normalizing fluorophore as its fluorescence intensity at 665 nm (R) is independent of disulphide exchange while simultaneously functioning as a fiducial fluorophore to locate icosahedron inside coelomocytes. The synthesis and characterization for $I^{4647}_{FD}$ is also presented in (FIG. 7A).

Figure 3B:
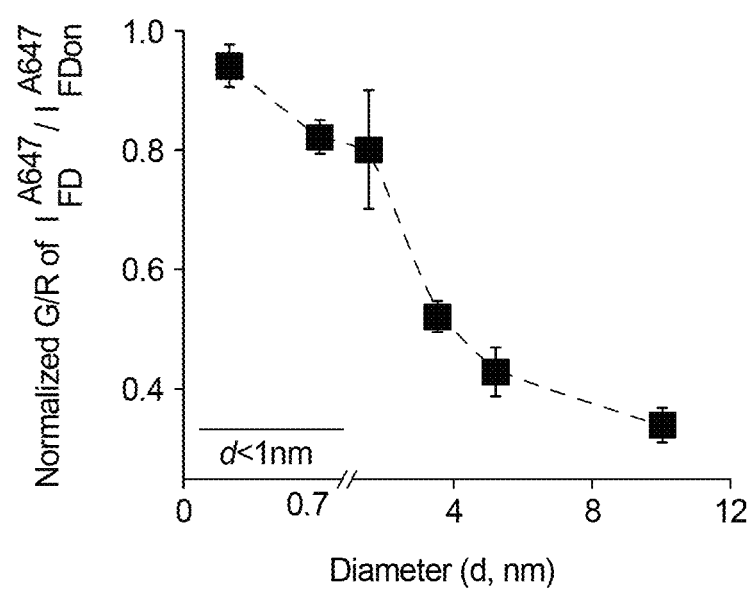

Due to its well-defined, pore size $I^{4647}_{FD}$ should permit small thiols such as GSH, cysteine and $H_2S$, with sizes <1 nm, to pass freely through the capsule, access the chemically modified dextran FD encapsulated within and mediate disulphide exchange on FD. However, macromolecular thiols with sizes greater than 3 nm should not be able to access the interior of the icosahedron and therefore be unable to reduce the encapsulated FD. The inventors tested $I^{4647}_{FD}$ for size selectivity towards disulphide exchange with a spectrum of differently sized thiols in vitro and observed that an increase in fluorescence intensity at 520 nm (G) occurred only in the case of smaller size thiols such as glutathione, cysteine and $H_2S$, while larger thiols of molecular weight >10 kDa could not reduce FD (FIG. 7B). The fold change in G/R ratio of $I^{4647}_{FD}$ for complete disulphide exchange for this size selective reporter was found to be 9.4 (FIG. 3B). The inventors also made a sample of DNA icosahedron carrying an Atto647N label, and encapsulating FD which had been completely disulphide exchanged to give $I^{4647}_{FD-ON}$. The inventors also made a sample of empty DNA icosahedron, carrying an Atto647N label, without cargo inside to give $I^{4647}_{FD-OFF}$, to evaluate the contribution of autofluorescence.

Figure 3C:
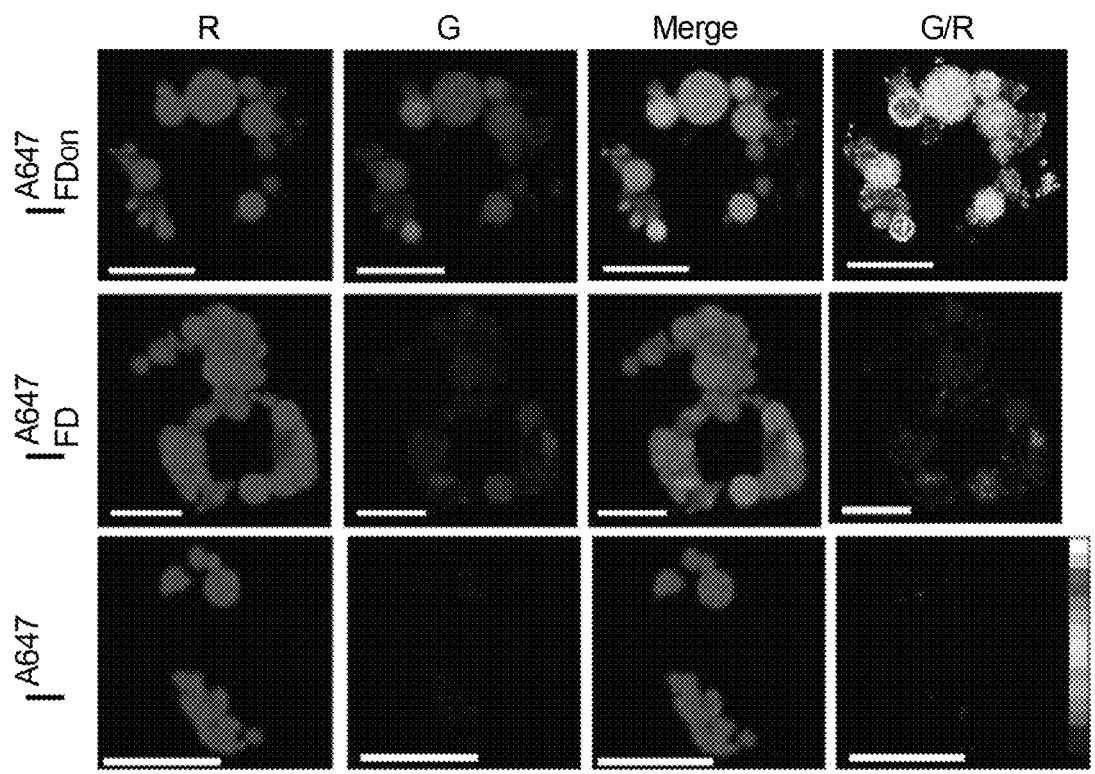
Figure 3D:
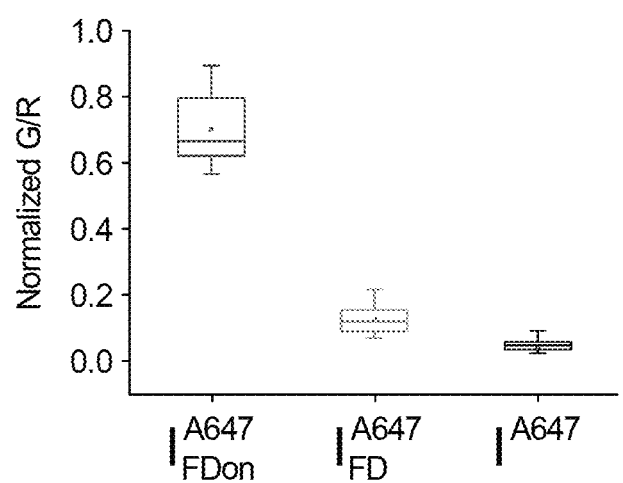

The inventors then used a tripartite nanocapsule reporter system comprising $I^{4647}_{FD}$, $I^{4647}_{FD-OFF}$ and $I^{4647}_{FD-ON}$ to test whether the observed intra-endosomal disulphide exchange was mediated by proteins or by small molecule thiols. Since DNA nanocapsules are also taken up by scavenger receptors in coelomocytes, the inventors injected either $I^{4647}_{FD}$, $I^{4647}_{FD-ON}$ or $I^{4647}_{FD-OFF}$ into the pseudocoelom of N2 nematodes and acquired images in the fluorescein and Atto647N channels at t=30 min. If $I^{4647}_{FD}$ undergoes disulphide reduction by small molecule thiols, then, it should show a G/R ratio similar to that of $I^{4647}_{FD-ON}$. Importantly, the G/R ratio of $I^{4647}_{FD}$ at t=30 min was only ~16% that of $I^{4647}_{FD-ON}$ (FIG. 3C and FIG. 3D). The resistance of $I^{4647}_{FD}$ to turn on compared to TDX reveals that disulphide exchange due to small molecule thiols is insignificant within endosomes. In addition, a comparison of the in vitro and in vivo kinetics of disulphide exchange at pH 6 strongly indicates that intra-endosomal disulphide exchange is enzyme catalysed (FIG. 1D).

5.1.4 PDI-3 and TRX-1 Catalyze Disulfide Exchange in Late Endosomes

Figure 4A:
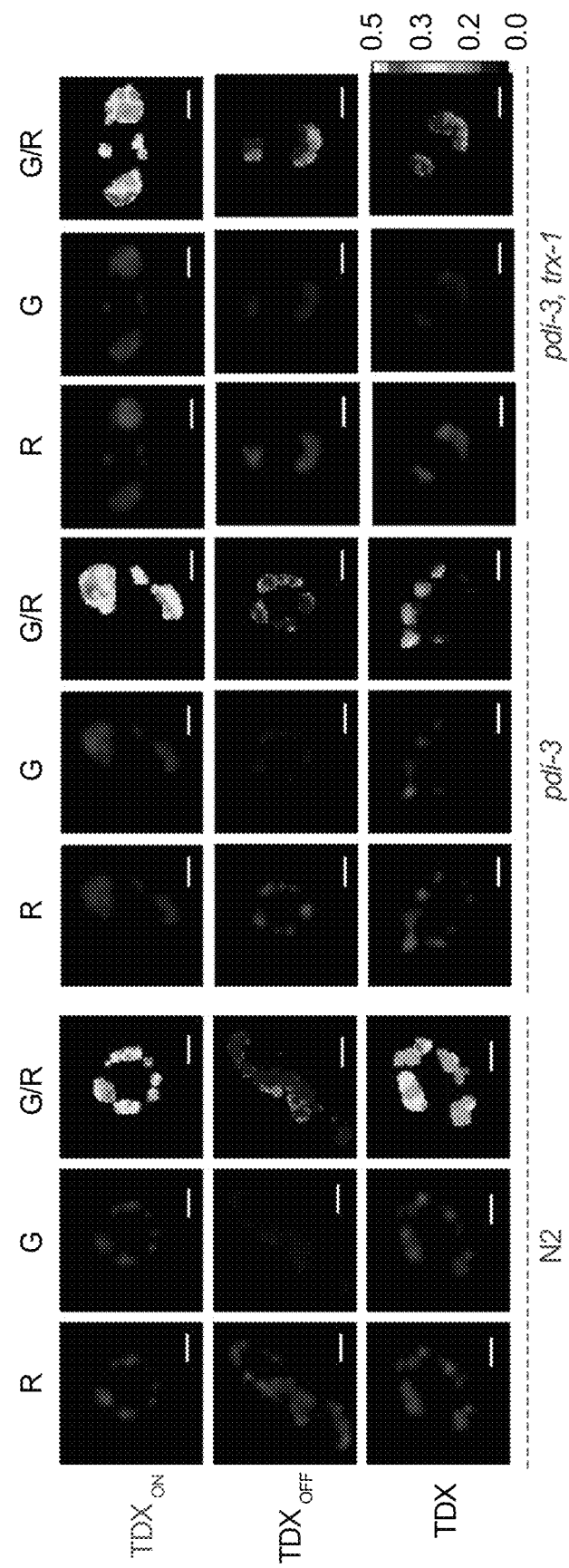
FIG. 4A-C shows that PDI-3 and TRX-1 catalyze disulfide exchange in late endosomes.
Figure 4B:
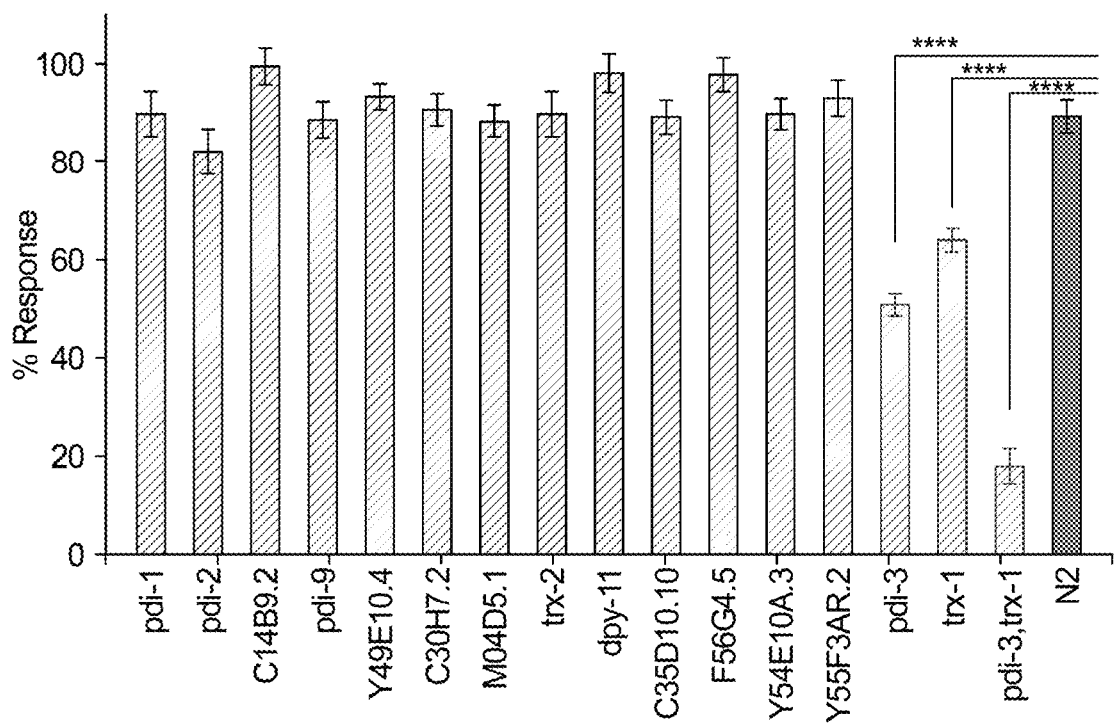
Figure 4C:
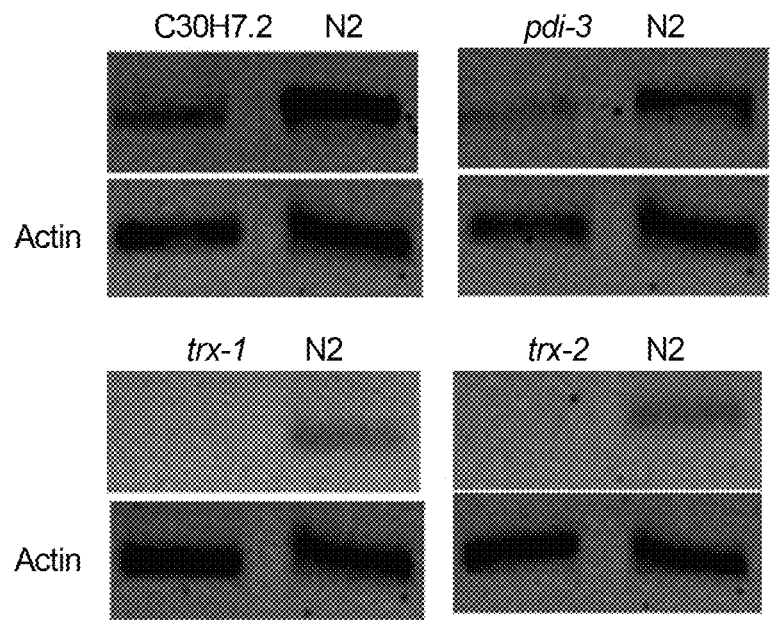
Figure 8M:
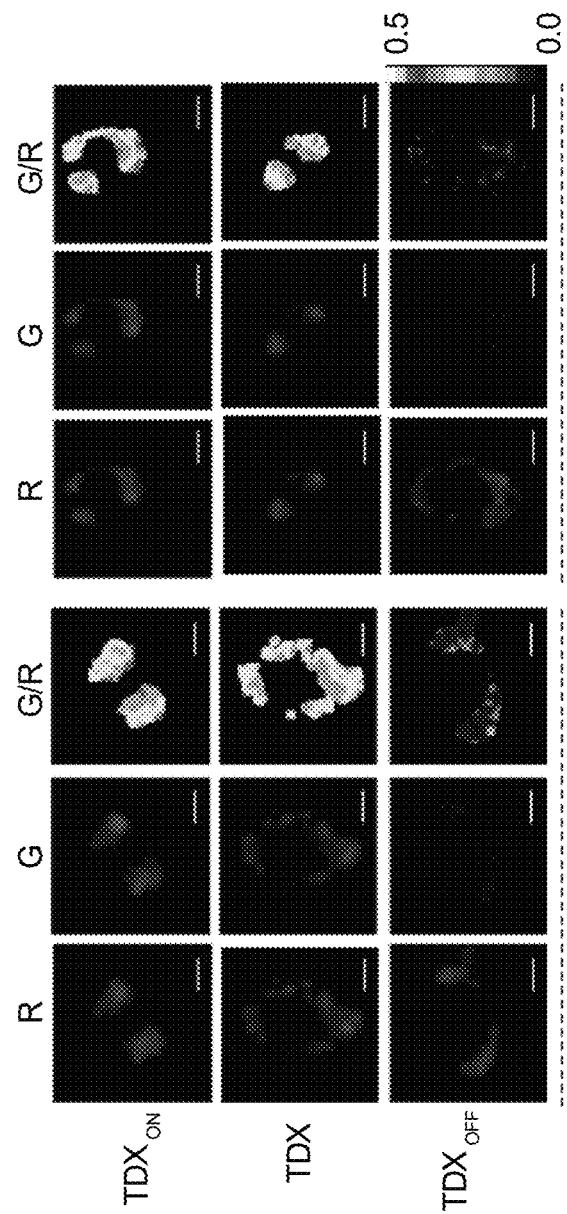
FIGS. 8A-N illustrates for A-F and A'-F': Pseudocolour images and quantification data for $TDX_{ON}$, (upper panel) TDX (middle panel) and $TDX_{OFF}$ (lower panel) at 20 min time post injection (a, b, c, d, e and f) and their respective G/R ratio plot at 20 min post injection for (a', b', c', d', e' and f') for pdi-1, pdi-2, C14B9.2, pdi-6, Y49E10.4, C30H7.2 RNAi worm respectively. Scale bar=5 μm. For G-L and G'-L': Pseudocolour images and quantification data for $TDX_{ON}$, (upper panel) TDX (middle panel) and $TDX_{OFF}$ (lower panel) at 20 min time post injection (g, h, I, j, k and l) and their respective G/R ratio plot at 20 min post injection for (g', h', I', j', k' and l') for M0415.1, trx-1, trx-2, dpy-11, ('351) 10.10, F56G4.5 RNAi worm respectively. Scale bar=5 μm. For M-N and M'-N': Pseudocolour images and quantification data for $TDX_{ON}$, (upper panel) TDX (middle panel) and $TDX_{OFF}$ (lower panel) at 20 min time post injection (m and n) and their respective G/R ratio plot at 20 min post injection for (m' and n') for Y54E10A.3, Y55F3AR.2 RNAi worm respectively. Scale bar=5 μm.
Figure 8N:
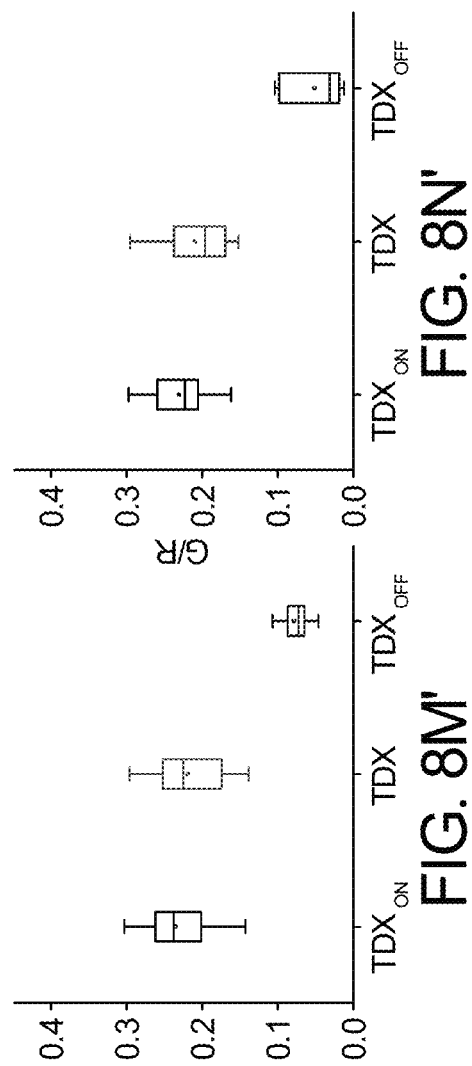
Figure 10A:
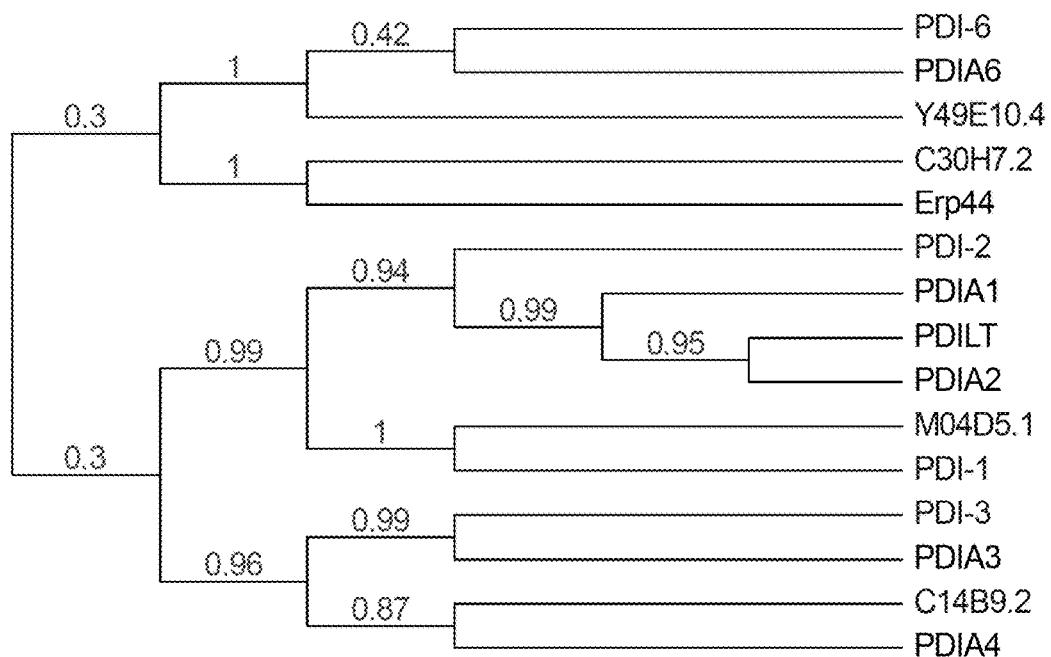
FIG. 10A illustrates phylogenetic tree comparing the proteins having A) more than one thioredoxin domain (upper).
Figure 10B:
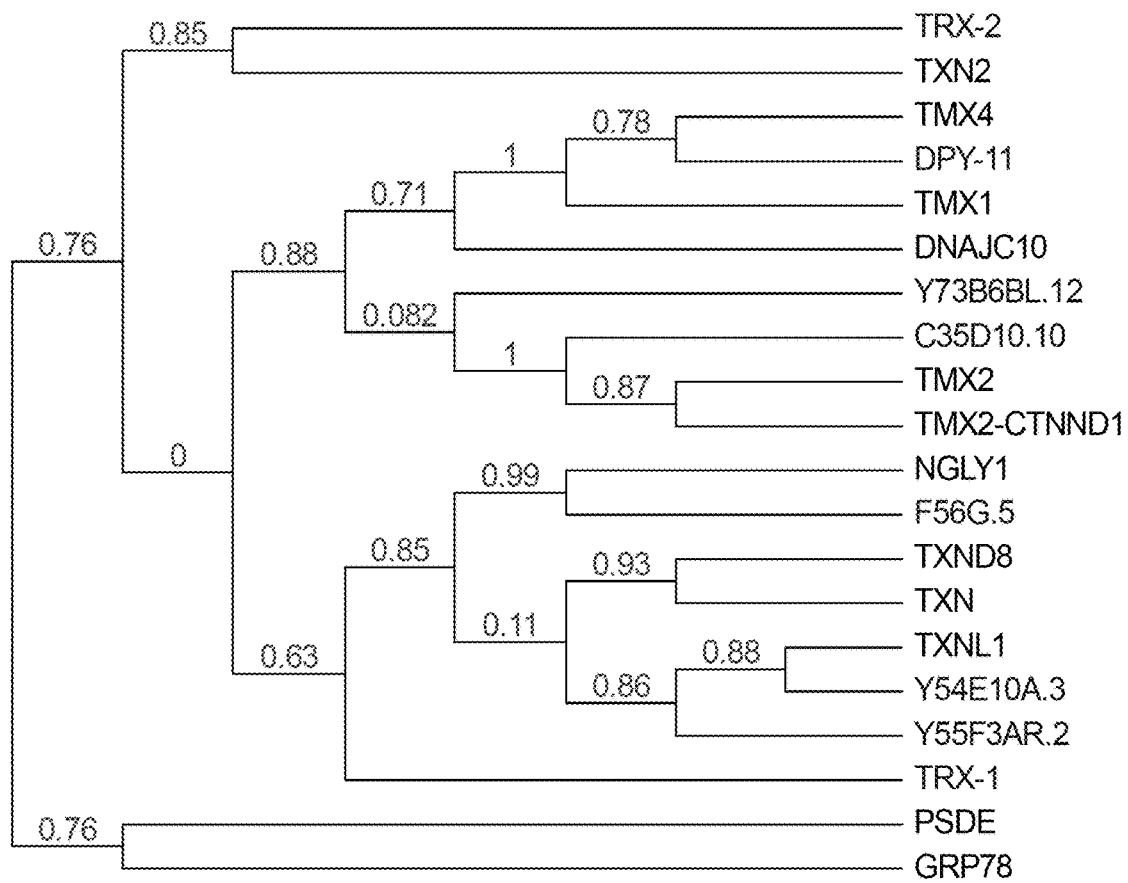
FIG. 10B illustrates one thioredoxin domain (lower) of *C. elegans* with *H. sapiens*. The numbers next to each node represent a measure of sequence similarity for the node. These are generally numbers between 0 and 1 where 1 represents maximal similarity.

Next, the molecular players that mediate disulfide reduction in late endosomes in coelomocytes were identified. Proteins that catalyze disulfide exchange generally contain thioredoxin domains, e.g., thioredoxins or protein disulfide isomerases. Using BLASTP approximately 23 proteins were found in the *C. elegans* genome that contained at least one thioredoxin domain. Seven were excluded as they contained either a mitochondrial or nuclear localization sequence, which precluded their presence in the endosomal milieu (Table 4). Fifteen candidate genes were narrowed by RNA interference (RNAi) and, in each of these genetic backgrounds the inventors quantitated the extent of intraendosomal thiol disulfide exchange using the tripartite TDX reporter system (FIG. 8). Efficiency of RNAi knockdown of relevant genes were confirmed by RT-PCR followed by analysis using gel electrophoresis (FIG. 4C).

In a given genetic background, the inventors injected either $TDX_{ON}$, $TDX_{OFF}$ or TDX and measured G/R ratios for each of these DNA assemblies at 20 min post injection. The percentage response of TDX in each genetic background was mapped. FIG. 4A shows representative pseudocolor maps for three different genetic backgrounds. The percentage response for each genetic background was quantified (FIG. 4B). Two clear hits were found, where knocking down pdi-3 or trx-1 knockdown showed 50% and 40% reduction in disulphide exchange respectively as compared to wild type nematodes (FIG. 4B). Importantly, simultaneous knockdown of both pdi-3 and trx-1 in nematodes showed a dramatic reduction of disulfide exchange, nearly comparable to G/R values seen with $TDX_{OFF}$. This indicates that disulfide reduction in the late endosome is predominantly due to pdi-3 and trx-1. The main function of TRX-1 is to reduce several disulfide containing proteins, thus serving to enhance the activity of stronger reducing proteins e.g., protein disulfide isomerases (PDIs). In fact, the oxidation potential of PDIs are nearly 50 fold higher than thioredoxin, suggesting that, at an acidic pH of 6.0 in the late endosome, PDI-3 it is likely to be the major player along with TRX-1.

Interestingly both PDI-3 and TRX-1 are soluble proteins. Thioredoxin-1 (TRX-1) is known to be maximally present in the cytosol. PDI-3 has an ER retention signal suggesting that the major population is in the endoplasmic reticulum (ER). In fact ERp57, which is the vertebrate homolog of PDI-3, has been shown to be localized in the ER (even though it has a slightly weaker ER retention signal). Importantly these DNA-based probes reveal the existence of a minor population of TRX-1 and PDI-3 in late endosomes, and that this minor population carries out an essential function for the cell by mediating disulfide exchange therein. In mammalian cells, both thioredoxin-1 and ERp57 undergo secretion where they adhere via electrostatic interaction at the plasma membrane. It is notable that despite the presence of PDI-3 and TRX-1 on the plasma membrane, and the presence of extracellular glutathione at 1-10 µM, disulphide reduction of the DNA-based probes occurs specifically in the late endosome revealing the existence of a minor pool of PDI-3 and TRX-1 in the late endosome.

5.1.5 Conclusion

The modular design of the DNA-based tripartite fluorescent reporter system enables quantitative imaging assays for intra-endosomal disulphide exchange in situ in coelomocytes of *C. elegans*. It revealed that thiol-disulphide exchange along the endolysosomal pathway occurs mainly in the late endosome.

As thiol-disulphide exchange can be mediated by small molecule thiols or by enzymes, the inventors developed a nanocapsule reporter system that is responsive only to disulphide reduction by small molecule thiols. This revealed that disulfide reduction in the late endosome was mediated by molecules larger than 2 nm, implicating the action of proteins. Lumenal pH of the late endosome corresponds to pH 6.0, where uncatalyzed disulphide exchange is expected to be impeded given that cysteine or glutathione have pKa values greater than 8.0. In fact, the pKa of the N-terminal active site cysteine of PDI can be as low as 4.8, while that of thioredoxins can range between ~6.0-7.0. Thus, in the late endosome lumen, proteins such as PDI and thioredoxins are highly efficient at disulphide exchange, unlike cysteine or glutathione.

Quantitative imaging of thiol-disulphide exchange in RNAi knockdowns of various candidate genes revealed that PDI-3 and TRX-1 were responsible for the observed disulfide reduction in vivo. Though PDI-3 and TRX-1 are predominantly localized in the endoplasmic reticulum (ER) and cytosol, it is clear that a minor pool of these proteins is localized in pockets of the cell where they perform critical functions. For example, a minor population of endosomal ERp57 is essential for antigen cross-presentation required for an immune response. Interestingly pathogens like *B. cenocapacia, C. diphtheriae*, the HIV virus, the rotavirus ECwt, ganjam virus etc. exploit such minor populations of PDI-s like ERp57 present on the plasma membrane or in endosomes, to infect the host cell. Thus the inhibition of this minor population of PDIs is of great interest to develop broad-spectrum anti-infectives. Our tripartite reporter system is able to directly assay enzyme activity of these minor, yet important populations by localizing the detection chemistry within a compartment. This concept may be generalized to a wide swath of enzyme-cleavage chemistries by displaying the appropriate detection chemistry on an organelle targeted DNA nanodevice, and the use of corresponding "ON"/"OFF" nanodevices to selectively interrogate enzymatic function in organelles.

Traditional small molecule reporter systems cannot provide spatial information within the cell. Strategies to probe enzymatic function such as activity based protein probes can pinpoint multiple players for a given chemistry, however the dynamics of protein activity remains inaccessible, as these probes function by enzyme inhibition. While localization technologies such as fluorescent proteins, the SNAP-tag or the Halo-tag provided do provide spatial information, the information they provide is restricted to the major population of the protein of interest. The organelle-targetable nanodevice system described here can selectively interrogate minor populations of enzymes involved in critical cellular functions, which cannot otherwise be studied.

5.1.6 Materials and Methods

All the chemicals used for the synthesis were purchased from commercial source (Sigma, USA). $^1$H NMR and $^{13}$C NMR spectra of the newly synthesized compounds were recorded on a Bruker AVANCE II+, 500 MHz NMR spectrophotometer. TMS is used as an internal standard. Mass spectra were recorded in Agilent 6224 Accurate-Mass TOF LC/MS. HPLC purified oligonucleotides conjugated with either fluorophore or azide functional group were obtained from Integrated DNA Technologies (IDT, USA). All oligonucleotides are ethanol precipitated and quantified by UV absorbance at λ=260 nm.

Figure 11:
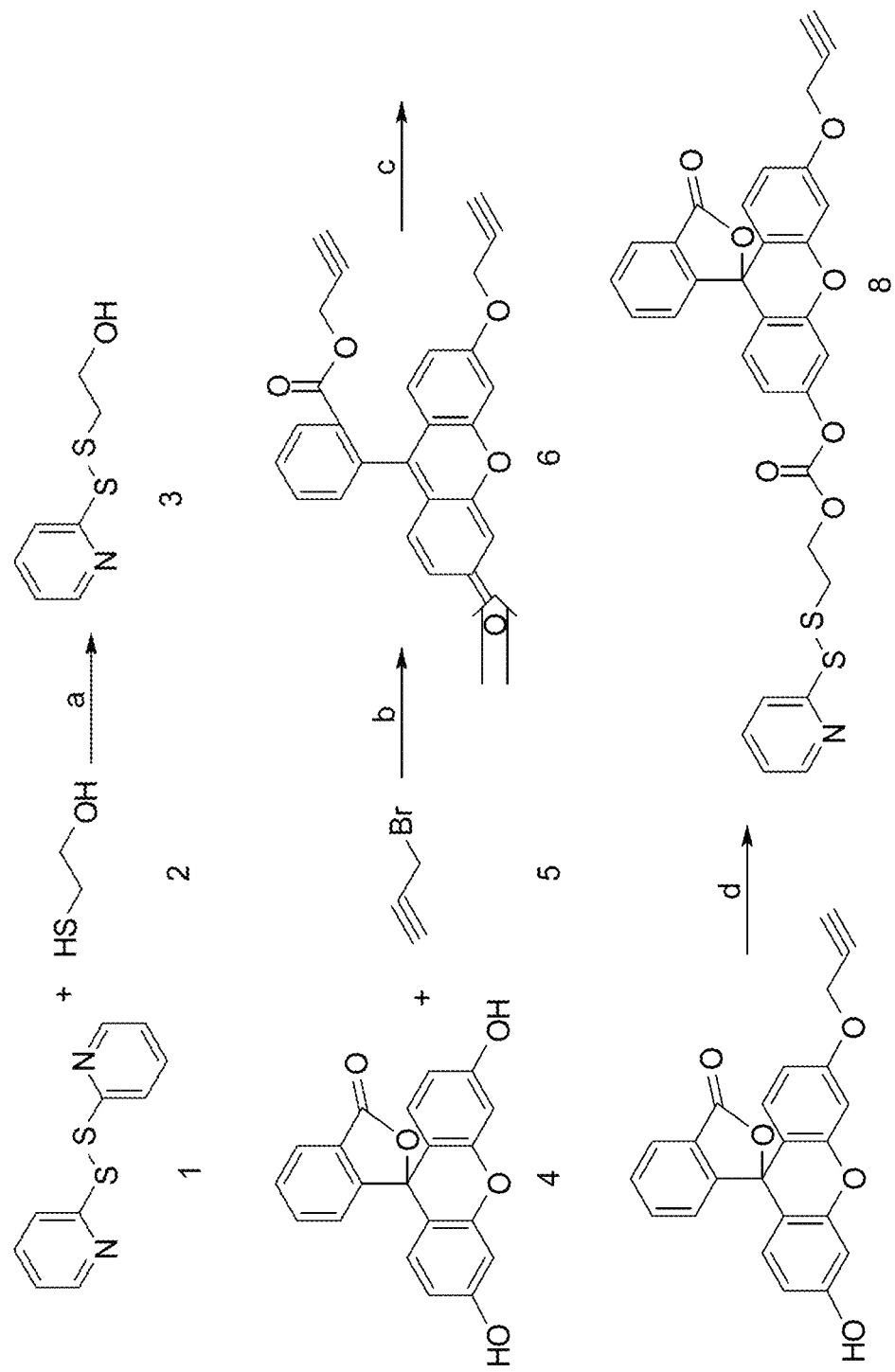
FIG. 11 illustrates a synthesis scheme of thiopyridyl conjugated blocked 6'-O propargyl fluorescein.

Scheme 1: Synthesis of thiopyridyl conjugated blocked 6'-O propargyl fluorescein is shown in FIG. 11.

Reagents and conditions: a) MeOH, rt, 12 h, yield=72%, b) $K_2CO_3$, DMF, 65° C., 4 h. yield=92%, c) NaOH, THF-$H_2O$, rt, 2 h. yield=41%, d) Compound 3, $COCl_2$, $Et_3N$, THF, yield=40%

Synthesis of Compound 3: The synthesis of compound 3 was partially followed from literature reported procedure (M. R. Molla, et al, *Macromolecules*. 45, 8561-8570 (2012)). 1 g (4.5 mmol) Aldrithiol was dissolved in 10 ml of methanol in a round bottom flask. 2-mercapto ethanol (0.106 ml, 1.5 mmol) was added dropwise and the reaction mixture was stirred overnight at room temperature for 12 h. Methanol was evaporated from the reaction mixture and the residue was purified by silica gel column chromatography using 30% ethyl-acetate in hexane as an eluent. Pure compound 3 was obtained as a colourless liquid in 72% yield. $^1$H NMR (500 MHz, $CDCl_3$, TMS): δ (ppm): 8.51 (m, 1H), 7.58 (m, 1H), 7.40 (m, 1H), 7.16 (m, 1H), 3.80 (t, 2H), 3.0 (t, 2H). HRMS: m/z calculated for $C_7H_9NOS_2$=187.0126, found 187.0128.

Synthesis of Compound 6: Synthesis of compound 6 was modified from literature (L. Mugherli, et al., *Bioorg Med Chem Lett*. 16, 4488-4491 (2006)). 1 g (2.5 mmol) Fluorescein was dissolved in 15 mL anhydrous DMF in a round bottom flask. 1.22 g (10 mmol) anhydrous potassium carbonate followed by 0.82 ml propargyl bromide (10 mmol) was added to it. The reaction mixture was then stirred at 65° C. for 4 h under inert atmosphere. DMF was evaporated under reduced pressure from the reaction mixture. The residue obtained was washed with water and filtered to afford a yellow solid as the product in 92% yield. $^1$H NMR (500 MHz, $CDCl_3$, TMS): δ (ppm): 8.25 (d, 1H), 7.80 (t, 1H), 7.68 (t, 1H), 7.33 (t, 1H), 7.06 (d, 1H), 6.81-6.79 (m, 3H), 6.55 (m, 1H), 6.45 (s, 1H), 4.79 (d, 2H), 4.58 (d, 2H), 2.61 (s, 1H), 2.33 (s, 1H). HRMS: m/z calculated for $C_{26}H_{16}O_5$=408.0998, found 408.0990.

Synthesis of Compound 7:0.8 g (1.9 mmol) compound 6 was dissolved in 5 mL THF in a round bottom flask. 2.5 g (62.5 mmol) NaOH was dissolved in 5 mL water and dropwise added to the reaction mixture. The mixture was stirred at room temperature for 4 hr and THF was evaporated under reduced pressure. The pH of the reaction mixture was adjusted to 2 by adding concentrated hydrochloric acid dropwise. A yellow precipitate was collected by vacuum filtration. Further the precipitate was purified by silica gel column chromatography using 20% ethyl acetate in petroleum ether. Yield=41%, $^1$H NMR (500 MHz, $CDCl_3$, TMS): δ (ppm): 8.02 (m, 1H), 7.67-7.63 (m, 2H), 7.17 (d, 1H), 6.87 (d, 1H), 6.74-6.69 (m, 4H), 6.54 (m, 1H), 4.72 (s, 2H), 2.56 (s, 1H), HRMS: m/z calculated for $C_{23}H_{14}O_5$=370.0841, found=370.0848.

Synthesis of Compound 8: Preparation of compound 8 was modified from the literature (E. A. Dubikovskaya, et al., *Proc Natl Acad Sci USA*. 105, 12128-12133 (2008)). 126 mg (0.68 mmol) compound 3 was taken in a round bottom flask and 1 mL anhydrous THF was added to it under inert atmosphere. Then 4 mL (15 wt % in toluene) phosgene solution was added dropwise to the reaction mixture at 0° C. and the mixture was stirred for 4 hr. THF as well as phosgene was evaporated by purging $N_2$ through the reaction mixture in a fume hood to obtain corresponding chloroformate. This precipitate was dissolved in dry THF (1 mL) and kept under $N_2$ atmosphere. In a separate round bottom flask 50 mg of compound 7 (0.135 mmol), dissolved in 0.5 ml anhydrous THF and 0.115 mL (0.811 mmol) triethylamine was mixed and cooled to 0° C. The chloroformate containing THF was then added slowly over a period of 15 minutes to compound 7 containing reaction mixture and stirred at 0° C.-RT overnight. After the completion, THF was evaporated from the reaction mixture under reduced pressure. Pure compound 8 was obtained by using preparative TLC (40% ethyl-acetate in hexane). Yield=40%. $^1$H NMR (500 MHz, $CDCl_3$, TMS): δ (ppm): 8.45 (m, 1H), 8.03 (d, 1H), 7.63 (m, 5H), 7.17 (m, 1H), 7.11 (m, 2H), 6.88 (m, 1H), 6.82 (m, 1H), 6.72 (m, 2H), 4.72 (s, 2H), 4.52 (m, 2H), 3.14 (m, 2H), 2.56 (s, 1H). $^{13}$C NMR ($CDCl_3$): δ (ppm): 169.1, 159.3, 152.9, 152.7, 152.1, 152.0, 151.9, 151.8, 149.8, 137.0, 135.1, 129.9, 129.1, 129.1, 129.1, 126.4, 125.1, 123.9, 121.0, 120.3, 120.1, 116.8, 112.5, 111.8, 109.7, 102.1, 82.1, 75.5, 66.4, 56.0, 36.8. HRMS: m/z calculated for $C_{31}H_{21}NO_7S_2$=583.076, found=583.0759.

Figure 12:
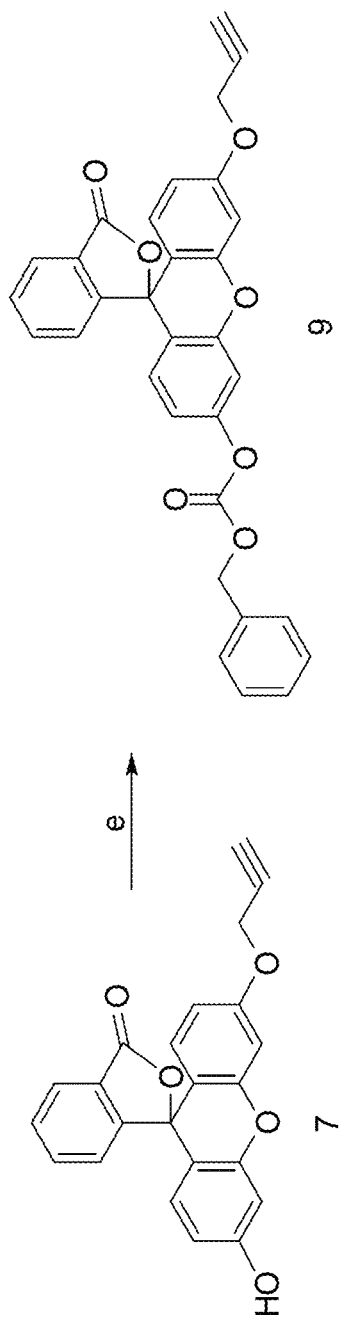
FIG. 12 illustrates a synthesis scheme of benzyl conjugated blocked 6'-O propargyl fluorescein.

Scheme 2: Synthesis of Benzyl conjugated blocked 6'-O propargyl fluorescein is shown in FIG. 12.

Reagents and conditions: e) Benzyl chloride, Triethylamine, anhydrous THF, 0° C.-rt, 12 h·yield=80%

Synthesis of Compound 9: 26 mg (0.07 mmol) compound 7 was dissolved in 2 mL anhydrous THF. Then 98 μL (0.7 mmol) of triethylamine was added to it and stirred at 0° C. under inert atmosphere for 5 minutes. 50 μL benzyl-chloroformate in 1 mL anhydrous THF was added dropwise to the reaction mixture. The mixture was stirred at 0° C. to room temperature under inert atmosphere for 12 h. THF was evaporated under reduced pressure. The residue was purified by silica gel flash column chromatography using 10% ethyl acetate in petroleum ether. An off white solid was obtained as the product in 80% yield. $^1$H NMR (500 MHz, CDCl$_3$, TMS): δ (ppm): 8.12 (d, 1H), 7.67 (m, 1H), 7.45-7.17 (m, 9H), 6.88-6.70 (m, 4H), 5.28 (s, 2H), 4.73 (d, 2H), 3.65 (s, 1H). $^{13}$C NMR (CDCl$_3$): δ (ppm): 169.1, 159.3, 153.0, 152.9, 152.3, 152.2, 151.8, 151.5, 135.1, 134.4, 129.9, 128.7, 128.7, 128.6, 128.6, 127.5, 126.9, 126.1, 125.1, 123.9, 116.9, 116.8, 112.5, 111.8, 109.8, 102.1, 82.1, 76.0, 70.6, 65.4, 56.0. HRMS: m/z calculated for $C_{31}H_{20}O_7$=504.1209, found=504.1212.

Synthesis of TDX Reporter (Catalytic Substrate Moiety):

Rhodamine and azide conjugated DNA-oligonucleotides were mixed in equimolar concentration (25 μM each) in 20 mM phosphate buffer containing 100 mM KCl at pH 7. The mixture was heated at 90° C. for 10 min and then cooled down to room temperature at the rate of 5° C./15 min and stored in 4° C. for overnight to form a complete DNA-duplex.

Figures 5A, 5B:
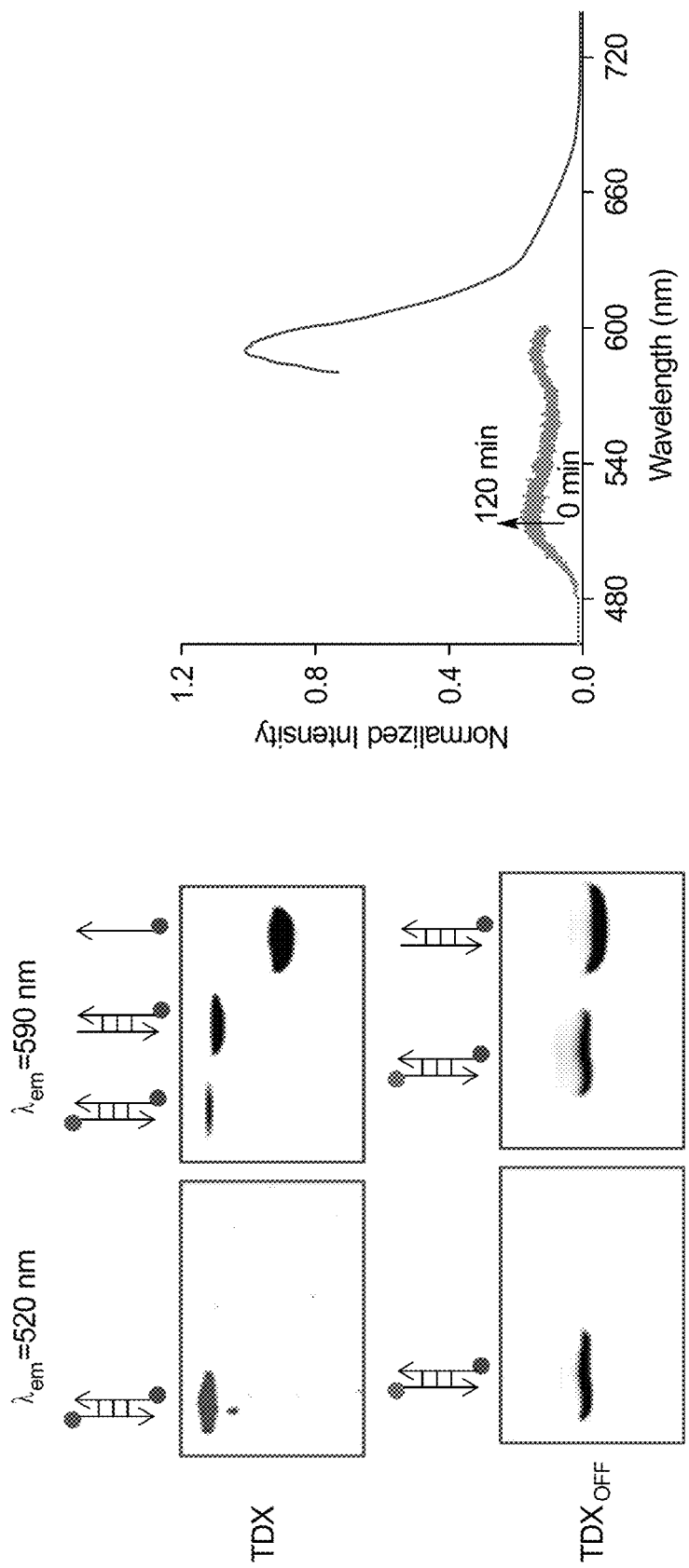
FIG. 5A illustrates 20% native polyacrylamide gel electrophoresis of TDX reporter (upper panel) and $TDX_{OFF}$ reporter (lower panel). The gel was run for 3 h at 150 mV in presence of 1×TBE (Tris-Borate-EDTA) buffer.
FIG. 5B illustrates the fluorescence signal evolution of $TDX_{OFF}$ at $\lambda_{em}$=520 nm and $\lambda_{em}$=590 nm in presence of 5 mM GSH at pH 7.2 at different time point.

Next, Rhodamine DNA-duplex was conjugated with compound 8 by reported copper catalysed azide-alkyne click chemistry protocol (S. I. Presolski, et al., Curr Protoc Chem Biol. 3, 153-162 (2011)). Initially 20 μL rhodamine conjugated DNA duplex was (25 μM) dissolved in 13.5 μL water, to that of 3 μL compound 8 (5 mM) in DMSO was added. Then 1:1 (v/v) premix solution of 7.5 μL of CuSO$_4$ (0.1M) and THPTA (0.2M) was added to it. The reaction mixture was degassed with N$_2$ for 2 min and followed by this 6 μL of sodium ascorbate (0.1M) was added. The mixture was further degassed for 0.5 min and then stirred at room temperature for 1 hr under N$_2$ atmosphere. Native PAGE (20%) showed complete formation of TDX reporter (FIGS. 1A and 5A). Subsequently, the reaction mixture was diluted with pH-6.0 phosphate buffer and washed with 10% acetonitrile (to remove excess of compound 8) using amicon filter (MWCO 3 KDa). The same washing procedure was continued until the filtrate showed no trace of compound 8 using fluorescence spectroscopy ($\lambda_{em}$=520 nm).

Synthesis of TDX$_{ON}$ reporter (positive control moiety): 10 μL TDX reporter (8 μM) was mixed with 1 μL (5 mM) NaSH solution in 0.1M phosphate buffer at pH 7.4 and stirred for 2 hr at room temperature. Followed by this, excess thiol was removed by ultracentrifugation using 3KDa MWCO membrane filter to obtain TDX$_{ON}$ reporter (see FIG. 1A).

Synthesis of TDX$_{OFF}$ reporter (background correction moiety): TDX$_{OFF}$ reporter was prepared in a similar procedure like TDX reporter, except compound 9 was used here instead of compound 8. The formation of TDX$_{OFF}$ reporter was characterized by using gel electrophoresis (see FIG. 5A).

Conjugation of compound 8 with azido dextran: 2 mg Azido functionalized dextran (10 kDa, 2-3 azido group per dextran) was dissolved in 90 μL milli Q water. 20 μL of compound 8 (5 mM), followed by 50 μL CuSO$_4$ (0.1M) and THPTA (0.2M) mixture (1:1) was added to it. The reaction mixture was degassed for 2 min and 40 μL sodium ascorbate (0.1M) was added, purged again with N$_2$ for 0.5 min before stirring at room temperature for 1 hr under N$_2$ atmosphere. The resulting dextran conjugate was diluted with milli Q water and washed with the 10% acetonitrile to remove excess of compound 8 using an amicon filter (MWCO 3 kDa).

Self-assembly of $I^{4647}_{FD}$: Half icosahedrons (VU$_5$ and VL$_5$) were prepared using the same procedure describe elsewhere (D. Bhatia, et al., Nat Commun. 2, 339 (2011)). In order to synthesize the DNA-icosahedron, VU$_5$ and VL$_5$ (3 μM each, 30 μL, in 50 mM phosphate buffer, pH 6.0) containing 2 mM solution of the compound 8 conjugated dextran (FD) (M. Wt.~10 KDa) was mixed in an Eppendorf tube and heated to 37° C. for 30 minutes. The temperature was brought down to 20° C. with a rate of 1° C./3 min and followed by incubation for 2 h. The reaction mixture was transferred to refrigerator at 4° C. for further incubation for longer time periods up to 48 hours. The formation of $I^{4647}_{FD}$ was characterized by 0.8% Agarose gel electrophoresis (FIG. 7A).

Preparation of $I^{4647}_{FD-ON}$: 10 μL solution (3 μM) of $I^{4647}_{FD}$ was treated with 1 μL (5 mM) NaSH solution in 0.1M phosphate buffer at pH 7.4 and stirred for 2 hr at room temperature. The excess thiol was removed by ultracentrifugation using 3 KDa MWCO membrane filter.

Determination of Size of different thiol: DLS experiment was done in Wyatt Dynapro Nanostar & Plate Reader. Samples were dissolved in milli-Q water or buffer filtered through 0.22 μm filter to remove dust particles. Samples were illuminated with laser wavelength of 658 nm, at a sensitivity of 80% and a scattering angle set at 90° with a 10 second acquisition time for data collection. Percentage intensity observed for each sample, was plotted against respective Rh values. The size of PEG-SH (3.2 KDa), Dex-SH (10KDa) and Dex-SH (40 KDa) was determined from DLS measurements. Aqueous solution of the free thiol containing polymer (1 mg/mL) was again filtered in a dust-free environment, and DLS measurement was carried out with this solution. For glutathione, cysteine and H$_2$S, the inventors used Chem 3D ultra 8.0 software and used the end to end distance of the energy minimized structure as diameter of those molecules.

In vitro fluorescence measurements: Fluorescence spectra were recorded on a FluoroMax-4 instrument (Horiba Jobin Yvon). TDX and TDX$_{OFF}$ reporter was diluted to 100 nM in 0.1M phosphate buffer at pH=7.2 in presence or absence of 5 mM GSH. These samples were excited at 450 nm (for fluorescein emission) and 575 nm (for rhodamine emission). The emission spectrum was collected between 460-600 nm and 590-700 nm for fluorescein and rhodamine respectively at different time point. Three independent measurements were recorded for each sample.

Figure 5C:
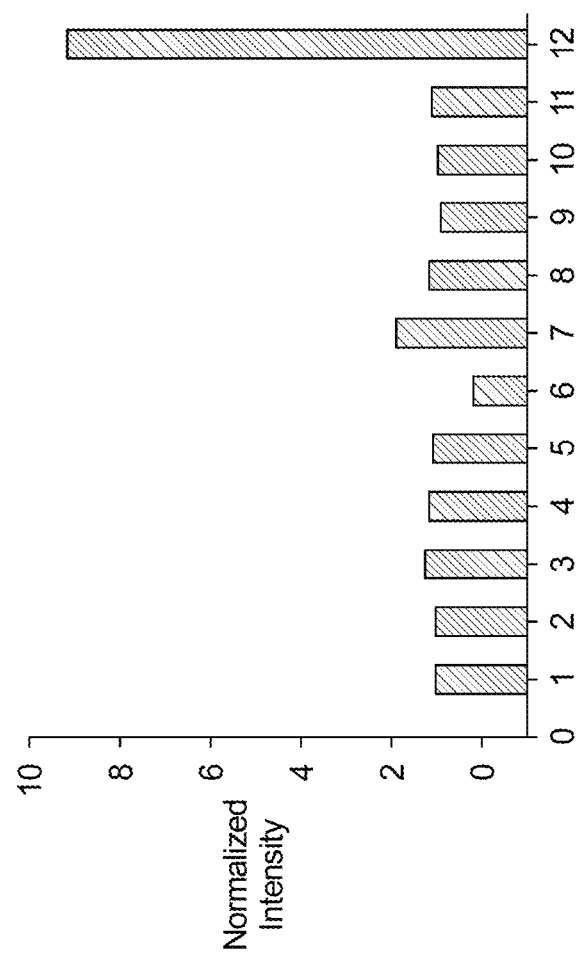
FIG. 5C illustrates the sensitivity of sensing dye, (compound 8) in presence of different analyte such as 1. Phosphate buffer (pH=7.2), 1 mM of 2. Na+, 3. K+, 4. Ca2+, 5. Fe2+, 6. Zn2+, and 5 mM of 7. $H_2O_2$, 8. His, 9. Ser, 10. Lys, 11. Val, and 12. Cys. Each intensity is normalized from the intensity of compound 8 before treatment with respective analytes.

The specificity of reporter dye was checked towards thiol disulfide exchange reaction and treated the reporter dye (compound 8) with different metal ions and amino acids. No reaction was observed with any of the metal ions and amino acids tested except cysteine (FIG. 5C).

In order to check the substrate availability for disulfide exchange reaction with $I^{4647}_{FD}$ as a function of the size of reactive thiols (1 mM), $I^{4647}_{FD}$ (3 μM) and FD was treated with various thiol and checked the emission spectra after 1 hour of incubation. For monitoring the emission spectra, the samples were excited at 450 nm (fluorescein channel) and 647 nm (Atto647 channel). The emission spectrum was collected between 460-600 nm and 650-750 nm for fluorescein and Atto647 respectively. (FIG. 7B).

Protocols for *C. elegans* and strains: Standard methods for the maintenance of *C. elegans* were followed. The inventors used wild type *C. elegans* strain isolated from Bristol (Strain N2). Mutant strain used for the experiment is V (586 [pdi-1(gk271) III].

Transgenic strains used for this study are; (i) cdIs131 [pcc1::GFP::rab-5+unc-119 (+)+myo-2p::GFP], a transgenic strain that express GFP-fused early endosomal marker RAB-5 inside coelomocytes. (ii) cdIs66 [pcc1::GFP::rab-7+ unc-119(+)+myo-2p::GFP], a transgenic strain that express GFP-fused late endosomal/lysosomal marker RAB-7 inside coelomocytes. (iii) pwIs50 [lmp-1::GFP+Cbr-unc-119(+)], a transgenic strain that express GFP-fused lysosomal marker LMP-1.

TDX and $I^{4647}_{FD}$ reporters targeted to coelomocyte of *C. elegans*: For coelomocyte targeting (D. Bhatia, et al, *Nat Commun*. 2, 339 (2011)), the inventors microinjected 2 µM of TDX reporter in the dorsal side in the pseudocoelom, just opposite to the vulva, of 1-day-old wild type hermaphrodites. Injected worms then placed in a new NGM agar containing petriplates at 22° C. for incubation at different time point. Followed by this they were mounted in an Agar pad (2.0%) and anaesthetized using 40 mM sodium azide in M9 buffer and performed fluorescence imaging experiment. Same protocol was followed in the case of $TDX_{OFF}$ and $TDX_{ON}$.

DNA-icosahedron encapsulated reporters, ($I^{4647}_{FD}$, $I^{4647}_{FD-ON}$ and $I^{4647}_{FD-OFF}$, 3 µM each) were injected to the wild type worms as described earlier and imaged at 30 min post-injection period.

Colocalization of $TDX^R$ with late endosomes in coelomocytes: In order to investigate the localization of TDX reporter at 20 minute post injection, the inventors have conducted co-localization experiment using cdIs131, cdIs66 and pwIs50 transgenic worms. For this, the inventors have injected 2 µM rhodamine DNA-duplex to these worms and imaged after 20 minutes. The inventors have observed ~85% co-localization of TDX reporter with RAB-7::GFP positive vesicles, which marks late endosomal and lysosomal compartments (see FIG. 2D and FIG. 9).

RNAi experiment: BLASTP (S. F. Altschul, et al, s, D. J. Lipman, Basic local alignment search tool. *J Mol Biol*. 215, 403-410 (1990). to look for thioredoxin domain containing protein in *C. elegans* genome. Bacteria of our interest, expressing double-stranded RNA (Table 3) were obtained from Ahringer RNAi library (R. S. Kamath, et al., *Methods*. 30, 313-321 (2003)) and Vidal Unique (J.-F. Rual et al., *Genome Res*. 14, 2162-2168 (2004)). Cloned bacteria were fed to the worms and ~60 one-day adults of the FI progeny were used for screening. The Ahringer or Vidal unique library did not contain bacterial clones for Y73B6BL.2 and hence this gene was not included in this screen.

mRNA was assayed to determine levels of the candidate genes by RT-PCR. Briefly, the inventors isolated total RNA using the Trizol-chloroform method; 2.5 µg of total RNA was converted to cDNA using oligo-dT primers. 5 µl of the reverse transcription reaction was used to set up a PCR using gene-specific primers. PCR products were analysed on a 1.5% agarose-TAE gel. Size of the PCR products expected for each gene were: actin (360 bp), pdi-3 (682 bp), (30H7.2 (798 bp), trx-2 (316 bp), trx-1 (261 bp).

Microscopy and ratiometric image analysis: Wide-field microscopy was performed on an IX83 inverted microscope (Olympus Corporation of the Americas, Center Valley, PA, USA) using a 60X, 1.42 NA, phase contrast oil immersion objective (PLAPON, Olympus Corporation of the Americas, Center Valley, PA, USA) and Evolve® Delta 512 EMCCD camera (Photometrics, USA). Filter wheel, shutter and CCD camera were controlled using Metamorph Premier Ver 7.8.12.0 (Molecular Devices, LLC, USA), appropriate for the fluorophore used. Images on the same day were acquired under the same acquisition settings. Confocal imaging was carried out on a Leica SP5 II STED-CW super-resolution microscope, using an Argon ion laser for 488 nm excitation and DPSS for 561 nm excitation with a set of dichroic, excitation, and emission filters suitable for each fluorophore. Crosstalk and bleed-through were measured and found to be negligible between GFP/fluorescein and Rhodamine.

All the images were background subtracted by using mean intensity calculated from an adjacent cell-free area. Fluorescein and Rhodamine images were colocalized and endosoms showing good colocalization were analysed using ImageJ-Win64 software (NIH). Mean fluorescence intensity in each endosome was measured in fluorescein (G) and rhodamine (R) channels. A ratio of G/R intensities was calculated from these values. Pseudocolour images were generated by measuring the G/R ratio per pixel. Using ImageJ software, pixels were then colour coded accordingly to indicate differences between high and low G/R ratios.

% Response Calculation: Percentage response of the TDX-reporter at different time points for the wild type worm and for the RNAi worm (20 min) were calculated using the following equation, % Response=$[^{G/R}TDX - ^{G/R}TDX_{OFF}/^{G/R}TDX_{ON} - ^{G/R}TDX_{OFF}] \times 100$. (Here, $^{G/R}TDX$, $^{G/R}TDX_{OFF}$ and $^{G/R}TDX_{ON}$ indicate the observed fluorescence intensity ratio of fluorescein to that of rhodamine at a given time point by using TDX, $TDX_{ON}$ and $TDX_{OFF}$ reporters respectively).

Statistical analysis of percentage (%) response: Graphpad unpaired t test calculator (available on the world wide web at graphpad.com/quickcalcs/ttest1/?Format+SEM) was used to check the statistical significance between the pdi-3, trx-1 and pdi-3, trx-1 double RNAi worm with wild type (N2) control.

5.1.7 Tables

TABLE 1

Mean G/R intensity ratio of $TDX_{ON}$, TDX and $TDX_{OFF}$ inside coelomocyte at different time points, post injection in *C. elegans* (N2).

| Time | Mean G/R of $TDX_{ON}$ | Mean G/R of TDX | Mean G/R of $TDX_{OFF}$ | % Response |
|---|---|---|---|---|
| 10 min | 0.24 ± 0.02 | 0.07 ± 0.05 | 0.05 ± 0.02 | 10% |
| 15 min | 0.24 ± 0.04 | 0.13 ± 0.03 | 0.05 ± 0.02 | 42% |
| 20 min | 0.26 ± 0.04 | 0.21 ± 0.03 | 0.04 ± 0.03 | 77% |
| 30 min | 0.26 ± 0.03 | 0.24 ± 0.04 | 0.05 ± 0.01 | 90% |
| 60 min | 0.20 ± 0.04 | 0.19 ± 0.04 | 0.05 ± 0.01 | 93% |

TABLE 2

Mean G/R intensity ratio of $TDX_{ON}$, TDX and $TDX_{OFF}$ and percentage (%) response of TDX reporter inside coelomocyte at 20 min post injection in different RNAi background worm.

| Mutant or RNAi worm | Mean G/R ratio of $TDX_{ON}$ | Mean G/R ratio of TDX | Mean G/R ratio of $TDX_{OFF}$ | % Response |
|---|---|---|---|---|
| pdi-1 | 0.24 ± 0.04 | 0.21 ± 0.07 | 0.05 ± 0.03 | 90 ± 4.6 |
| pdi-2 | 0.24 ± 0.06 | 0.21 ± 0.08 | 0.08 ± 0.02 | 82 ± 4.5 |
| pdi-3 | 0.28 ± 0.06 | 0.16 ± 0.06 | 0.05 ± 0.03 | 50 ± 2.3 |

TABLE 2-continued

Mean G/R intensity ratio of $TDX_{ON}$, TDX and $TDX_{OFF}$ and percentage (%) response of TDX reporter inside coelomocyte at 20 min post injection in different RNAi background worm.

| Mutant or RNAi worm | Mean G/R ratio of $TDX_{ON}$ | Mean G/R ratio of TDX | Mean G/R ratio of $TDX_{OFF}$ | % Response |
|---|---|---|---|---|
| C14B9.2 | 0.22 ± 0.07 | 0.21 ± 0.08 | 0.05 ± 0.02 | 99 ± 3.7 |
| pdi-6 | 0.26 ± 0.06 | 0.24 ± 0.05 | 0.06 ± 0.02 | 88 ± 3.6 |
| Y49E10.4 | 0.24 ± 0.08 | 0.21 ± 0.06 | 0.05 ± 0.02 | 93 ± 2.7 |
| M04D5.1 | 0.27 ± 0.08 | 0.23 ± 0.06 | 0.04 ± 0.03 | 88 ± 3.2 |
| C30H7.2 | 0.22 ± 0.04 | 0.21 ± 0.04 | 0.05 ± 0.02 | 90 ± 3.2 |
| trx-1 | 0.28 ± 0.07 | 0.19 ± 0.07 | 0.05 ± 0.03 | 63 ± 2.3 |
| trx-2 | 0.27 ± 0.08 | 0.25 ± 0.06 | 0.09 ± 0.01 | 89 ± 4.4 |
| Y55F3AR.2 | 0.22 ± 0.07 | 0.19 ± 0.08 | 0.05 ± 0.04 | 93 ± 3.8 |
| Y54E10A.3 | 0.23 ± 0.07 | 0.22 ± 0.07 | 0.07 ± 0.02 | 89 ± 3.1 |
| dpy-11 | 0.30 ± 0.08 | 0.28 ± 0.08 | 0.06 ± 0.04 | 98 ± 4 |
| C35D10.10 | 0.24 ± 0.06 | 0.22 ± 0.08 | 0.05 ± 0.03 | 89 ± 3.4 |
| F56G4.5 | 0.21 ± 0.09 | 0.20 ± 0.08 | 0.04 ± 0.03 | 97 ± 3.2 |

TABLE 3

Azido and Rhodamine labelled oligonucleotide sequences used for TDX reporters and others are used as primers for RT-PCR experiment.

| Name | Sequence |
|---|---|
| Azido labeled oligo | 5'-AzideN/AT ATA TAT GCC GAC TGC TGC ACT GAC CGC AGG AT (SEQ ID NO: 3) |
| Rhodamine labeled oligo | 5'-RhoR-N/AT CCT GCG GTC AGT GCA GCA GTC CCC ATA TAT AT (SEQ ID NO: 4) |
| pdi-3L | AATTCGGAGTTAAGGGATTC (SEQ ID NO: 5) |
| pdi-3R | TTGGTCCATTGGATACTTTC (SEQ ID NO: 6) |
| C30H-L | GAAGCCGCGAAAAGAGAGTA (SEQ ID NO: 7) |
| C30H-R | AAGCAGGCTTCAACTTCTCG (SEQ ID NO: 8) |
| trx-2L | CTTCAAAAATGACACAATTACG (SEQ ID NO: 9) |
| trx-2R | GAGAACGTCCTCGATAAAATC (SEQ ID NO: 10) |
| trx-1L | CTTGCTGATATGAGTGACTTTG (SEQ ID NO: 11) |
| trx-1R | ATACGTGCTCCAACACTTTTT (SEQ ID NO: 12) |

TABLE 4

Thioredoxin domain containing proteins present in *C. elegans* obtained from BLASTP search against *C. elegans* genome. Corresponding e values from best BLASTP match with *H. Sapiens* genome.

| | Candidate protein | E value |
|---|---|---|
| *C elegans* protein containing thioredoxin domain | PDI-1 | 9.59e-108 |
| | PDI-2 | 5.3e-155 |
| | PDI-6 | 1.4e-131 |
| | C14B9.2 | 4.1e-155 |
| | PDI-3 | 4.3e-112 |
| | Y49E10.4 | 7.4e-101 |
| | M04D5.1 | 5.8e-29 |
| | C30H7.2 | 1.4e-90 |
| | TRX-1 | 8.9e-18 |
| | TRX-2 | 1.1e-261 |
| | Y73B6BL.12 | 1.3e-17 |
| | Y55F3AR.2 | 9.9e-19 |
| | Y54E10A.3 | 8.2e-63 |
| | dpy-11 | 2.5e-54 |
| | C35D10.10 | 8.1e-50 |
| | F56G4.5 | 8.7e-75 |
| Thioredoxin protein with mitochondrial localization signal | F35G2.1 | 1.5e-43 |
| | T10H10.2 | 7.8e-49 |
| | F47B7.2 | 3.3e-57 |
| Thioredoxin protein with nuclear localization signal | C35B1.5 | 1.1e-19 |
| | trx-5 | 4e-22 |
| | trx-3 | 5e-15 |
| | F29B9.59 | 3e-17 |

5.2 Example 2: Probe for Spatiotemporal Detection of Thio-Esterase Activity in Endo-Lysosomal Compartment Described in this example is a DNA-based ratiometric probe that reports thio-esterase activity inside lysosome of live cells. Palmitoylation and depalmitoylation of various intracellular proteins plays an important role in intracellular protein trafficking and signaling in a variety of cell types. Palmitoyl protein thio-esterases (PPT) are presents in lysosomal compartment and catalyzed the depalmitoylation of its substrate protein. The loss of function of these specific protein leads to a neurological disorder called infantile neuronal ceroid lipofuscinosis 1 (INCL1) which leads to infantile death. In situ detection of PPT1 activity in live cells has diagnostic applications.

5.2.1 Design and Response of the PPT Probe for Thio-Esterase Activity

The PPT probe has three modules (FIG. 13A): a) a sensing module consisting of a reaction center for thio-esterase activity that leads to the formation of an active fluorophore; here the fluorophore is Rhodol; b) a normalizing module, consisting of a Alexa-647 dye whose fluorescence properties are insensitive to thioesterase activity and luminal environment of endocytic vesicle, and c) a targeting module consists of a 38 nucleotide DNA duplex comprising two oligonucleotides O-DBCO and O-Alexa 647 that serves two purposes. The first purpose is to display the sensing and normalizing modules in a precise, 1:1 stoichiometry. The second purpose is to target the entire assembly for uptake along the endo-lysosomal pathway by co-opting scavenger receptor mediated endocytic pathway. All three functions are integrated with stoichiometric precision by simply hybridizing DNA strands bearing each of these functionalities.

FIGS. 13A-E illustrate the spatiotemporal detection of thio-esterase activity by DNA based tripartite reporters. Specifically, FIG. 13A shows the structure of the PPT reporter (left): the sensing module (grey) is a protected rhodol dye conjugated with a thioester moiety, the normalizing module (red) is a thiol-insensitive Alexa 647 fluorophore, and the targeting module is a DNA duplex (black lines). The reporter (PPT) undergoes thioester hydrolysis to give highly fluorescent PPT$_{ON}$. PPT$_{OFF}$ (right) is a constitutively off version of PPT where rhodol is protected by a thioalkyl group non-responsive to thio-esterase. In FIG. 13B, the chemical structure of the protective Rhodol in PPT$_{OFF}$ and normalizing fluorophore Alexa 647 is provided. FIG. 13C shows the working principle of sensing module of PPT in presence of thio-esterase enzymes. FIG. 13D illustrates representative pseudo-color images of PPT reporter's present inside lysosomes of HEK cells. Finally, FIG. 13E includes a box plot showing G/R ratio of tripartite reporter (n=50 cells, ≥150 endosome) present in lysosome. Scale bar, 10 µm.

5.2.2 HEK Cells Detect PPT1 Activity Inside Lysosome

For quantitative detection of thio-esterase activity in lysosome, the inventors made another two devices such as PPT$_{ON}$ which will report the maximum response of the probe and PPT$_{OFF}$ which will report any nonspecific activity as well as the autofluorescence signal from the cell. The design of the tripartite reporter system and the chemical structure of the sensing module is shown in FIG. 13A. The inventors used HEK cells for the detection of the PPT1 activity inside lysosome. HEK cells lacks the scavenger receptor. Initially, the inventors transfected the cells with scavenger receptor type B and targeted the DNA device to the lysosomes via receptor mediated endocytosis. The inventors incubated the cells with 1 µM of each probe separately for 30 min at 37° C., followed by incubation of the cells without probe for 12 h at 37° C. The inventors then checked the thio-esterase activity by imaging live cells at Rhodol (G, 2 cm=525 nm) and Alexa 647 (R, 2 cm=670 nm) channel. At a given time point the ratiometric map of G/R intensities are generated and the pseudo-color images were presented in the FIG. 13D.

5.2.3 Materials and Methods

Synthesis of PPT, PPT$_{ON}$, PPT$_{OFF}$: HPLC purified oligonucleotides conjugated with either Alexa 647 or DBCO functional group were obtained from Integrated DNA Technologies (IDT, USA). DBCO and Alexa 647 conjugated DNA-oligonucleotides were mixed in equimolar concentration (30 µM each) in 20 mM phosphate buffer containing 100 mM KCl at pH 7. The mixture was heated at 90° C. for 10 min and then cooled down to room temperature at the rate of 5° C./15 min and stored in 4° C. for overnight to form a complete DNA-duplex.

Compound 1, 2 and 3 was synthesized according to literature. Next, the DNA duplex was conjugated with the Compound 1 via Cu free azide alkyne click chemistry. Initially, 16 µL A647 conjugate DNA duplex was diluted with 29 µL phosphate buffer (0.1 M) of pH=7.2, to that of 5 µL of compound 1 was added and stirred at room temperature for 1 h. Followed by the excess fluorophore was removed using Amicon Ultra-0.5 mL centrifugal filter (MWCO 10 kDa). Native PAGE (15 wt %) showed complete formation of the PPT reporter.

The PPT$_{ON}$ and PPT$_{OFF}$ synthesis, similar protocol was followed except the compound 2 and compound 3 was used respectively instead of Compound 1 for PPT probe.

Targeting PPT probe to endo-lysosomal pathway in HEK cells: HEK cells transfected with scavenger receptor A (kind gift from M. Schwake lab) and incubated for 48 h at 37° C. Followed by, it was pulsed with either PPT$_{ON}$, PPT and PPT$_{OFF}$ for 30 min at 37° C. in DMEM media without FBS.

After that, the cells were washed with PBS (pH=7.4) and chased for 12 h in complete media. Prior to imaging cells were washed with PBS and imaged in HBSS buffer (Hank's Balanced Salt Solution, GE healthcare).

Microscopy and ratiometric image analysis: Wide-field microscopy was performed on an IX83 inverted microscope (Olympus Corporation of the Americas, Center Valley, PA, USA) using a 60×, 1.42 NA, phase contrast oil immersion objective (PLAPON, Olympus Corporation of the Americas, Center Valley, PA, USA) and Evolve® Delta 512 EMCCD camera (Photometrics, USA). Filter wheel, shutter and CCD camera were controlled using Metamorph Premier Ver 7.8.12.0 (Molecular Devices, LLC, USA), appropriate for the fluorophore used. Images on the same day were acquired under the same acquisition settings. All the images were background subtracted by using mean intensity calculated from an adjacent cell-free area. Rhodol (G) and Alexa 647 (R) images were colocalized and endosomes showing good colocalization were analyzed using ImageJ-Win64 software (NIH). Mean fluorescence intensity in each endosome was measured in fluorescein (G) and rhodamine (R) channels. A ratio of G/R intensities was calculated from these values. Pseudocolor images were generated by measuring the G/R ratio per pixel. Using ImageJ software, pixels were then color coded accordingly to indicate differences between high and low G/R ratios.

5.3 Example 3: Probe for Spatiotemporal Detection of Cathepsin Activity in Lysosomes Lysosomes are the degradation centers for extracellular material taken up by endocytosis and intracellular material by autophagy. In the lysosomal system, protein degradation is a result of the combined action of various proteases. Cysteine cathepsin proteases are a group on such hydrolases which play a key role in MHC class II complex, bone remodeling, keratinocyte differentiation, tumor progression and metastasis, rheumatoid arthritis, osteoarthritis and atherosclerosis. As such, detection of endo-lysosomal cathepsin activity in live cells has diagnostic applications.

Described in this example is a DNA based ratiometric probe that reports on cathepsin protein activity inside lysosomes of live cells. The inventors have created two such probes for two cathepsin proteins which have been highly associated to tumor progression and inflammatory response: Cathepsin B/L and Cathepsin C. The DNA probes integrate all three desired functionalities-sensing, quantitation, and targeting—in precise ratios onto a single scaffold by hybridizing DNA strands bearing each functionality. The inventors have leveraged (i) the diversity available to small molecule probes, (ii) a range of organic fluorophores for quantitation, (iii) high stability of dsDNA in acidic pH, and (iv) the specific targetability of these probes. The reporter module consists of a DNA strand (R), bearing an azido-rhodamine with both amines protected by coupling to dipeptide moieties (FIG. 14A-B) that are substrates for a specific cathepsin. Cathepsin C cleaves the N-terminus of the dipeptide Gly-Phe. Cathepsin B and L cleave N terminal protected Cbz-Phe-Lys. When the dipeptide protecting groups are cleaved by the relevant cathepsin, rhodamine fluorescence is recovered. The azido-Rhodamine-(dipeptide) 2 will be attached to a dibenzylcyclooctyl-DNA strand (DBCO-DNA) by click chemistry to give strand R. The normalizing module uses an A647N labeled DNA strand, R' for ratiometry that is complementary to R. The targeting moiety comprises the duplex RR' which localizes in lysosomes by binding scavenger receptors.

5.3.1 Design and Response of Reporter Sensing System for Cathepsin Activity

The design of the reporter system and the chemical structure of the sensing module is shown in FIG. 14. J774A.1 cells were used for the detection of the cathepsin activity inside lysosome. The inventors incubated the cells with 500 nM of each probe separately for 30 min at 37° C. Followed by incubation of the cells for 1 h in complete medium at 37° C. The inventors then imaged for the cathepsin activity by imaging live cells in Rhod (G, λem=520 nm) and Alexa 647 (R, λem=670 nm) channel.

Figure 14B:
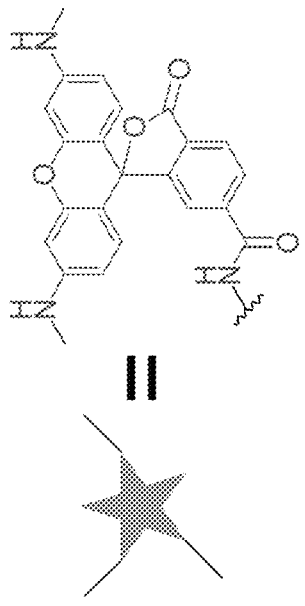
FIG. 14A-D shows the design and response of reporter sensing system for cathepsin activity described in the Example 3.
Figure 14D:
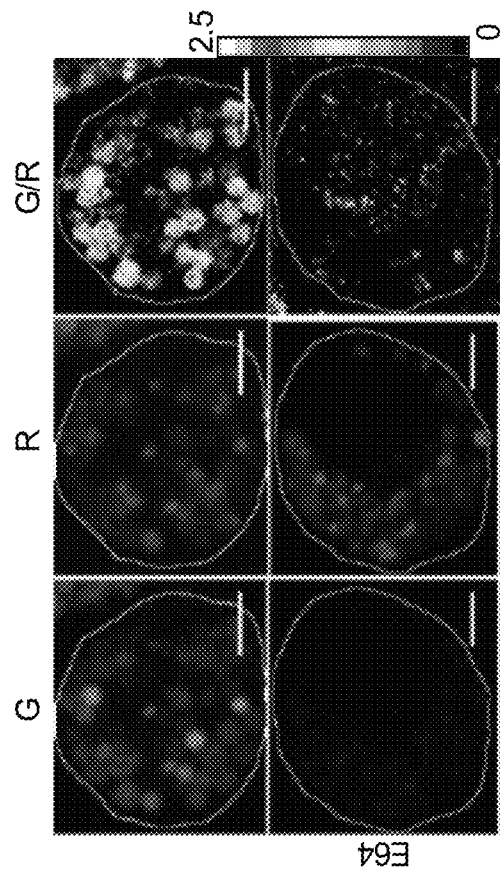
Figure 14A:
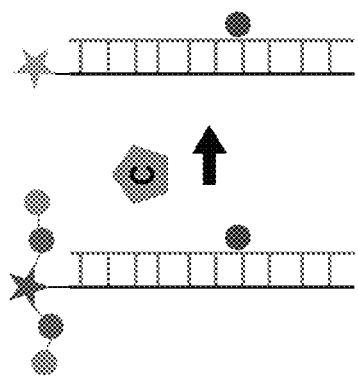
Figure 14C:
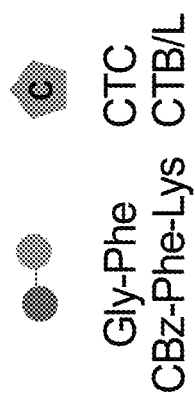

FIGS. 14A-14D illustrate the detection of the cathepsin activity inside lysosome. FIG. 14A illustrates the cathglo probes for various cathepsins (pentagon). FIG. 14B shows rhodamine (star) is attached to DNA and protected by pendant peptides that are substrates for specific cathepsins. FIG. 14C shows the sequences of pendant peptide substrates and their corresponding cathepsins. FIG. 14D shows the upper panels: fluorescence image of reacted CathgloC in lysosomes of J774A.1 cells in the rhodamine (G) and Atto647N (R) channels and the ratiometric image (G/R). Lower panels are the activity images in the presence of a cathepsin C inhibitor E64. Scale bar: 5 μm.

5.3.2 Materials and Methods

Synthesis of CathgloC and CathgloB: HPLC purified oligonucleotides conjugated with either Alexa 647 or DBCO functional group were obtained from Integrated DNA Technologies (IDT, USA). DBCO and Alexa 647 conjugated DNA-oligonucleotides were mixed in equimolar concentration (20 μM each) in 20 mM phosphate buffer containing 100 mM KCl at pH 7. The mixture was heated at 90° C. for 10 min and then cooled down to room temperature at the rate of 5° C./15 min and stored in 4° C. for overnight to form a complete DNA-duplex.

Azide labelled Rhodamine 110 labelled with specific dipeptide sequences using protocols from literature. Next, the DNA duplex was conjugated with the protected rhodamine via Cu free azide alkyne click chemistry. This was followed by removing the excess fluorophore using Amicon Ultra-0.5 mL centrifugal filter (MWCO 10 kDa). Gel electrophoresis showed formation of the cathepsin reporter.

Targeting probe to lysosomes in J774A.1 cells: J774A. 1 cells were pulsed with 500 nM of a Cathglo probe for 30 mins at 370C, washed and imaged after 1 h of incubation in complete medium. Images were acquired in brightfield, Rhodamine 110 (green; G) and A647 (red; R) channels.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. C. B. Anfinsen, Principles that govern the folding of protein chains. Science. 181, 223-230 (1973).
2. M. J. Gething, J. Sambrook, Protein folding in the cell. Nature. 355, 33-45 (1992).
3. A. Jansens, E. van Duijn, I. Braakman, Coordinated nonvectorial folding in a newly synthesized multidomain protein. Science. 298, 2401-2403 (2002).
4. P. J. Hogg, Disulfide bonds as switches for protein function. Trends Biochem Sci. 28, 210-214 (2003).
5. M. C. Yi, C. Khosla, Thiol-Disulfide Exchange Reactions in the Mammalian Extracellular Environment. Annu Rev Chem Biomol Eng. 7, 197-222 (2016).
6. J. R. Burgoyne et al., Cysteine redox sensor in PKGIa enables oxidant-induced activation. Science. 317, 1393-1397 (2007).
7. M.-Y. Wang et al., A redox switch in C-reactive protein modulates activation of endothelial cells. FASEB J. 25, 3186-3196 (2011).
8. J. E. Mills et al., A novel disulfide bond in the SH2 Domain of the C-terminal Src kinase controls catalytic activity. J Mol Biol. 365, 1460-1468 (2007).
9. D. S. Collins, E. R. Unanue, C. V. Harding, Reduction of disulfide bonds within lysosomes is a key step in antigen processing. J Immunol. 147, 4054-4059 (1991).
10. B. S. Stolf et al., Protein disulfide isomerase and host-pathogen interaction. Scientific World Journal. 11, 1749-1761 (2011).
11. P. Guermonprez et al., ER-phagosome fusion defines an MHC class I cross-presentation compartment in dendritic cells. Nature. 425, 397-402 (2003).
12. H. Mok, S. H. Lee, J. W. Park, T. G. Park, Multimeric small interfering ribonucleic acid for highly efficient sequence-specific gene silencing. Nat Mater. 9, 272-278 (2010).
13. C. Liu et al., Eradication of large colon tumor xenografts by targeted delivery of maytansinoids. Proc Natl Acad Sci USA. 93, 8618-8623 (1996).
14. J. Yang, H. Chen, I. R. Vlahov, J.-X. Cheng, P. S. Low, Evaluation of disulfide reduction during receptor-mediated endocytosis by using FRET imaging. Proc Natl Acad Sci USA. 103, 13872-13877 (2006).
15. W. C. Shen, H. J. Ryser, L. LaManna, Disulfide spacer between methotrexate and poly(D-lysine). A probe for exploring the reductive process in endocytosis. J Biol Chem. 260, 10905-10908 (1985).
16. E. Feener, W.-C. Shen, H. Ryser, Cleavage of Disulfide Bonds in Endocytosed Macromolecules.
17. J. B. Lloyd, Disulphide reduction in lysosomes. The role of cysteine. Biochem J. 237, 271-272 (1986).
18. S. Short, B. J. Merkel, R. Caffrey, K. L. McCoy, Defective antigen processing correlates with a low level of intracellular glutathione. Eur J Immunol. 26, 3015-3020 (1996).
19. S. Bhuniya et al., An activatable theranostic for targeted cancer therapy and imaging. Angew Chem Int Ed Engl. 53, 4469-4474 (2014).
20. S. Maiti et al., Gemcitabine-coumarin-biotin conjugates: a target specific theranostic anticancer prodrug. J Am Chem Soc. 135, 4567-4572 (2013).

21. M. H. Lee et al., Hepatocyte-targeting single galactose-appended naphthalimide: a tool for intracellular thiol imaging in vivo. J Am Chem Soc. 134, 1316-1322 (2012).
22. M. M. Pires, J. Chmielewski, Fluorescence imaging of cellular glutathione using a latent rhodamine. Org Lett. 10, 837-840 (2008).
23. K. Chakraborty, A. T. Veetil, S. R. Jaffrey, Y. Krishnan, Nucleic Acid-Based Nanodevices in Biological Imaging. Annu Rev Biochem. 85, 349-373 (2016).
24. J. Liu, Z. Cao, Y. Lu, Functional nucleic acid sensors. Chem Rev. 109, 1948-1998 (2009).
25. M. Famulok, J. S. Hartig, G. Mayer, Functional aptamers and aptazymes in biotechnology, diagnostics, and therapy. Chem Rev. 107, 3715-3743 (2007).
26. S. Modi, C. Nizak, S. Surana, S. Halder, Y. Krishnan, Two DNA nanomachines map pH changes along intersecting endocytic pathways inside the same cell. Nat Nanotechnol. 8, 459-467 (2013).
27. S. Saha, V. Prakash, S. Halder, K. Chakraborty, Y. Krishnan, A pH-independent DNA nanodevice for quantifying chloride transport in organelles of living cells. Nat Nanotechnol. 10, 645-651 (2015).
28. S. Modi et al., A DNA nanomachine that maps spatial and temporal pH changes inside living cells. Nat Nanotechnol. 4, 325-330 (2009).
29. D. Bhatia, S. Surana, S. Chakraborty, S. P. Koushika, Y. Krishnan, A synthetic icosahedral DNA-based host-cargo complex for functional in vivo imaging. Nat Commun. 2, 339 (2011).
30. D. Bhatia et al., Quantum dot-loaded monofunctionalized DNA icosahedra for single-particle tracking of endocytic pathways. Nat Nanotechnol. 11, 1112-1119 (2016).
31. H. Lee et al., Molecularly self-assembled nucleic acid nanoparticles for targeted in vivo siRNA delivery. Nat Nanotechnol. 7, 389-393 (2012).
32. S. Surana, J. M. Bhat, S. P. Koushika, Y. Krishnan, An autonomous DNA nanomachine maps spatiotemporal pH changes in a multicellular living organism. Nat Commun. 2, 340 (2011).
33. Z. Wu, D. Liang, X. Tang, Visualizing Hydrogen Sulfide in Mitochondria and Lysosome of Living Cells and in Tumors of Living Mice with Positively Charged Fluorescent Chemosensors. Anal Chem. 88, 9213-9218 (2016).
34. D. Bhatia et al., Icosahedral DNA nanocapsules by modular assembly. Angew Chem Int Ed Engl. 48, 4134-4137 (2009).
35. S. F. Altschul, W. Gish, W. Miller, E. W. Myers, D. J. Lipman, Basic local alignment search tool. J Mol Biol. 215, 403-410 (1990).
36. H. C. Hawkins, E. C. Blackburn, R. B. Freedman, Comparison of the activities of protein disulphide-isomerase and thioredoxin in catalysing disulphide isomerization in a protein substrate. Biochem J. 275 (Pt 2), 349-353 (1991).
37. S. C. P. Eschenlauer, A. P. Page, The *Caenorhabditis elegans* ERp60 homolog protein disulfide isomerase-3 has disulfide isomerase and transglutaminase-like cross-linking activity and is involved in the maintenance of body morphology. J Biol Chem. 278, 4227-4237 (2003).
38. H. Dihazi et al., Secretion of ERP57 is important for extracellular matrix accumulation and progression of renal fibrosis, and is an early sign of disease onset. J Cell Sci. 126, 3649-3663 (2013).
39. A. Rubartelli, A. Bajetto, G. Allavena, E. Wollman, R. Sitia, Secretion of thioredoxin by normal and neoplastic cells through a leaderless secretory pathway. J Biol Chem. 267, 24161-24164 (1992).
40. C. V. Smith, D. P. Jones, T. M. Guenthner, L. H. Lash, B. H. Lauterburg, Compartmentation of glutathione: implications for the study of toxicity and disease. Toxicol Appl Pharmacol. 140, 1-12 (1996).
41. A.-R. Karala, A.-K. Lappi, L. W. Ruddock, Modulation of an active-site cysteine pKa allows PDI to act as a catalyst of both disulfide bond formation and isomerization. J Mol Biol. 396, 883-892 (2010).
42. J. D. Forman-Kay, G. M. Clore, A. M. Gronenborn, Relationship between electrostatics and redox function in human thioredoxin: characterization of pH titration shifts using two-dimensional homo- and heteronuclear NMR. Biochemistry. 31, 3442-3452 (1992).
43. C. Wu et al., Thioredoxin 1-mediated post-translational modifications: reduction, transnitrosylation, denitrosylation, and related proteomics methodologies. Antioxid Redox Signal. 15, 2565-2604 (2011).
44. F. Pacello, M. D'Orazio, A. Battistoni, An ERp57-mediated disulphide exchange promotes the interaction between *Burkholderia cenocepacia* and epithelial respiratory cells. Sci Rep. 6, 21140 (2016).
45. S. Burgdorf, C. Schölz, A. Kautz, R. Tampé, C. Kurts, Spatial and mechanistic separation of cross-presentation and endogenous antigen presentation. Nat Immunol. 9, 558-566 (2008).
46. L. Lasecka, M. D. Baron, The nairovirus nairobi sheep disease virus/ganjam virus induces the translocation of protein disulphide isomerase-like oxidoreductases from the endoplasmic reticulum to the cell surface and the extracellular space. PLOS ONE. 9, e94656 (2014).
47. A. Y. Santana, C. A. Guerrero, O. Acosta, Implication of Hsc70, PDI and integrin $\alpha v\beta 3$ involvement during entry of the murine rotavirus ECwt into small-intestinal villi of suckling mice. Arch Virol. 158, 1323-1336 (2013).
48. E. Prifti et al., A fluorogenic probe for SNAP-tagged plasma membrane proteins based on the solvatochromic molecule Nile Red. ACS Chem Biol. 9, 606-612 (2014).
49. G. V. Los et al., HaloTag: a novel protein labeling technology for cell imaging and protein analysis. ACS Chem Biol. 3, 373-382 (2008).
50. G. Crivat, J. W. Taraska, Imaging proteins inside cells with fluorescent tags. Trends Biotechnol. 30, 8-16 (2012).
51. Chan P, Han X, Zheng B, DeRan M, Yu J, Jarugumilli G K, et al. Autopalmitoylation of TEAD proteins regulates transcriptional output of the Hippo pathway. Nat Chem Biol. 2016 April; 12 (4): 282-289.
52. Linder M E, Deschenes R J. Palmitoylation: policing protein stability and traffic. Nat Rev Mol Cell Biol. 2007 January; 8 (1): 74-84.
53. Zhang Z, Lee Y-C, Kim S-J, Choi MS, Tsai P-C, Xu Y, et al. Palmitoyl-protein thioesterase-1 deficiency mediates the activation of the unfolded protein response and neuronal apoptosis in INCL. Hum Mol Genet. 2006 Jan. 15; 15 (2): 337-346.
54. Van Diggelen O P, Keulemans J L, Winchester B, Hofman I L, Vanhanen S L, Santavuori P, et al. A rapid fluorogenic palmitoyl-protein thioesterase assay: pre- and postnatal diagnosis of INCL. Mol Genet Metab. 1999 April; 66 (4): 240-244.
55. Kathayat R S, Elvira P D, Dickinson B C. A fluorescent probe for cysteine depalmitoylation reveals dynamic APT signaling. Nat Chem Biol. 2017; 13 (2): 150-152.
56. Xu, H. & Ren, D. Lysosomal physiology. Annu Rev Physiol 77, 57-80 (2015).
57. Appelqvist, H., Wäster, P., Kågedal, K. & Öllinger, K. The lysosome: from waste bag to potential therapeutic target. J Mol Cell Biol 5, 214-226 (2013).

58. Turk, V. et al. Cysteine cathepsins: from structure, function and regulation to new frontiers. Biochim Biophys Acta 1824, 68-88 (2012).
59. Berg, T. O., Strømhaug, E., Løvdal, T., Seglen, O. & Berg, T. Use of glycyl-L-phenylalanine 2-naphthylamide, a lysosome-disrupting cathepsin C substrate, to distinguish between lysosomes and prelysosomal endocytic vacuoles. Biochem J 300 (Pt 1), 229-236 (1994).
60. Wang, Y. et al. Lysosome-Targeting Fluorogenic Probe for Cathepsin B Imaging in Living Cells. Anal Chem 88, 12403-12410 (2016).
61. Blum, G., von Degenfeld, G., Merchant, M. J., Blau, H. M. & Bogyo, M. Noninvasive optical imaging of cysteine protease activity using fluorescently quenched activity-based probes. Nat Chem Biol 3, 668-677 (2007).
62. Modi, S. et al. A DNA nanomachine that maps spatial and temporal pH changes inside living cells. Nat Nanotechnol 4, 325-330 (2009).
63. Modi, S., Nizak, C., Surana, S., Halder, S. & Krishnan, Y. Two DNA nanomachines map pH changes along intersecting endocytic pathways inside the same cell. Nat Nanotechnol 8, 459-467 (2013).
64. Saha, S., Prakash, V., Halder, S., Chakraborty, K. & Krishnan, Y. A pH-independent DNA nanodevice for quantifying chloride transport in organelles of living cells. Nat Nanotechnol 10, 645-651 (2015).
65. Chakraborty, K., Leung, K. & Krishnan, Y. High lumenal chloride in the lysosome is critical for lysosome function. elife 6, e28862 (2017).
66. Li, J. et al. Substrate optimization for monitoring cathepsin C activity in live cells. Bioorg Med Chem 17, 1064-1070 (2009).
67. U.S. Pat. No. 8,153,437
68. U.S. Pat. No. 8,216,850
69. U.S. patent application Ser. No. 12/474,550
70. US patent application U.S. Ser. No. 14/351,400
71. International Patent application PCT/IB2014/059236
72. International Patent Application PCT/IB2012/055515
73. Indian Patent application 1471/CHE/2011
74. Indian Patent application 3252/CHE/2011

The invention claimed is:

1. A composition comprising:
a first nucleic acid; and
a second nucleic acid;
wherein the first nucleic acid and the second nucleic acid are in a nucleic acid duplex;
and wherein the first nucleic acid comprises SEQ ID NO:1 and the second nucleic acid comprises SEQ ID NO:2, or wherein the first nucleic acid comprises SEQ ID NO:2 and the second nucleic acid comprises SEQ ID NO:1.

2. The composition of claim 1 further comprising a catalytic substrate conjugated to the first nucleic acid or the second nucleic acid
wherein the first nucleic acid is conjugated to a normalization moeity.

3. The composition of claim 2, wherein the catalytic substrate is an enzymatic substrate, and wherein reaction of the catalytic substrate with an enzyme produces a detectable product.

4. The composition of claim 2, wherein the normalization moiety and the catalytic substrate are in a 1:1 ratio.

5. The composition of claim 3, wherein the detectable product is fluorescent.

6. The composition of claim 2, wherein the catalytic substrate comprises a disulfide bond.

7. The composition of claim 2, wherein the catalytic substrate comprises a thioester moiety.

8. The composition of claim 2, wherein the catalytic substrate comprises Gly-Phe or Cbz-Phe-Lys.

9. The composition of claim 2, wherein the catalytic substrate comprises a protected fluorophore.

10. The composition of claim 2, wherein the catalytic substrate is derived from 6'-O propargyl fluorescein.

11. The composition of claim 2, wherein the catalytic substrate comprises:

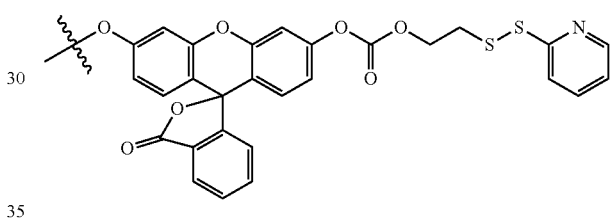

12. The composition of claim 3, wherein the reaction comprises a thiol disulfide exchange.

13. The composition of claim 3, wherein the normalization moiety and the detectable product each comprise a fluorophore comprising an emission wavelength.

14. The composition of claim 13, wherein the fluorophore of the normalization moiety and the fluorophore of the detectable product have different emission wavelengths.

15. The composition of claim 1, wherein the duplex directs a cell to localize the duplex to the endosome or lysosome.

16. The composition of claim 1, wherein the duplex directs a cell to target one of the endoplasmic reticulum or golgi.

17. A kit comprising: the composition of claim 1.

18. The composition of claim 2, wherein the first nucleic acid is conjugated to the catalytic substrate.

* * * * *